US010430549B2

(12) United States Patent
Backhaus

(10) Patent No.: US 10,430,549 B2
(45) Date of Patent: *Oct. 1, 2019

(54) TELERADIOLOGY IMAGE PROCESSING SYSTEM

(71) Applicant: Virtual Radiologic Corporation, Minneapolis, MN (US)

(72) Inventor: Brent Backhaus, Lakeville, MN (US)

(73) Assignee: Virtual Radiologic Corporation, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/966,594

(22) Filed: Aug. 14, 2013

(65) Prior Publication Data

US 2014/0088987 A1  Mar. 27, 2014

Related U.S. Application Data

(63) Continuation of application No. 13/449,004, filed on Apr. 17, 2012, now Pat. No. 8,515,778, which is a
(Continued)

(51) Int. Cl.
*G16H 40/20* (2018.01)
*G06F 19/00* (2018.01)
(Continued)

(52) U.S. Cl.
CPC ........... *G06F 19/321* (2013.01); *G06Q 10/06* (2013.01); *G06Q 50/22* (2013.01); *G16H 15/00* (2018.01); *G16H 80/00* (2018.01)

(58) Field of Classification Search
CPC .............................. G16H 40/20; G06Q 10/063
See application file for complete search history.

(56) References Cited

U.S. PATENT DOCUMENTS 3,995,106 A  11/1976 Wern et al.
4,003,023 A   1/1977 Benson et al.
(Continued)

FOREIGN PATENT DOCUMENTS

WO  WO-01/99407 A1    12/2001
WO  WO-2005/006138 A2  1/2005
WO  WO-2006/093544 A2  9/2006
(Continued)

OTHER PUBLICATIONS

"14-Step RIS/PACS Selection Process", [Online]. [Archived Apr. 27, 2004]. Retrieved from the Internet: <URL: http://web.archive.org/web/20040427134813/http://www.merge.com/pdf/14%20Step%20RIS-PACS%20Selection%20Process.pdf>, 2 pgs.
(Continued)

Primary Examiner — John A Pauls
(74) Attorney, Agent, or Firm — Schwegman Lundberg & Woessner, P.A.

(57) ABSTRACT

A teleradiology image processing system configured to receive, process, and transmit radiology read requests and digital radiology image data is disclosed herein. In one embodiment, a radiology processing system includes a series of processing components configured to receive digital radiology data from a medical provider, extract relevant information and radiology scan images from the digital radiology data, and initiate and control a workflow with a qualified remote radiologist who ultimately performs a read of the radiology scan images. Further embodiments also facilitate data processing within the image processing system in response to medical facility rules and preferences; translation or conversion of digital images to other formats; compilation of patient and medical facility data obtained from the digital radiology data into medical records or data stores; assignment of radiology studies within a teleradiology workflow in response to licensing and credentialing rules; and billing functions in response to completed reads by the remote radiologist.

22 Claims, 12 Drawing Sheets

Related U.S. Application Data continuation of application No. 12/870,271, filed on Aug. 27, 2010, now Pat. No. 8,195,481, which is a continuation-in-part of application No. 12/783,073, filed on May 19, 2010, now Pat. No. 7,925,521, which is a continuation of application No. 11/288,645, filed on Nov. 28, 2005, now Pat. No. 7,729,928.

(60) Provisional application No. 60/740,454, filed on Nov. 28, 2005, provisional application No. 60/740,527, filed on Nov. 28, 2005, provisional application No. 60/740,589, filed on Nov. 28, 2005, provisional application No. 60/699,119, filed on Jul. 14, 2005, provisional application No. 60/694,880, filed on Jun. 29, 2005, provisional application No. 60/682,052, filed on May 17, 2005, provisional application No. 60/656,215, filed on Feb. 25, 2005.

(51) Int. Cl.
  G06Q 10/06 (2012.01)
  G06Q 50/22 (2018.01)
  G16H 80/00 (2018.01)
  G16H 15/00 (2018.01)

(56) References Cited

U.S. PATENT DOCUMENTS

| | | |
|---|---|---|
| 4,058,335 A | 11/1977 | Kennedy |
| 4,261,018 A | 4/1981 | Knowlton |
| 4,302,775 A | 11/1981 | Widergren et al. |
| 4,458,267 A | 7/1984 | Dolazza |
| 4,463,386 A | 7/1984 | Goddard et al. |
| 4,541,012 A | 9/1985 | Tescher |
| 4,604,653 A | 8/1986 | Shimizu |
| 4,614,978 A | 9/1986 | Doster et al. |
| 4,622,585 A | 11/1986 | Reitsma |
| 4,631,521 A | 12/1986 | El-sherbini |
| 4,652,933 A | 3/1987 | Koshiishi |
| 4,748,511 A | 5/1988 | Nicols et al. |
| 4,764,870 A | 8/1988 | Haskin |
| 4,860,112 A | 8/1989 | Nichols et al. |
| 4,910,609 A | 3/1990 | Nicholas et al. |
| 5,216,596 A | 6/1993 | Weinstein et al. |
| 5,291,401 A | 3/1994 | Robinson |
| 5,321,520 A | 6/1994 | Inga et al. |
| 5,416,602 A | 5/1995 | Inga et al. |
| 5,452,416 A | 9/1995 | Hilton et al. |
| 5,469,353 A | 11/1995 | Pinsky et al. |
| 5,469,535 A | 11/1995 | Jarvis et al. |
| 5,513,101 A | 4/1996 | Pinsky et al. |
| 5,631,953 A | 5/1997 | Thomas et al. |
| 5,655,084 A | 8/1997 | Pinsky et al. |
| 6,006,191 A | 12/1999 | DiRienzo |
| 6,035,276 A | 3/2000 | Newman et al. |
| 6,115,486 A | 9/2000 | Cantoni |
| 6,137,527 A | 10/2000 | Abdel-malek et al. |
| 6,272,470 B1 | 8/2001 | Teshima |
| 6,302,844 B1 | 10/2001 | Walker et al. |
| 6,314,452 B1 | 11/2001 | Dekel et al. |
| 6,381,029 B1 | 4/2002 | Tipirneni |
| 6,424,996 B1 | 7/2002 | Killcommons et al. |
| 6,448,956 B1 | 9/2002 | Berman et al. |
| 6,473,524 B1 | 10/2002 | Reda et al. |
| 6,481,887 B1 | 11/2002 | Mirabella |
| 6,571,214 B2 | 5/2003 | Newman et al. |
| 6,574,629 B1 | 6/2003 | Cooke, Jr. et al. |
| 6,603,494 B1 | 8/2003 | Banks et al. |
| 6,621,918 B1 | 9/2003 | Hu et al. |
| 6,625,252 B2 | 9/2003 | Mirabella |
| 6,678,703 B2 | 1/2004 | Rothschild et al. |
| 6,798,533 B2 | 9/2004 | Tipirneni |
| 6,820,057 B1 | 11/2004 | Loch et al. |
| 6,876,759 B2 | 4/2005 | Keller et al. |
| 6,915,266 B1 | 7/2005 | Saeed et al. |
| 7,136,883 B2 | 11/2006 | Flamma et al. |
| 7,500,185 B2 | 3/2009 | Hu |
| 7,562,026 B2 | 7/2009 | DelMonego et al. |
| 7,729,928 B2 | 6/2010 | Backhaus et al. |
| 7,756,724 B2 | 7/2010 | Gropper et al. |
| 7,925,521 B2 | 4/2011 | Backhaus et al. |
| 7,970,634 B2 | 6/2011 | Backhaus et al. |
| 8,090,593 B2 | 1/2012 | Backhaus et al. |
| 8,145,503 B2 | 3/2012 | Backhaus et al. |
| 8,195,481 B2 | 6/2012 | Backhaus |
| 8,229,761 B2 | 7/2012 | Backhaus et al. |
| 8,515,778 B2 | 8/2013 | Backhaus |
| 8,612,250 B2 | 12/2013 | Backhaus et al. |
| 8,612,253 B2 | 12/2013 | Backhaus et al. |
| 2001/0032215 A1 | 10/2001 | Kyle et al. |
| 2001/0041991 A1 | 11/2001 | Segal et al. |
| 2002/0016718 A1 | 2/2002 | Rothschild et al. |
| 2002/0019751 A1 | 2/2002 | Rothschild et al. |
| 2002/0065758 A1 | 5/2002 | Henley |
| 2002/0087503 A1 | 7/2002 | Judd et al. |
| 2002/0102012 A1 | 8/2002 | Keller et al. |
| 2002/0102028 A1 | 8/2002 | Keller et al. |
| 2002/0109859 A1 | 8/2002 | Tipirneni |
| 2002/0161605 A1 | 10/2002 | Newman et al. |
| 2002/0169637 A1 | 11/2002 | Akers et al. |
| 2002/0198454 A1 | 12/2002 | Seward et al. |
| 2003/0004409 A1 | 1/2003 | Mueller et al. |
| 2003/0061090 A1 | 3/2003 | Marano |
| 2003/0086595 A1 | 5/2003 | Hu et al. |
| 2003/0126148 A1* | 7/2003 | Gropper ............... G06F 19/327 |
| 2003/0149598 A1 | 8/2003 | Santoso et al. |
| 2004/0064343 A1 | 4/2004 | Korpman et al. |
| 2004/0117617 A1 | 6/2004 | Geller et al. |
| 2004/0167402 A1 | 8/2004 | Jones et al. |
| 2004/0186764 A1 | 9/2004 | Mcneill |
| 2004/0254822 A1 | 12/2004 | Mandelbaum |
| 2004/0257608 A1 | 12/2004 | Tipirneni |
| 2005/0002483 A1 | 1/2005 | Wilcox, Jr. |
| 2005/0021375 A1 | 1/2005 | Shimizu et al. |
| 2005/0075902 A1 | 4/2005 | Wager et al. |
| 2005/0101856 A1 | 5/2005 | Judd et al. |
| 2005/0114380 A1 | 5/2005 | Eldar et al. |
| 2005/0234741 A1 | 10/2005 | Rana et al. |
| 2006/0053035 A1 | 3/2006 | Eisenberg |
| 2006/0095423 A1 | 5/2006 | Reicher et al. |
| 2006/0168338 A1 | 7/2006 | Bruegl et al. |
| 2006/0195339 A1 | 8/2006 | Backhaus et al. |
| 2007/0005798 A1 | 1/2007 | Gropper et al. |
| 2007/0073556 A1 | 3/2007 | Lau et al. |
| 2009/0089092 A1 | 4/2009 | Johnson et al. |
| 2009/0198559 A1 | 8/2009 | Wang et al. |
| 2009/0327049 A1 | 12/2009 | Kisin et al. |
| 2010/0198609 A1 | 8/2010 | Mellin et al. |
| 2010/0256986 A1 | 10/2010 | Backhaus et al. |
| 2011/0004490 A1 | 1/2011 | Backhaus et al. |
| 2011/0010192 A1 | 1/2011 | Backhaus et al. |
| 2011/0015941 A1 | 1/2011 | Backhaus |
| 2011/0066449 A1 | 3/2011 | Backhaus et al. |
| 2011/0191118 A1 | 8/2011 | Backhaus et al. |
| 2012/0245949 A1 | 9/2012 | Backhaus et al. |
| 2012/0265551 A1 | 10/2012 | Backhaus et al. |
| 2012/0323593 A1 | 12/2012 | Backhaus |
| 2013/0066646 A1 | 3/2013 | Backhaus et al. |
| 2014/0142969 A1 | 5/2014 | Backhaus et al. |
| 2014/0142983 A1 | 5/2014 | Backhaus et al. |

FOREIGN PATENT DOCUMENTS

| | | |
|---|---|---|
| WO | WO-2006093544 A2 | 9/2006 |
| WO | WO-2010/087911 A1 | 8/2010 |
| WO | WO-2012/064819 A1 | 5/2012 |

OTHER PUBLICATIONS

"All-In-One Server", [Online]. [Archived Jul. 15, 2004]. Retrieved from the Internet: <URL: http://web.archive.org/web/20040715234715/http://www.medweb.com/all_in_one.pdf >, 4 pgs.

(56) References Cited

OTHER PUBLICATIONS

"U.S. Appl. No. 13/084,379, Preliminary Amendment dated Jun. 30, 2011", 14 pgs.
"U.S. Appl. No. 13/084,379, Preliminary Amendment dated Oct. 21, 2011", 16 pgs.
"U.S. Appl. No. 13/449,004, Preliminary Amendment dated Apr. 17, 2012", 3 pgs.
"U.S. Appl. No. 13/449,004, Preliminary Amendment dated Sep. 12, 2012", 10 pgs.
"U.S. Appl. No. 13/550,319, Notice of Allowance dated Jun. 26, 2014", 11 pgs.
"U.S. Appl. No. 13/550,319, Preliminary Amendment dated Jun. 16, 2014", 10 pgs.
"U.S. Appl. No. 13/550,319, Preliminary Amendment dated Jul. 16, 2012", 3 pgs.
"U.S. Appl. No. 13/550,319, Preliminary Amendment dated Nov. 30, 2012", 6 pgs.
"U.S. Appl. No. 13/550,319, Preliminary Amendment dated Dec. 21, 2012", 9 pgs.
"U.S. Appl. No. 14/079,284, Preliminary Amendment dated Nov. 11, 2013", 3 pgs.
"Building Referrals Through Internet Gateways", [Online]. [Archived Dec. 13, 2004]. Retrieved from the Internet: <URL: http://web.archive.org/web/20041213164514/http://www.merge.com/pdf/Internet%20Gateways%20White%20Paper.pdf>, 8 pgs.
"Canadian Application Serial No. 2,636,705, Office Action dated Jul. 17, 2012", 4 pgs.
"Canadian Application Serial No. 2,636,705, Response filed Sep. 11, 2014 to Office Action dated Mar. 12, 2014", 4 pgs.
"Canadian Application Serial No. 2,636,705, Response filed Dec. 18, 2012 to Office Action dated Jul. 17, 2012", 14 pgs.
"Compact Conversion Device for Non-DICOM Modalities", [Online]. [Archived May 17, 2000]. Retrieved from the Internet: <URL: http://web.archive.org/web/20000517131011/http://www.medweb.net/html/dicomizer.html>, 1 pg.
"Complete teleradiology reporting and distribution workflow solution", [Online]. [Archived May 31, 2004]. Retrieved from the Internet: <URL: http://web.archive.org/web/20040531042632/http://www.thinairdata.com/docs/SkyRISTeleradiology.pdf>, 2 pgs.
"Complete workflow, reporting and distribution solution for multi-contract radiology and teleradiology", [Online]. [Archived Nov. 12, 2004]. Retrieved from the Internet: <URL: http://web.archive.org/web/20041112122403/http://www.thinairdata.com/docs/ThinAirData_TeleRIS.pdf>, 2 pgs.
"Defendants' 2nd Amended Prior Art Statement", *Virtual Radiologic Corporation, et al. v. Tandem Radiology, LLC, et al.*,, Civil Action No. 2:13-cv-01705-DKD, United States District Court for the District of Arizona, (Aug. 18, 2014), 19 pgs.
"DICOM Cube", [Online]. [Archived Feb. 19, 1999. Retrieved from the Internet: <URL: http://web.archive.org/web/19990219213946/http://www.medweb.com/html/dicom_cube.html>, 1 pg.
"DICOM Cube, Raq3, Raq4 Mixed Input Clinical Webservers", [Online]. Retrieved from the Internet: <URL: http://web.archive.org/web/20040206094442/http://www.medweb.com/Mixed_Input_Webservers.pdf>, (2002), 4 pgs.
"Dictation, Transcription and Practice Management", [Online]. [Archived Jul. 16, 2004]. Retrieved from the Internet: <URL: http://web.archive.org/web/20040716024128/http://www.medweb.com/Dictation_Transcription.pdf>, 2 pgs.
"Digital Publisher Gateway", [Online]. [Archived Jul. 3, 2003]. Retrieved from the Internet: <URL: http://web.archive.org/web/20030703020011/http://www.medweb.com/CD_spec_sheet.pdf>, 2 pgs.
"European Application Serial No. 05852463.8, Search Report dated Feb. 24, 2010", 6 pgs.
"Full feature RIS with integrated speech recognition and transcription", [Online]. [Archived Jun. 9, 2003]. Retrieved from the Internet: <URL: http://web.archive.org/web/20030609085309/http://thinairdata.com/docs/SkyRIS.pdf>, 2 pgs.
"Full feature RIS with integrated speech recognition and transcription", [Online]. [Archived Jul. 27, 2004]. Retrieved from the Internet: <URL: http://web.archive.org/web/20040727053227/http://www.thinairdata.com/docs/SkyRIS.pdf>, 2 pgs.
"Fusion RIS/PACS: Intelligent, Distributed Workflow", [Online]. [Archived Jun. 16, 2004]. Retrieved from the Internet: <URL: http://web.archive.org/web/20040616013014/http://www.merge.com/products/pacsteleradiologyweb/fusion_rispacs.asp>, 2 pgs.
"Improving Profitability with E-Document Delivery", [Online]. [Archived Feb. 19, 2004]. Retrieved from the Internet: <URL: http://web.archive.org/web/20040219180157/http://www.merge.com/pdf/Improving%20Profitability%20with%20E-Document%20Delivery.pdf>, 4 pgs.
"Medweb", [Online]. [Archived Apr. 17, 1999]. Retrieved from the Internet: <URL: http://web.archive.org/web/19990417045341/http://www.medweb.com/>, 1 pg.
"Medweb", [Online]. [Archived Jan. 16, 1998]. Retrieved from the Internet: <URL: http://web.archive.org/web/19980116194946/http://www.medweb.com/>, 1 pg.
"Medweb", [Online]. [Archived Nov. 11, 1998]. Retrieved from the Internet: <URL: http://web.archive.org/web/19981111184528/http://www.medweb.com/>, 2 pgs.
"Medweb", [Online]. [Archived Dec. 7, 1998]. Retrieved from the Internet: <URL: http://web.archive.org/web/19981207045132/http://www.medweb.com/>, 1 pg.
"Medweb—Image Server DICOM Conformance Statement Revision 2.1", [Online]. Retrieved from the Internet: <URL: http://web.archive.org/web/20030817102556/http://www.medweb.com/DICOM_Conformance_Image_Server.pdf>, (Jul. 1, 1998), 20 pgs.
"Medweb Browser Plug-Ins", [Online]. [Archived Mar. 2, 2000]. Retrieved from the Internet: <URL: http://web.archive.org/web/20000302082914/http://www.medweb.com/html/plug-ins.html>, 2 pgs.
"Medweb Image Viewer Plugin", [Online]. [Archived Apr. 14, 2003]. Retrieved from the Internet: <URL: http://web.archive.org/web/20030414183706/http://medweb.com/html/plug-ins.html>, 2 pgs.
"Medweb Introduced Breakthrough Web-based Enterprise Telemedicine Solution", [Online]. [Archived Mar. 2, 2000]. Retrieved from the Internet: <URL: http://web.archive.org/web/20000302143424/http://www.medweb.com/html/pr-ets.html>, 2 pgs.
"Medweb Introduces Breakthrough Web-based Enterprise Telemedicine Solution", [Online]. [Archived Apr. 8, 2000]. Retrieved from the Internet: <URL: http://web.archive.org/web/20000408232851/http://www.medweb.net/html/t-server.html>, 2 pgs.
"Medweb Introduces New TELEMED Cube Bi-Directional Telemedicine Server", [Online]. [Archived Apr. 8, 2001]. Retrieved from the Internet: <URL: http://web.archive.org/web/20010408055000/http://www.medweb.com/html/t-cube.html>, 2 pgs.
"Medweb Introduces the DICOM Cube, Complete Web-Based Solution for Distribution of DICOM Studies", [Online]. [Archived Mar. 2, 2000]. Retrieved from the Internet: <URL: http://web.archive.org/web/20000302122612/http://www.medweb.com/html/pr-dcube.html>, 3 pgs.
"Medweb PDA Gateway", [Online]. [Archived Jul. 16, 2004]. Retrieved from the Internet: <URL: http://web.archive.org/web/20040716045513/http://www.medweb.com/pda_Gateway.pdf>, 1 pg.
"Medweb RIS With Integrated Web Scheduler", [Online]. [Archived Jul. 16, 2004]. Retrieved from the Internet: <URL: http://web.archive.org/web/20040716023259/http://www.medweb.com/RIS.pdf>, 2 pgs.
"Merge Radiology Solutions", [Online]. Retrieved from the Internet: <URL: http://www.merge.com/Solutions/Radiology.aspx>, (Accessed Oct. 31, 2014), 4 pgs.
"MGRIS—Global Radiology Information System", [Online]. [Archived Oct. 22, 2004]. Retrieved from the Internet: <URL: http://web.archive.org/web/20041022044754/http://www.medweb.com/mgris_pdf.pdf>, 1 pg.
"MGRIS—Global Radiology Information System", [Online]. [Archived Jul. 16, 2004]. Retrieved from the Internet: <URL: http://web.archive.org/web/20040716030818/http://www.medweb.com/mgris_pdf.pdf>, 1 pg.

(56) References Cited

OTHER PUBLICATIONS

"PACSGUARDIAN", [Online]. [Archived Jul. 16, 2004]. Retrieved from the Internet: <URL: http://web.archive.org/web/20040716013608/http://www.medweb.com/pacsguardian_pdf.pdf >, 2 pgs.

"Practice Analysis—Converting Data to Profits", [Online]. [Archived Feb. 19, 2004]. Retrieved from the Internet: <URL: http://web.archive.org/web/20040219151236/http://www.merge.com/pdf/Practice%20Analysis%20White%20Paper.pdf >, 11 pgs.

"Radiologist Dashboard", [Online]. [Archived May 12, 2005]. Retrieved from the Internet: <URL: http://web.archive.org/web/20050512075349/http://www.medweb.com/Dashboard.pdf >, 2 pgs.

"RIS Logic Module Features", [Online]. [Archived Jan. 5, 2004]. Retrieved from the Internet: <URL: http://web.archive.org/web/20040105160056/http://www.merge.com/products/pacsteleradiologyweb/rislogiccs_features.asp>, 6 pgs.

"SkyRIS DR", [Online]. [Archived Jun. 7, 2001]. Retrieved from the Internet: <URL: http://web.archive.org/web/20010607094324/http://thinairdata.com/SkyRIS/DR/dr.html >, 1 pg.

"Smart Monitor: Multi-Site monitoring software for remote radiology reading services and distributed failsafe, secure, reading networks", [Online]. [Archived Jul. 16, 2004]. Retrieved from the Internet: <URL: http://web.archive.org/web/20040716013538/http://www.medweb.com/smart_monitor.pdf >, 2 pgs.

"Survey Documents That a RIS Reduces Turnaround Time by 20%", [Online]. [Archived Feb. 19, 2004]. Retrieved from the Internet: <URL: http://web.archive.org/web/20040219145635/http://www.merge.com/pdf/Turnaround%20Time%20Results.pdf >, 2 pgs.

"Telemed Rack—Medweb Distributed Telemedicine", [Online]. [Archived Jul. 16, 2004]. Retrieved from the Internet: <URL: http://web.archive.org/web/20040716030816/http://www.medweb.com/telemed_brochure.pdf >, 8 pgs.

"TeleRIS is the complete teleradiology workflow, reporting and distribution solution", [Online]. [Archived Oct. 19, 2004]. Retrieved from the Internet: <URL: http://web.archive.org/web/20041019125202/http://thinairdata.com/SkyRISTele.htm >, 3 pgs.

"TeleRIS is the complete teleradiology, multi-contract, multi-facility workflow, reporting and distribution solution", [Online]. [Archived Dec. 9, 2004]. Retrieved from the Internet: <URL: http://web.archive.org/web/20041209091915/http:www.thinairdata.com/SkyRISTele.htm >3 pgs.

"The RIS Logic CS Solution—Benefits", [Online]. [Archived Apr. 28, 2004]. Retrieved from the Internet: <URL: http://web.archive.org/web/20040428181757/http://www.merge.com/products/pacsteleradiologyweb/rislogiccs_benefits.asp>, 2 pgs.

"ThinAir Data", [Online]. [Archived Oct. 23, 2006]. Retrieved from the Internet: <URL: http://web.archive.org/web/20061023222251/http://www.thinairdata.com/docs/ThinAir_VRC_Story_030106.pdf>, 2 pgs.

"ThinAir Data—SkyRIS DR", [Online]. [Archived Jun. 7, 2001]. Retrieved from the Internet: <URL: http://web.archive.org/web/20010607094324/http://thinairdata.com/SkyRIS/DR/dr.html >, 1 pg.

"Welcome: ThinAir Data—Healthcare at the Speed of Thought", [Online]. [Archived Nov. 12, 2004]. Retrieved from the Internet: <URL: http://web.archive.org/web/20041112045011/http://www.thinairdata.com >, 2 pgs.

"24/7 Radiology Services", 24/7 Radiology, LLP. [online]. [retrieved on Nov. 2, 2006]. Retrieved from the Internet: <URL: http://www.247rad.comiservice.shtml>, (2004), 2 pgs.

"About HL7", Health Level Seven. [online]. [retrieved on Jul. 15, 2005]. Retrieved from the Internet: <URL: www.hl7.org/about/about_nav_bar.cfm>, (2005), 15 pgs.

"About IHE", IHE Initiative: ACC/HIMSS/RSNA. [online]. [retrieved on Jul. 15, 2005]. Retrieved from the Internet: <URL: http://www.ihe.net/About/index.cfm>, (2005), 2 pgs.

"About Us!, Emergency Radiology", [online]. [retrieved on Nov. 2, 2006]. Retrieved from the Internet: <URL: http://www.emergencyradiology.net/aboutus.htm>, (2006), 1 pg.

"ACUO Technologies Products, ACUO Technology Product Webpage, Overview and Functionality data for (AcuoMed Image Manager & AcuoStore Digital Asses Manager)", ACUO Technologies, [online]. [retrieved on Nov. 28, 2005]. Retrieved from the Internet: <URL: http://www.acuotech.com/acuoArchive.htrnl>, (2005), 5 pgs.

"ACUO Technology DICOM Archive", Acuo Technologies, LLC. [online]. [retrieved on Nov. 13, 2006]. Retrieved from the Internet: <URL: http://www.acuotech.com/acuoArchive.htrnl>, 3 pgs.

"American Radiology offers Images Online to Referring Physicians", American Radiology Services, Inc. [online]. [archived on Feb. 23, 2005]. Retrieved from the Internet: <URL:http://www3.americanradiology.com/pls/web1/wwparticle.viewart?article_id_in=23>, (2003), 1 pg.

"American Radiology Services Nighthawk Services", © 2003 American Radiology Services, Inc. [online]. [retrieved on Nov. 29, 2005]. Retrieved from the Internet: <URL: ]. http://www3.americanradiology.com/pls/web1/wwreadserv.info>, (2003), 2 pgs.

"American Radiology Services Organization Information", © 2003 American Radiology. [online]. [retrieved on Feb. 25, 2005]. Retrieved from the Internet: <URL: http://www3.americanradiology.com/pls/web11wwaboutars.info >, (2003), 3 pgs.

"American Radiology Services, Inc.—Organization Information", © 2003 American Radiology. [online], [retrieved on Feb. 25, 2005]. Retrieved from the Internet: <URL: http://www3.americanradiology.com/pls/web1/wwaboutars.info>, (2003), 3 pgs.

"APEX Radiology: A Virtual Radiologist on Staff", Apple Computer, Inc. [online]. [retrieved on Oct. 20, 2006]. Retrieved from the Internet: <URL: http://www.apple.com/science/profiles/apexl >, (2006), 4 pgs.

"U.S. Appl. No. 11/288,645, Non Final Office Action dated Nov. 12, 2009", 20 pgs.

"U.S. Appl. No. 11/288,645, Notice of Allowance dated Mar. 24, 2010", 12 pgs.

"U.S. Appl. No. 11/288,645, Preliminary Amendment dated Mar. 27, 2006", 4 pgs.

"U.S. Appl. No. 11/288,645, Response filed Feb. 12, 2010 to Non Final Office Action dated Nov. 12, 2009", 13 pgs.

"U.S. Appl. No. 12/783,073, Notice of Allowance dated Feb. 22, 2011", 9 pgs.

"U.S. Appl. No. 12/783,073, Preliminary Amendment dated Jan. 10, 2011", 7 pgs.

"U.S. Appl. No. 12/870,271, Notice of Allowance dated Feb. 24, 2012", 9 pgs.

"U.S. Appl. No. 12/882,479, Notice of Allowance dated Mar. 23, 2011", 11 pgs.

"U.S. Appl. No. 12/882,479, Preliminary Amendment dated Jan. 10, 2011", 10 pgs.

"U.S. Appl. No. 13/084,379, Notice of Allowance dated Nov. 8, 2011", 13 pgs.

"U.S. Appl. No. 13/333,767, Non Final Office Action dated Mar. 20, 2013", 18 pgs.

"U.S. Appl. No. 13/423,513, Non Final Office Action dated Mar. 19, 2013", 16 pgs.

"U.S. Appl. No. 90/009,889, Examiner Interview Summary dated Jun. 28, 2011", 3 pgs.

"U.S. Appl. No. 90/009,889, Notice of Failure to Comply dated May 6, 2011", 8 pgs.

"U.S. Appl. No. 90/009,889, Order dated Jul. 13, 2011 Denying Request for ex parte Reexmation", 14 pgs.

"U.S. Appl. No. 90/009,889, Petition for Reconsideration filed Aug. 10, 2011", 14 pgs.

"U.S. Appl. No. 90/009,889, Revised Request for Re-Examination filed May 30, 2011", 10 pgs.

"Benefits", © 2004 Fujifilm UK. [online]. [retrieved on Nov. 28, 2005]. Retrieved from the Internet: <URL: www.fujifilm.co.uk/synapse/about/benefits>, (2004), 3 pgs.

"Cactus Advantage", Cactus Software. [online]. [retrieved on Nov. 2, 2006]. Retrieved from the Internet: <URL: http://www.visualcactus.com/Public2002/MCCACTUSAdvantageFull, (2006), 3 pgs.

"Cactus Software Products & Services", [online]. [retrieved on Nov. 2, 2006]. Retrieved from the Internet: <URL: http://www.visualcactus.com/Public2002/HomeFramedPage.htm>, (2006), 1 pg.

"California Radiographics Homepage", California Radiographics Inc. [online]. [retrieved on Sep. 7, 2005]. Retrieved from the Internet: <URL: http://www.nightshiftradiology.com/teleradiology_equipment.htm>, (2005), 4 pgs.

(56) References Cited

OTHER PUBLICATIONS

"Cascadable Architecture", © 2004 Fujifilm UK. [online]. [retrieved on Nov. 28, 2005]. Retrieved from the Internet: <URL: www.fujifilm.co.uk/synapse/product/cascadable>, (2004), 2 pgs.

"Case Studies EchoApps", © 2006 Healthline Systems Inc. [online]. [retrieved on Nov. 2, 2006]. Retrieved from the Internet: <URL: http://www.healthlinesystems.com/casestudies/echoapps_mc.asp>, (2006), 5 pgs.

"Chatham Radiology Group Deploys Neurostar's Virtual Radiology Network Solution to Improve Service and Productivity", © 2003 Neurostar Solutions. [online]. [retrieved Apr. 26, 2005]. Retrieved from the Internet: <URL: www.neurostarsolutions.com/index/jsp?page=PressRelease&newsID=2>, (2003), 3 pgs.

"Comply Product Overview", Strategic Management Group LLC. [online]. [retrieved on Nov. 2, 2006]. Retrieved from the Internet: <URL: http://www.complysoftware.com/>, (2006), 2 pgs.

"Credentialing Software from Intellisoft", Intellisoft Group, Inc. [online]. [retrieved on Nov. 2, 2006]. Retrieved from the Internet: <URL: http://www.intellisoftgroup.com/>, 3 pgs.

"Database Management System", © 2004 Fujifilm UK. [online]. [retrieved on Nov. 28, 2005]. Retrieved from the Internet: <URL: www.fujifilm.co.uk/synapse/technical/database>, (2004), 1 pg.

"Desktop User Interface", © 2004 Fujifilm UK. [online]. [retrieved on Nov. 28, 2005]. Retrieved from the Internet: <URL: www.fujifilm.co.uk/synapse/product/desktop>, (2004), 2 pgs.

"Developing the Complete Teleradiology Infrastructure", The Hawk—The NightHawk Radiology Services Newsletter, (2005), 2 pgs.

"Diagna Radiology", [online]. [retrieved on Feb. 25, 2005]. Retrieved from the Internet: <URL: http://www.diagna.com/>, (2005), 12 pgs.

"Diagnosticimaging.com—Radiology is Going Places Let Us Take You There First", CMP Healthcare Media Group LLC. [online]. [retrieved on Nov. 30, 2005]. Retrieved from the Internet: <URL: www.diagnosticimaging.com >, (2005), 4 pgs.

"DICOM Conformance Statement for Cedara I-SoftView", Cedara Software Corp, Document No. 2004-02987, (2005), 1-38.

"EchoApps", Healthline Systems Inc. [online]. [retrieved on Sep. 6, 2005]. Retrieved from the Internet: <URL: http://www.healthlinesystems.com/echoapps_mc.asp>, (2005), 3 pgs.

"EchoApps—Simplify the Provider Application Process", © 2004 HealthLine Systems Inc.[online]. retrieved on Nov. 28, 2005]. Retrieved from the Internet: <URL: http://echomc.comlechoappsproces2.asp>, (2004), 2 pgs.

"EchoApps Quick Tour, 12 Screen Captures", HealthLine Systems Inc. [online]. [retrieved on Nov. 28, 2005]. Retrieved from the Internet: <URL: http://healthlinesystems.com/demos/echoapps_demo.htm>, (2005), 13 pgs.

"EHR Clinical Overview", U.S. Department of Health and Human Services—Indian Health Service, [Online]. [retrieved on Jul. 15, 2005]. Retrieved from the Internet: <URL: http://www.ihs.gov/CIO/EHR/index.cfm?module=clinicaloverview>, (2005), 2 pgs.

"eMed—Test Drive Register", eMed® Technologies. [online]. [retrireved on Jul. 15, 2005]. Retrieved from the Internet: <URL: www.emed.com/products_services/matrix.php>, (2003), 4 pgs.

"Emergency Radiology Home Page", [online]. [retrieved on Nov. 12, 2006]. Retrieved from the Internet: <URL: http://www.emergencyradiology.net/missionstatement.htm>, (2006), 1 pg.

"Enterprise Image Management", GE Medical Systems. [online]. [retrieved on Jul. 15, 2005] Retrieved from the Internet: <URL: www.gehealthcare.com/img_info_systems/centricity_ris/products/enterprise_img.html>, (2005), 2 pgs.

"Epic Teleradiology Services", © 2006 Epic Teleradiology. [online]. [retrieved on Nov. 2, 2006], Retrieved from the Internet: <URL: http://www.epictele.com/services.php>, (2006), 1 pg.

"European Application Serial No. 94908280.4, Entscheidung, vol. 9, Board of Appeal of the European Patent Office", (Feb. 2005), 19 pgs.

"European Application Serial No. 94908280.4, Office Action dated Feb. 8, 2005", (2005), 19 pgs.

"Ex Parte Re-examination Request re: Backhaus et al., U.S. Pat. No. 7,729,928 filed Dec. 17, 2010", (Dec. 17, 2010), 11 pgs.

"External Information System", (c) 2004 Fujifilm UK. [online]. [retrieved on Nov. 28, 2005]. Retrieved from the Internet: <URL: www.fujifilm.co.uk/synapse/technical/external>, (2004), 2 pgs.

"Fuji Receives Patent for Synapse's Subscription Technology", Fujifilm Medical Systems. [online]. [retrieved on Jul. 18, 2005]. Retrieved from the Internet: <URL: http://www.fujimed.com/company-info/press-room/doc/press_subscription_technology.asp?location=3&area=25&id=0&subid=0>, (2005), 2 pgs.

"Healthline Medical Imaging Modality Worklist DICOM Conformance Statement", Healthline Medical Imaging, (2005), 1-16.

"Healthline Medical Imaging Specification DICOM Conformance Statement", Healthline Medical Imaging, (2005), 27 pgs.

"HL7 Communications Module Definition Statement", Healthline Information Systems, Inc., (2005), 1-41.

"IDX® Imagecast tm Image Management—Radiology", [online]. (c) 1999-2005 IDX Systems Corporation. [retrieved on Jul. 15, 2005]. Retrieved from the Internet: <URL: www.idx.com/imagecast/ic_im_rad.asp>, (2005), 3 pgs.

"IHE Cardiology Technical Framework Supplement 2005—Displayable Reports (DRPT)", ACC/HIMSS/RSNA, (2005), 1-41.

"IHE Organization", IHE initiative: ACC/HIMSS/RSNA, [online]. [retrieved Nov. 30, 2005]. Retrieved from the Internet: <URL: http://www.ihe.net/About/Organization/org.cfm>, (2005), 3 pgs.

"Image Display Workstations", © 2004 Fujifilm UK. [online]. [retrieved on Nov. 28, 2005]. Retrieved from the Internet: <URL: www.fujifilm.co.uk/synapse/technical/display>, (2004), 2 pgs.

"Images Acquisitions System", © 2004 Fujifilm UK. [online]. [retrieved on Nov. 28, 2005]. Retrieved from the Internet: <URL: www.fujifilm.co.uk/synapse/technical/image>, (2004), 2 pgs.

"Images to any Desktop with Synapse", Fujifilm Medical Systems, Synapse Intelligent Connectivity, (2003), 2 pgs.

"Imaging on Call is a JCAHO Accredited Facility", © 2005 Imaging on Call LLC. [online]. [retrieved on Nov. 3, 2006]. Retrieved from the Internet: <URL: http://www.imagingoncall.net/company/jcaho.php>, (2005), 1 pg.

"Integrated Web Technology", © 2004 Fujifilm UK. [online]. [retrieved on Nov. 28, 2005] Retrieved from the Internet: <URL: www.fujifilm.co.uk/synapse/product/webtechnology>, (2004), 2 pgs.

"International Application Serial No. PCT/US05/43212, International Search Report dated Sep. 26, 2007", 2 pgs.

"International Application Serial No. PCT/US05/43212, Written Opinion dated Sep. 26, 2007", 4 pgs.

"Medical Licensure Services", [online]. [retrieved on Sep. 7, 2005]. Retrieved from the Internet: <URL: http://www.medlicense.comlservoces.htrnl>, (2005), 3 pgs.

"MedModel—The Industry Standard for Healthcare Simulations", [online]. [Retrieved on Sep. 7, 2005]. Retrieved from the Internet: <URL: http://www.promodel.com/products/medmodel>, (2005), 2 pgs.

"MedModel Simulation Plan your hospital and clinics using simulation software", Healthcare Planning Associates. [online]. [retrieved on Nov. 29, 2005]. Retrieved from the Internet: <URL: http://www.hpa.co.nz/index.asp?fpar=13732555342>, (2005), 2 pgs.

"Misys PACS Integration Module (PIM)", Misys Hospital Systems, Inc. [online]. Retrieved from the Internet: <URL: http://www.misyshealthcare.com/NR/rdonlyres/11B3E4E4-B08B-4A78-970E-D37B8869CCBF/0/misysPIMrev4.pdf#search=%22Misys%20PACS%20Integration%20Module%20(PIM)%22>, (2004), 2 pgs.

"Mobile Imaging", Empire Teleradiology Associates, LLC. [online]. [retrieved on Nov. 2, 2006]. Retrieved from the Internet: <URL: http://www.empiretelerad.com/emp_mobile.htm>, (2002), 1 pg.

"Multi-Site PACS with Synapse", © 2003 Fujifilm Medical Systems, Synapse Intelligent Connectivity, (2003), 2 pgs.

National Practitioner Data Bank Healthcare Integrity and Protection Data Bank, NPDB-HIPDB, [online]. [retrieved Jul. 18, 2005]. Retrieved from the Internet: <URL: http://www.npdb-hipdb.com/npdb.html>, (2005), 3 pgs.

"Network", (c) 2004 Fujifilm UK [online].]. [retrieved on Nov. 28, 2005]. Retrieved from the Internet: <URL: www.fujifilm.co.uk/synapse/technicaVnetwork>, (2004), 2 pgs.

"Night and Weekend Call Service", © RadLinx Group. [online]. [retrieved on Nov. 29, 2005]. Retrieved from the Internet: <URL: : http://www.radlinxgroup.com/nighthawk.html>, (2005), 3 pgs.

(56) References Cited

OTHER PUBLICATIONS

"Night Shift Radiology", Schematic of NightShift Radiology Network, NightShift Radiology. [online]. [retrieved on Nov. 28, 2005]. Retrieved from the Internet: <URL: http://www.nightshiftradiology.comlnetwork.htm>, (2005), 2 pgs.
"Nighthawk Pros Premier Night-Time Coverage—NightHawk Pros Company Profile, Teleradiology Overview of Services, Teleradiology Solutions for Radiology Experts, Teleradiology Technology Solutions", Nighthawk Pros. [online]. [retrived on Feb. 25, 2005]. Retrieved from the Internet: <URL: http://www.nighthawkpros.com/>, (2005), 4 pgs.
"Nighthawk Radiology Services Contact Information—contact information, company information, services, network technology", Nighthawk Radiology Services. [online]. [retrieved on Feb. 25, 2005]. Retrieved from the Internet: <URL: http://www.nighthawkrad.net/>, (2005), 5 pgs.
"NightRays credentialing", NightRays. [online]. Retrieved from the Internet: <URL: http://www.nightrays.comlcredreq.pdf>, (publsihed before Mar. 7, 2007), 1 pg.
"NightShift Radiology—Overview", NightShift Radiology. [online]. [retrieved on Feb. 25, 2005]. Retrieved from the Internet: <URL: http://www.nightshiftradiology.com/., (2005), 3 pgs.
"NightShift Radiology Preliminary Report, Sample Report", Nightshift Radiology, [online], [retrieved on Feb. 25, 2005]. Retrieved from the Internet: <URL: http://www.nightshiftradiology.com/sample_report.htm>, (2001), 6 pgs.
"Nightshift Radiology: Our Network Built for Reliability", Nightshift Radiology. [online]. [retrieved on Nov. 28, 2005]. Retrieved from the Internet: <URL: http://www.nightshiftradiology.com/network.htm>, (2005), 2 pgs.
"Non-Emergency Solve the Demand for Radiologists", (c) 2006 Diagna Radiology, [Online]. [retrieved Nov. 3, 2006]. Retrieved from the Internet: <URL: www.diagna.com/nonemerg.htm>, (2006), 2 pgs.
"On Demand Access to data", (c) 2004 Fujifilm UK. [online]. [retrieved on Nov. 28, 2005]. Retrieved from the Internet: <URL: www.fujifilm.co.uk/synapse/product/ondemand>, (2004), 2 pgs.
"OneApp Credentialing Software", (C) 2005 SyMed Development, Inc. [online], [retrieved on Sep. 7, 2005]. Retrieved from the Internet: <URL: http://www.symed.comlproducts/oneapp>, (2005), 2 pgs.
"OneApp Product Tour", (c) 2005 SyMed. [online]. [retrieved on Nov. 28, 2005]. Retrieved from the Internet: <URL: http://www.symed.comlproducts/oneapptour-l.asp>, (2005), 6 pgs.
"Partners you can trust", International Teleradiology Corporation. [online]. [retrieved on Nov. 3, 2006]. Retrieved from the Internet: <URL: http://www.teleradiologyonline.com/index.htm >, (2006), 1 pg.
"Product Data AON Tool Set Software Release Version 3.0", Fujifilm Medical Systems, (2003), 2 pgs.
"Product Data Server Software Release Version 3.0", Fujifilm Medical Systems, Synapse Intelligent Connectivity, (2003), 2 pgs.
"Project Title: Developing a Prototype for a Nationwide Health Information Network Architecture", Request for Proposal (RFP) ONCHIT-3, Section C—Descriptions/Specifications/Work Statement, (2010), 9 pgs.
"Proscan Reading Services tm—World Leaders in Medical Imaging Interpretation", Proscan® Reading Services. [online]. Retrieved from the Internet: <URL: http://www.proscan.comlfw/mainlfw_link.asp?URL=/ ... filelib/FileCabinet/PDF IProScanReadingService.pdfOlo3FFileName%3DProScanReadingService.pdf&Titie=Reading%20Services%20Brochur, (before Mar. 7, 2007), 9 pgs.
"Radiology PACS RadWorks 5.0 Standard", Wipro GE Healthcare. [online]. [retrieved on Jul. 15, 2005]. Retrieved from the Internet: <URL: www.gehealthcare.com/inen/it_solutions/rad_pacs/products/rad/msiisrwst2.html.html>, (2005), 3 pgs.
"Radiology PACS RadWorks 5.1 Standard", Wipro GE Healthcare. [online]. [retrieved on Jul. 15, 2005]. Retrieved from the Internet: <URL: www.gehealthcare.comlineniitsolutions/radpacs/products/radlradworks.html>, (2005), 2 pgs.

"Rapid Reliable Radiology Technology", StatRad. [online]. Retrieved from the Internet: <URL: http://statrad.com/technology.html>, (published before Mar. 7, 2007), 2 pgs.
"Rapid Response Radiology tm", Consulting Radiologists, Ltd, [online]. [retrieved on Nov. 3, 2006]. Retrieved from the Internet: <URL: http://www.consultingradiologists.com/rapidresponsetechnology.htrn >, (2006), 1 pg.
"RIS Radiology Information System Online Data Entry for Nighttime Teleradiology Studies", Virtual Radiologic Consultants, Startup Guide v1.7,, (May 16, 2005), 19 pgs.
"RSI Difference", (published prior to Nov. 10, 2010), 3 pgs.
"Santa Barbara County Care Data Exchange", [online]. Retrieved from the Internet: <URL: http://www.chcf.org/documents/ihealthJSantaBarbaraFSWeb.pdf>, (2007), 4 pgs.
"SkyRIS TeleRIS—Complete workftow, reporting and distribution solution for multi-contract radiology and teleradiology", ThinAir Data, (2004), 2 pgs.
"SkyRISE Enterprise—Enterprise speech recognition interfaced to existing HIS/RIS", ThinAir Data, (2004), 2 pgs.
"Software Solutions for Today's Healthcare Professionals", © 2006 Morrisey Associates. [online], [retrieved on Nov. 3, 2006]. Retrieved from the Internet: <URL: http://www.morriseyonline.coml >, (2006), 1 pg.
"Special Report: What's all the noise about tele-radiology?", © The RadLinx Group. [online]. [retrieved on Nov. 29, 2005]. Retrieved from the Internet: <URL: http://www.radlinxgroup.com/articie noise teleradiology.html>, (2005), 3 pgs.
"StatRAD—Rapid, Reliable Radiology", Welcome, About Us, Services, Jobs, Contact Stat Radiology. [online]. [retrieved on Feb. 25, 2005]. Retrieved from the Internet: <URL: http://statrad.com/index.html>, (2005), 9 pgs.
"Storage System", © 2004 Fujifilm UK. [online]. [retrieved on Nov. 28, 2005]. Retrieved from the Internet: <URL: www.fujifilm.co.ukJsynapse/technicaVstorage>, (2004), 2 pgs.
"Sy Med Simplifying Managed Care", © 2006 Sy.Med Development, Inc. [online]. [retrieved Nov. 3, 2008]. Retrieved from the Internet: <URL: http://www.symed.coml>, (2006), 1 pg.
"Synapse User's Manual Quick Reference Guide", Fujifilm Medical Systems. Software Version 3.0.0,2002, Fujifilm Medical Systems, (2002), 198 pgs.
"Synapse Version 3.0.0 Systems Administration Manual", Fujifilm, (2003), 1-55 pgs.
"Synapse™ Version 3.0.0 Workstation Administration Manual", Fujifilm, (2004), 1-62.
"TDS Network Welcome", Teleradiology Diagnostic Service. [online]. [retrieved on Oct. 27, 2006]. Retrieved from the Internet: <URL: http://www.tdsnetwork.neti>, (2004), 2 pgs.
"Technical Features", © 2004 Fujifilm UK. [online]. [retrieved on Nov. 28. 2005]. Retrieved from the Internet: <URL: http://www.fujifilrn.co.uk/synapse/technical>, (2004), 2 pgs.
"Technically, It's Important", © 2006 TeamHealth Radiology. [online]. Retrieved from the Internet: <URL: http://www.thteleradiology.comltechnology.htrn>, (2006), 3 pgs.
"Teleradiology Solutions about us, services, contact us", Teleradiology Solutions. [online]. [retrieved on Feb. 25, 2005]. Retrieved from the Internet: <URL: ttp://www.telradsol.com>, (2005), 4 pgs.
"Teleradiology: At Work Night and Day", Harris. [online]. [retrieved on Nov. 3, 2006]. Retrieved from the Internet: <URL: www.healthimaging.com/content/view/479/681>, (2006), 5 pgs.
"TeleShare", Dejarnette Research Systems. [online]. [retrieved on Sep. 7, 2005]. Retrieved from the Internet: <URL: http://www.dejarnette.com/1024/requestedpage.asp?Content=Products/>, (2004), 2 pgs.
"Templeton Radiology", Templeton Readings LLC. [online], [retrieved on Feb. 25, 2005]. Retrieved from the Internet: <URL: http://www.templetomadiology.com>, (2004), 9 pgs.
"Templeton Radiology Night Solutions", (c) 2004 Templeton Radiology. [online]. [retrieved on Nov. 29, 2005]. Retrieved from the Internet: <URL: http://www.templetomadiology.com/night_so1.htrn>, (2004), 2 pgs.

(56) References Cited

OTHER PUBLICATIONS

"Templeton Radiology Physician Credentialing", Templeton Radiology. [online]. [retrieved on Sep. 7, 2005], Retrieved from the Internet: <URL: http://www.templetomadialogy.com/pc.htrn>, (2005), 2 pgs.

"Templeton Radiology Radiology Services", Templeton Radiology. [online]. [retrieved on Nov. 29, 2005]. Retrieved from the Internet: <URL: http://www.idshealthcare.com/ hospital_management/global/templeton _radiology/web_enabled dictation! .. >, (2005), 3 pgs.

"Templeton Radiology RISIPACS website product information", © 2004 Templeton Radiology. [online]. [retrieved on Nov. 29, 2005]. Retrieved from the Internet: <URL: http://www.templetomadiology.com/pacs.htrn>, (2004), 2 pgs.

"Templeton Radiology RISIPACSIWEB/ARCHIVE managed solution", Templeton Radiology. [online]. [retrieved on Nov. 29, 2005]. Retrieved from the Internet: <URL: http://www.templetomadiology.com/pacs.htrn>,, (2005), 6 pgs.

"Templeton Radiology Teleradiology Night Solutions", Templeton Radiology. [online]. [retrieved on Nov. 29, 2005]. Retrieved from the Internet: <URL: http://www.idshealthcare.com/hospitat management/global/templeton radiology/templeton_mobile readings/.htrn>, (2005), 3 pgs.

"The Project", GlobalRad® Non-Profit Foundation. [online]. [retrieved on Nov. 3, 2006]. Retrieved from the Internet: <URL: http://www.globalrad.org/project.htm>, (2006), 1 pg.

"The RadLinx Group Ltd.—FAQ's", [online]. [retrieved on Nov. 11, 2005]. Retrieved from the Internet: <URL: http://www.radlinxgroup.com/faq.html>, (2005), 2 pgs.

"The Work Flow Process", Imaging on Call, LLC. [online]. [retrieved on Nov. 3, 2006]. Retrieved from the Internet: <URL: http://www.imagingoncall.net/technology/sat.php>, (2006), 1 pg.

"ThinAir Data—Healthcare at the Speed of Thought", [online]. [archived on Nov. 11, 2004]. Retrieved from the Internet: <URL: http://web.archive.org/web/20041112045011/http://www.thinairdata.com>, (2004), 2 pgs.

"U.S. Based Client Services", (c)RadLinx Group. [online]. [retrieved on Nov. 29, 2005]. Retrieved from the Internet: <URL: http://www.radlinxgroup.com/lc1ient.htrnl>, (2005), 2 pgs.

"US Radiology On-Call—Locations, Services, Technology, Radiologists, FAQ, Contact Us", [online]. [retrieved on Feb. 25, 2005]. Retrieved from the Internet: <URL: http://www.usroc.com/>, (2005), 7 pgs.

"US Radiology On-Call FAQ", US Radiology On-Call. [online]. [retrieved on Nov. 3, 2006]. Retrieved from the Internet: <URL: http://www.usroc.comlfaq.htrnl >, (2006), 2 pgs.

"US Radiology On-Call Radiologists", © US Radiology On-Call. [online]. [retrieved on Nov. 3, 2006]. Retrieved from the Internet: <URL: http://www.usroc.comlradiologists.htrnl >, (2006), 1 pg.

"US Radiology On-Call—Locations, Services, Technology, Radiologists, FAQ, Contact Us", US Radiology. [online]. [retrieved on Feb. 25, 2005]. Retrieved from the Internet: <URL: http://www.usroc.coml >, (2005), 7 pgs.

"Veritas Product data (V-FORM)", Veritas Medical Services, Inc. [online], [retrieved on Sep. 7, 2005]. Retrieved from the Internet: <URL: http://www.veritasmed.comlproducts/>, (2005), 3 pgs.

"Virtual Radiologic tm Physician Services Operating Manual", Virtual Radiologic Consultants, Inc., (2005), 75 pgs.

"Vistar Technologies—Automated Credentialing Software CVOs and Medical Societies", (c) 2005 Vistar Technologies. [online]. [retrieved on Nov. 3, 2006]. Retrieved from the Internet: <URL: http://vistartech.comlcvomed.htrn >, (2005), 1 pg.

"Visual Cactus", Cactus Software. [online]. Retrieved from the Internet: <URL: http://www.visualcactus.com/Public2002/images/HospitalFlyer-2005.pdf.>,, (2005), 1 pg.

"VRN—A Step Beyond Teleradiology", (c) 2005 NeuroStar Solutions. [online], [retrieved on Nov. 30, 2005]. Retrieved from the Internet: <URL: http://www.neurostarsolutions.com/cms/theVRN/vrnApplicationServices/pacs.html>, (2005), 2 pgs.

"Welcome to MedTel International", MedTel International. [online]. [retrieved on Nov. 3, 2006]. Retrieved from the Internet: <URL: http://www.medtel.coml >, (2006), 1 pg.

"Why the NPDB Was Created", National Practioner Data Bank. [online], [retrieved on Nov. 30, 2005]. Retrieved from the Internet: <URL: http://www.npdb-hipdb.comlnpdb.htrnl>, (2005), 2 pgs.

"WIN/Staff Pro-File", WIN/Staff 002. [online]. [retrieved on Nov. 3, 2006]. Retrieved from the Internet: <URL: http://www.winstaff.comlmarketing/prac J>ro file.htrn >, (2002), 1 pg.

"World Wide Rad FAQ", World Wide Rad [online]. [retrieved on Nov. 3, 2006]. Retrieved from the Internet: <URL: http://www.worldwiderad.comlWWRWebsite files/frame.htrn >, (2006), 1 pg.

Batchelor, J. S., "Remote-controlled MRI tackles tech shortage", [online]. [retrieved on Jan. 26, 2006]. Retrieved from the Internet: <URL: http://www.auntrninnie.comlindex.asp?sec=ser&sub=def&pag=dis&ItemID=69371>, (2006), 2 pgs.

Brice, James, "Continued IT evolution boosts teleradiology", NightHawl Radiology Services, (Feb. 2004), 5 pgs.

Collins, J E, et al., "Automated Assignment and Scheduling of Service Personnel", IEEE Expert, (Apr. 1994), 33-39.

Harrell, Charles R., et al., "Healthcare Simulation Modeling and Optimization using MeclModel", Proceedings of the 2000 Winter Simulation Conference, 2000, Joines et al., eds., (2000), 203-207.

Khan, Rashid N., *Business Process Management: A Practical Guide*, (Sep. 2004), 103-124.

Khan, Rashid N., *Business Process Management: A Practical Guide*, (Sep. 2004), p. 179.

Khan, Rashid N., *Business Process Management: A Practical Guide*, (Sep. 2004), 207-222.

Khan, Rashid N.., "Smart Ways of Routing Work, Business Process Management: A Practical Guide", [online]. Retrieved from the Internet: <URL: http://www.bpm.com/smart-ways-of-routing-work.html>, (Sep. 2004), 4 pgs.

May, T., "Home work may solve doc shortage", [online]. [retrieved on Jan. 22, 2007]. Retrieved from the Internet: <URL: www.usrp.net/articles/Home work.htrnl>, (2007), 2 pgs.

Page, D., "To the ends of the Earth", Diagnostic Imaging, [online]. [retrieved on Feb. 25, 2005]. Retrieved from the Internet: <URL: www.diagnosticimaging.comlspecialedition2003l?page=teleradiology.htrnl >, (2003), 7 pgs.

SKYRIS, "Full feature RIS with integrated speech recognition and transcription", ThinAir Data, (2004), 2 pgs.

ThinAir Data, Skyris Teleradiology, "TeleRIS is the complete teleradiology, multi-contract, multi-facility workftow, reporting and distribution solution", [online]. (c) ThinAir Data Corp. (archived on Feb. 4, 2005]. Retrieved from the Internet: <URL: http://web.archive.org/web/20050204055213/ www.thinairdata.com/SkyRISTele.htm, (2005), 3 pgs.

"U.S. Appl. No. 12/856,096, Notice of Allowance dated Jan. 25, 2012", 14 pgs.

"U.S. Appl. No. 12/856,096, PTO Response to 312 Amendment dated Feb. 27, 2012", 2 pgs.

"U.S. Appl. No. 12/942,355, Notice of Allowance dated Apr. 12, 2012", 16 pgs.

"U.S. Appl. No. 13/333,767, Notice of Allowance dated Aug. 22, 2013", 12 pgs.

"U.S. Appl. No. 13/333,767, Response filed Jul. 18, 2013 to Non Final Office Action dated Mar. 20, 2013", 15 pgs.

"U.S. Appl. No. 13/423,513, Notice of Allowance dated Aug. 20, 2013", 11 pgs.

"U.S. Appl. No. 13/423,513, Response filed Jul. 18, 2013 to Non Final Office Action dated Mar. 19, 2013", 16 pgs.

"U.S. Appl. No. 13/423,513, Supplemental Notice of Allowability dated Oct. 10, 2013", 5 pgs.

"U.S. Appl. No. 13/449,004, Notice of Allowance dated Apr. 22, 2013", 13 pgs.

"U.S. Appl. No. 90/009,889, Reexam Petition Decision dated Aug. 1, 2012", 15 pgs.

"Canadian Application Serial No. 2,636,705, Office Action dated Mar. 12, 2014", 3 pgs.

"Defendants' Supplemental Prior Art Statement dated Apr. 11, 2014", *Virtual Radiologic Corporation, et al. v. Tandem Radiology,*

(56) References Cited

OTHER PUBLICATIONS

LLC, et al., (Civil Action No. 2:13-cv-01705-DKD, United States District Court for the District of Arizona), 27 pgs.

"Ex. A—Defendant Tandem Radiology's proposed Prior Art Contentions Chart for U.S. Pat. No. 8,195,481", (Apr. 11, 2014), 140 pgs.

"Ex. B—Defendant Tandem Radiology's proposed Prior Art Contentions Chart for U.S. Pat. No. 7,970,634", (Apr. 11, 2014), 182 pgs.

"Ex. C—Defendant Tandem Radiology's proposed Prior Art Contentions Chart for U.S. Pat. No. 8,145,503", (Apr. 11, 2014), 285 pgs.

"Ex. D—Defendant Tandem Radiology's proposed Prior Art Contentions Chart for U.S. Pat. No. 8,090,593", (Apr. 11, 2014), 132 pgs.

"Ex. E—Defendant Tandem Radiology's proposed Prior Art Contentions Chart for U.S. Pat. No. 8,515,778", (Apr. 11, 2014), 115 pgs.

"International Application Serial No. PCT/US2011/059926, International Preliminary Report on Patentability dated May 23, 2013", 12 pgs.

"International Application Serial No. PCT/US2011/059926, Search Report dated Mar. 1, 2012", 2 pgs.

"International Application Serial No. PCT/US2011/059926, Written Opinion dated Mar. 1, 2012", 10 pgs.

"MGRIS—Global Radiology Information System", Medweb®, (before Nov. 2013), 1 pg.

"RIS Logic Module Workflow Functionality Highlights", [online]. [archived on Jan. 5, 2004]. Retrieved from the Internet: <URL: http://web.archive.org/web/20040105160056/http://www.merge.com/products/pacsteleradiologyweb/rislogiccs_features.asp>, (2004), 6 pgs.

"State Telemedicine Licensure as of Jul. 15, 2001", [oline]. © 1994-2002 American College of Radiology. [archived on Sep. 17, 2002]. Retrieved from the Internet: <URL: http://web.archive.org/web/20020917202928/http://www.acr.org/cgi-bin/fr?mast:mastheaddepartments,text:/departments/govt_rel/text.html>, (Revised Feb. 2002), 7 pgs.

"ThinAir Data", Promotional Material, (before Nov: 2013), 2 pgs.

"ThinAir Data—SkyRIS DR—Bringing Speech, Wireless & Internet Technologies to Healthcare", [online]. [archived on Jun. 7, 2001]. Retrieved from the Internet: <URL: http://web.archive.org/web/20010607094324/http://thinairdata.com/SkyRIS/DR/dr.html>, (2001), 1 pg.

"ThinAir Data—SkyRIS—Speech, Wireless and the Internet—Healthcare at the speed of thought", (before Nov. 2013), 2 pgs.

"ThinAir Data—SkyRIS Teleradiology—Speech, Wireless and the Internet—Healthcare at the speed of thought", (before Nov. 2013), 2 pgs.

"ThinAir Data—SkyRIS TeleRIS—Speech, Wireless and the Internet—Healthcare at the speed of thought", (before Nov. 2013), 2 pgs.

Berger, S. B., et al., "Medical-Legal Issues in Teleradiology", *AJR. 166*, (1996), 505-510.

Brice, James, "Globalization comes to radiology", [online]. © 1996-2004 CMP Media LLC. [retrieved on May 22, 2014]. Retrieved from the Internet: <URL: http://web.mit.edu/outsourcing/class1/DI-radiology-1.htm>, (Nov. 2003), 7 pgs.

Chacko, Anna K., et al., "Vision and benefits of a virtual radiology environment for the U.S. Army", (Abstract), *Proc. SPIE 3339, Medical Imaging 1998: PACS Design and Evaluation: Engineering and Clinical Issues*, 200. (1998), 2 pgs.

Finarelli, Hugo J, et al., "Effective demand forecasting in 9 steps Shifts in demand for a hospital's services can occur unexpectedly. Demand forecasting can help you prepare for these shifts and avoid strategic missteps", [online]. [retrieved on Feb. 22, 2012]. Retrieved from the Internet: http://findarticles.com/p/articles/mi_m3257/is_11_58/ai_n635908/, (Nov. 2004), 13 pgs.

Kalyanpur, Arjun, et al., "Implementation of an International Teleradiology Staffing Model", *Radiology*, 232(2), (Aug. 2004), 415-419.

Martinez, Ralph, et al., "Virtual Management of Radiology Examinations in the Virtual Radiology Environment Using Common Object Request Broker Architecture Services", *Journal of Digital Imaging*, 12(2)(Suppl. 1), (1999), 181-185.

Mun, Seong G., et al., "Teleradiology and emerging business models", *J. Telemed. Telecare*, 11(6), (2005), 271-275.

Osborne, J. W., et al., "The Power of Outliers (and why researchers should Always check for them)", *Practical Assessment, Research & Evaluation*, 9(6), (Nov. 2004), 28 pgs.

Siegel, Eliot, et al., "Work Flow Redesign: The Key to Success When Using PACS", *AJR*, 178, (Mar. 2002), 563-566.

"U.S. Appl. No. 14/079,284, Final Office Action dated Aug. 4, 2015", 18 pgs.

"U.S. Appl. No. 14/079,284, Non Final Office Action dated Jan. 15, 2015", 13 pgs.

"U.S. Appl. No. 14/079,284, Response filed Jun. 15, 2015 to Non Final Office Action dated Jan. 15, 2015", 15 pgs.

"U.S. Appl. No. 14/079,307, Final Office Action dated Aug. 4, 2015", 16 pgs.

"U.S. Appl. No. 14/079,307, Non Final Office Action dated Jan. 22, 2015", 12 pgs.

"U.S. Appl. No. 14/079,307, Response filed Jun. 22, 2015 to Non Final Office Action dated Jan. 22, 2015", 15 pgs.

"U.S. Appl. No. 90/009,889, Decision on Petition dated Aug. 1, 2012", 15 pgs.

"Canadian Application Serial No. 2,636,705, Office Action dated Mar. 26, 2015", 5 pgs.

"U.S. Appl. No. 14/079,284, Non Final Office Action dated Feb. 5, 2016", 26 pgs.

"U.S. Appl. No. 14/079,284, Response filed Jan. 4, 2016 to Final Office Action dated Aug. 4, 2015", 24 pgs.

"U.S. Appl. No. 14/079,307, Non Final Office Action dated Feb. 8, 2016", 23 pgs.

"U.S. Appl. No. 14/079,307, Response filed Jan. 4, 2016 to Final Office Action dated Aug. 4, 2015", 25 pgs.

"Canadian Application Serial No. 2,636,705, Response filed Sep. 28, 2015 to Office Action dated Mar. 26, 2015", 11 pgs.

"U.S. Appl. No. 14/079,284, Appeal Brief mailed Nov. 9, 2016", 30 pgs.

"U.S. Appl. No. 14/079,284, Appeal Decision mailed Dec. 25, 2018", 27 pgs.

"U.S. Appl. No. 14/079,284, Final Office Action dated Jun. 9, 2016", 28 pgs.

"U.S. Appl. No. 14/079,284, Response filed May 4, 2016 to Non Final Office Action dated Feb. 5, 2016", 22 pgs.

"U.S. Appl. No. 14/079,307, Appeal Brief filed Aug. 9, 2016", 24 pgs.

"U.S. Appl. No. 14/079,307, Appeal Decision mailed Jun. 25, 2018", 23 pgs.

"U.S. Appl. No. 14/079,307, Examiner Interview Summary dated Jan. 31, 2019", 3 pgs.

"U.S. Appl. No. 14/079,307, Non Final Office Action dated Oct. 9, 2018", 20 pgs.

"U.S. Appl. No. 14/079,307, Response filed Feb. 8, 2019 to Non Final Office Action dated Oct. 9, 2018", 17 pgs.

"Canadian Application Serial No. 2,636,705, Final Office Action dated Apr. 4, 2016", 5 pgs.

"Canadian Application Serial No. 2,636,705, Office Action dated May 10, 2017", 2 pgs.

"Canadian Application Serial No. 2,636,705, Response Filed Jun. 28, 2017 to Office Action dated May 10, 2017", 1 pg.

"Canadian Application Serial No. 2,636,705, Response filed Oct. 4, 2016 to Final Office Action dated Apr. 4, 2016", 6 pgs.

"U.S. Appl. No. 14/079,284, Response to Final Office Action dated Jun. 9, 2016 filed Feb. 25, 2019", 16 pgs.

"U.S. Appl. No. 14/079,307, Notice of Allowance dated Mar. 28, 2019", 9 pgs.

"Canadian Application Serial No. 2,636,705, Summons to attend Oral Proceedings mailed Mar. 15, 2019", 8 pgs.

"U.S. Appl. No. 14/079,284, Non Final Office Action dated May 20, 2019", 18 pgs.

(56) References Cited

OTHER PUBLICATIONS

"U.S. Appl. No. 14/079,284, Examiner Interview Summary dated Jun. 3, 2019", 3 pgs.

* cited by examiner

| | | | Registry | | |
|---|---|---|---|---|---|
| 600 | 602 | 604 | 606 | 608 | 610 |
| Patient ID | Facility Network Address | Medical Facility ID | System Requirements | Modification Dates | Secondary Registry Address |
| 987654321 | 69.54.44.255 | 123456789 | Raw DICOM | 11/02/05; 10/10/04 | 66.22.126.110 |
| | | Mercy Hospital | | | |

TELERADIOLOGY IMAGE PROCESSING SYSTEM

CROSS REFERENCE TO RELATED CASES

This application is a continuation of and claims priority under 35 U.S.C. § 120 to U.S. patent application Ser. No. 13/449,004, entitled "TELERADIOLOGY IMAGE PROCESSING SYSTEM," filed on Apr. 17, 2012, which is a continuation of and claims priority under 35 U.S.C. § 120 to U.S. patent application Ser. No. 12/870,271, entitled "TELERADIOLOGY IMAGE PROCESSING SYSTEM," filed on Aug. 27, 2010, which is a continuation-in-part of prior U.S. patent application Ser. No. 12/783,073 filed May 19, 2010 and entitled "Multiple Resource Planning System", which is a continuation of prior U.S. patent application Ser. No. 11/288,645 filed Nov. 28, 2005 and entitled "Multiple Resource Planning System", which claims the benefit of U.S. Provisional Patent Application Nos. 60/656,215, filed Feb. 25, 2005 by Backhaus and entitled "Automated Credentialing and Licensing System"; 60/682,052, filed May 17, 2005, by Backhaus et al. and entitled "Integrated Caching Environment with Order Form Pre-population"; 60/694,880, filed Jun. 29, 2005, by Backhaus et al., and entitled "Medical Data Management Method and System"; 60/699,119, filed Jul. 14, 2005, by Backhaus et al., and entitled "Medical Data Transfer System and Method"; 60/740,454, filed Nov. 28, 2005 by Backhaus et al., and entitled "Medical Data Transfer System and Method"; 60/740,589, filed Nov. 28, 2005 by Casey and entitled "Remote Scanning System and Method"; and 60/740,527, filed Nov. 28, 2005 by Casey and entitled "Patient Information Translation Method and System"; the entirety of all of the preceding applications are incorporated herein by reference.

FIELD OF THE INVENTION

The present invention generally relates to the processing of medical images and related data. The present invention more specifically relates to a radiology processing system, such as a teleradiology image order management system, configured for providing features in connection with a radiology workflow.

BACKGROUND OF THE INVENTION

Medical images generated by an imaging modality, such as X-rays, CAT (computerized axial tomography) scans, and MRI's (Magnetic Resonance Imaging), are commonly digitized to facilitate reading by doctors at remote locations. In use, hospitals and other healthcare providers commonly use systems to capture and digitize the medical images. The medical images are typically transmitted from the modality to a remote image server such as a Picture Archiving and Communications System (PACS). This transmission may occur over a network, such as an intranet or the Internet.

Additionally, the hospital may also transmit orders corresponding to the images to an order server, such as a Radiologist Information System (RIS). Orders are used to request a doctor to interpret, or read, the images and return a diagnostic report. Orders may also contain additional information related to the image or the patient, such as a patient identifier, the procedure type associated with the image, patient demographic information, and a hospital identifier. Thus, orders may be submitted by hospitals and healthcare providers to identify the patient and instruct the radiologist to provide information for a specific medical condition.

BRIEF SUMMARY OF THE INVENTION

Processing systems used in radiological practices generally route images and orders to doctors in a fixed manner. For example, all of the images and orders may be transmitted from the scanning area of a hospital to a set of doctors that work in the radiology department of the same hospital. The doctors may be at the hospital or access the images with remote systems.

In teleradiology settings, the radiologist analyzes the image at a remote location and returns the diagnostic report. The diagnostic report may be transmitted through the network to the order server (the teleradiology RIS), which in turn may forward the report to the hospital or other medical facility that originally transmitted the order and images corresponding to the report. In contrast, in hospital radiology settings, the image and order systems are typically internal to the hospital. For example, an emergency center may scan a patient, digitize the images, and transmit them to an image server (e.g., a PACS) at the hospital. Likewise, the emergency center may enter an order that is sent to an order server at the hospital using an internal RIS. Both the images and orders may then be transmitted to a radiology department, which is located at the hospital. As is evident, much more complexity exists for the assignment, transfer, and review of radiology orders and data in teleradiology or remote viewing settings.

One aspect of the present invention relates to the integration and operation of a radiology processing system, including the various aspects of data transferred between various parties and locations in a teleradiology setting. In one embodiment, a set of components within the radiology processing system interact with each other to place and process radiology studies and study-associated data. The operation of these components further effect an enhanced workflow of the radiology studies and the radiology read orders and images associated therewith, particularly in a teleradiology setting where a remote radiologist is selected from a pool of eligible radiologists. The radiology processing system acts to process relevant information from the radiology study and assign the radiology study to the remote radiologist with a defined workflow. Other activities related to the teleradiology read, such as medical facility billing, radiologist compensation, data processing, and radiology study forecasting may be further facilitated within the teleradiology processing system through the collection and processing of data.

In one specific embodiment disclosed herein, a radiology image processing system contains components, modules, or other similar processing structures and hardware to facilitate image processing; order processing; data processing; and a teleradiology workflow. The image processing component may be configured to digitally store, transmit, and facilitate the display of a plurality of digital radiology images received from one or more medical facilities, each of the plurality of digital radiology images being part of a radiology study derived from one or more radiology scan procedures. The order processing component may be configured to process and transmit radiology read orders received from the one or more medical facilities, the radiology read orders corresponding to the plurality of digital radiology images within a radiology study.

The data component may be configured to collect data from the plurality of digital radiology images received at the image processing component and the orders received with the order processing component, in addition to defining and implementing rules for the examination of the radiology study. In combination with the data component, a workflow component may be configured to assign the orders and the plurality of digital radiology images to a qualified member of a pool of remote radiologists for review. The workflow component may also factor licensing and credentialing qualifications, and medical facility or teleradiology service provider preferences when assigning the orders and the images to the qualified member.

Further components within the radiology image processing system may include: a billing component configured to facilitate billing of radiology services with the one or more medical facilities (whose operation may further be customized based on content within the plurality of digital radiology images); a forecasting component configured to estimate levels of adequate radiologist staffing for future radiology reads; a compensation component configured to track compensation for radiologist activities; an access control component configured to provide security and restrict access to defined functions within the system; enhanced features of the data processing component to interface with medical record and radiology information systems; and enhanced features of the image processing component to convert radiology image data into a variety of digital image formats and/or transmit image data to defined digital locations.

Other specific embodiments disclosed herein include methods for processing radiology images using a teleradiology workflow in accordance with the techniques described herein; and computer program products configured for processing radiology images in a teleradiology workflow, with the computer program product comprising a computer readable storage medium having computer readable code embodied therewith, each of these computer program products executable on computing hardware and machines to implement the techniques described herein.

BRIEF DESCRIPTION OF THE DRAWINGS

FIG. 6 illustrates a diagram of a patient information registry according to an embodiment of the present invention;

DETAILED DESCRIPTION OF THE INVENTION

One of the aspects of the present invention disclosed herein includes the configuration and interaction of a plurality of operating components within a teleradiology processing system. Within the processing system, the operating components interact with each other to place and process teleradiology orders and facilitate reads of radiological images. The configuration and interactions between the operating components provides notable efficiencies, and enable a dynamic workflow for the review of radiology image studies. Further, the data processing which occurs within the processing system allows the customization and enforcement of rules covering radiologist compensation, forecasting, and assignment of teleradiology orders.

Figure 1:
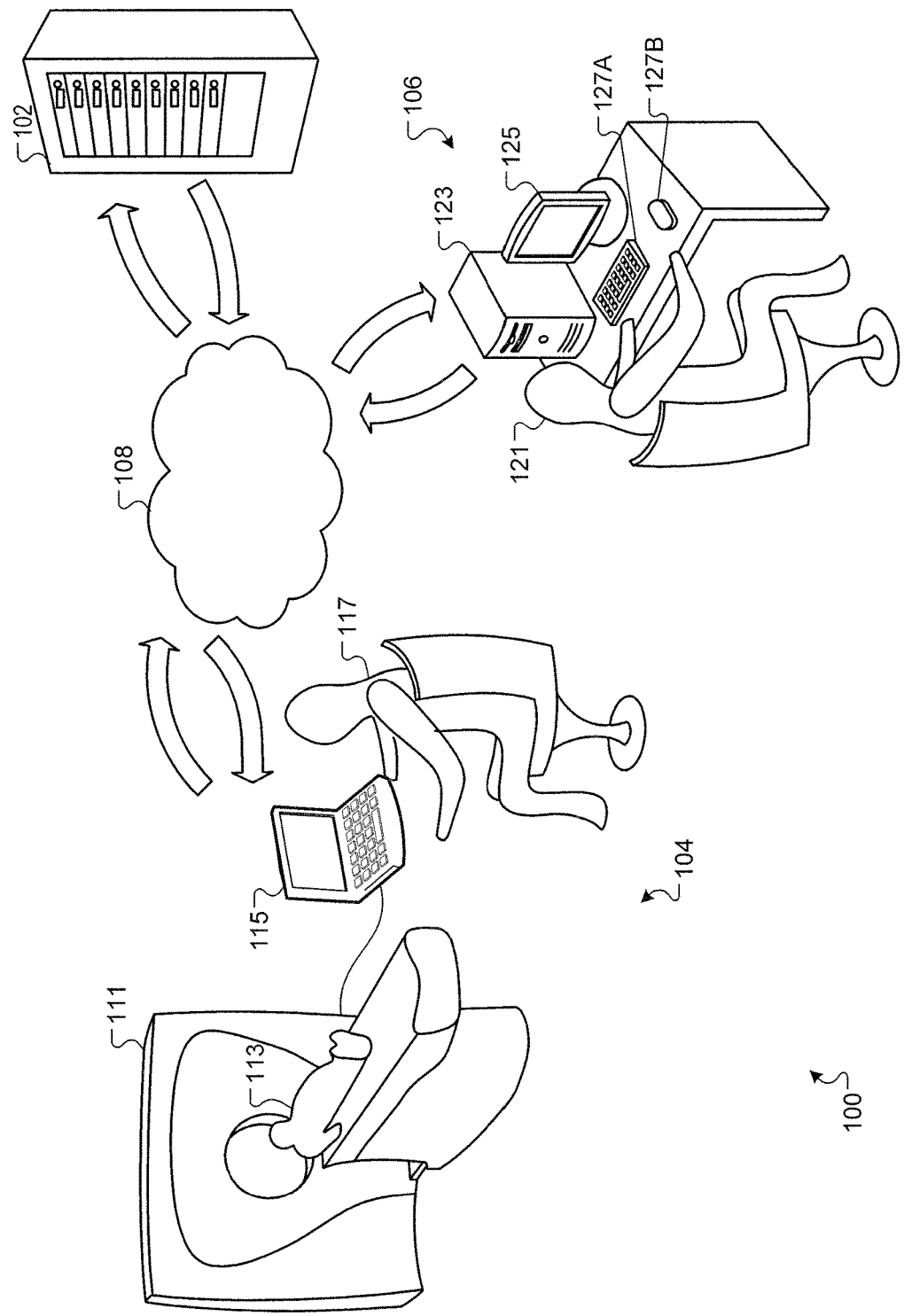
FIG. 1 provides an illustration of a teleradiology system used in conjunction with an embodiment of the present invention.

Referring to FIG. 1, an operating configuration of an example teleradiology system 100 is illustrated. The system 100 can be used for capturing medical image data in one location and for reviewing medical images associated with the data in another location. The system 100 may include many geographically separated imaging devices and many image review terminals. As further described herein, system 100 might be configured to operate as a remote teleradiology system connected to a plurality of healthcare locations, or alternatively system 100 may be configured to a generally localized radiology system used in a single hospital, healthcare provider network, or private radiology practice.

For purposes of illustration, the teleradiology system 100 illustrated in FIG. 1 includes an imaging system at a medical facility 104, an image order (IO) management system 102, and an image review system 106. The imaging system at the medical facility 104, for example, may include an imaging device 111, such as a CT (computer tomography) scanner, an MRI (magnetic resonance imaging) scanner, or another imaging modality. Using an energy source such as x-rays or magnetic fields, for example, the imaging device 111 may capture image data associated with a subject 113 (e.g., a patient).

The imaging device 111 may be controlled by a radiology technician 117 through the use of a workstation terminal or other electronic control 115. Prior to the radiology technician 117 conducting the scan of a patient, information is entered into the terminal 115. In most medical devices, this information must be manually entered via an input device (such as a keyboard or bar-code reader) operably coupled to the terminal 115. This information is then placed within the image itself. For example, the imaging device 111 may produce radiological images generally consistent with the DICOM format, other industry-accepted standards, or proprietary standards.

Consistent with the appropriate image format, the images produced by the image data source may include metadata. This metadata may be generated by the imaging device 111 and/or by the technician input collected by the terminal 115. Further, the series of images may be obtained directly by the imaging device 111 in the facility shown in FIG. 1, or may be transferred in whole or in part from another image capturing device connected to the imaging device modality 111 or the facility's local network. The imaging data source may also be transmitted through use of a local facility imaging server (not shown), such as a Digital Imaging and Communications in Medicine (DICOM) server or other PACS.

The metadata within each imaging data file or DICOM data transmission may include identification information such as patient identifier and an identifier of the series of images, in addition to information about the type of modality and the techniques used to obtain the images. Further, for images formatted according to the DICOM standard, data fields such as a unique image identifier, a unique study identifier, the patient's name, and the facility from which the image originates may be included within the metadata.

The image data generated by the imaging device 111 may include a series of two-dimensional images. In some implementations, the image data may be used to produce a three-dimensional model that can be further manipulated and reformatted for generating two-dimensional (or three-dimensional) images. Image data captured by the imaging device 111 may be stored and processed by the IO Management System 102 or another imaging device server (e.g., one or more computers with a processor and a memory), and may be provided to other systems and computers in the system 100 through network 108 (e.g., an intranet or the Internet).

In some implementations, image data provided to the IO Management System 102 results in data being stored and processed by one or more computers. For example, the IO Management System 102 may determine that the image data is to be forwarded to a system user 121 (e.g., a radiologist) at an image review system 106. As shown, image data may be provided by the IO Management System 102 to the image review system 106 through the network 108.

The image review system 106, for example, may include an image display server 123 (e.g., one or more computers with a processor and a memory), a display device 125 (e.g., a monitor), and input devices 127A-B (e.g., keyboards, computer mice, joysticks, touch interfaces, voice recognition interfaces, and the like). In some implementations, image data may be processed by the image display server 123 and visually presented to the user 121 as one or more images at the display device 125. Using the input devices 127A-B, the user 121 may interact with the presented images, for example, by manipulating one or more user controls included in a graphical user interface presented at the display device 125 in association with the images. For example, the user 121 may view an image (or a series of related images), and may specify one or more image adjustments, such as zooming, panning, rotating, changing contrast, changing color, changing view angle, changing view depth, changing rendering or reconstruction technique, and the like. By viewing and interacting with presented image data and with the user interface, for example, the user 121 may produce and indicate a diagnostic finding related to the subject 113.

When the IO Management System 102 receives the image, it may process the image with an image server component. This processing may include compressing or converting the image to a different format using a compressor/converter module. This image server may also operate to extract metadata from each image file in a series of radiology scan images. For example, the extracted metadata may include header data for the image providing patient information and hospital information for the hospital that sent the image. The image server may then store all or part of the extracted information in a study record that may be correlated with appropriate orders and studies.

Figure 2A:
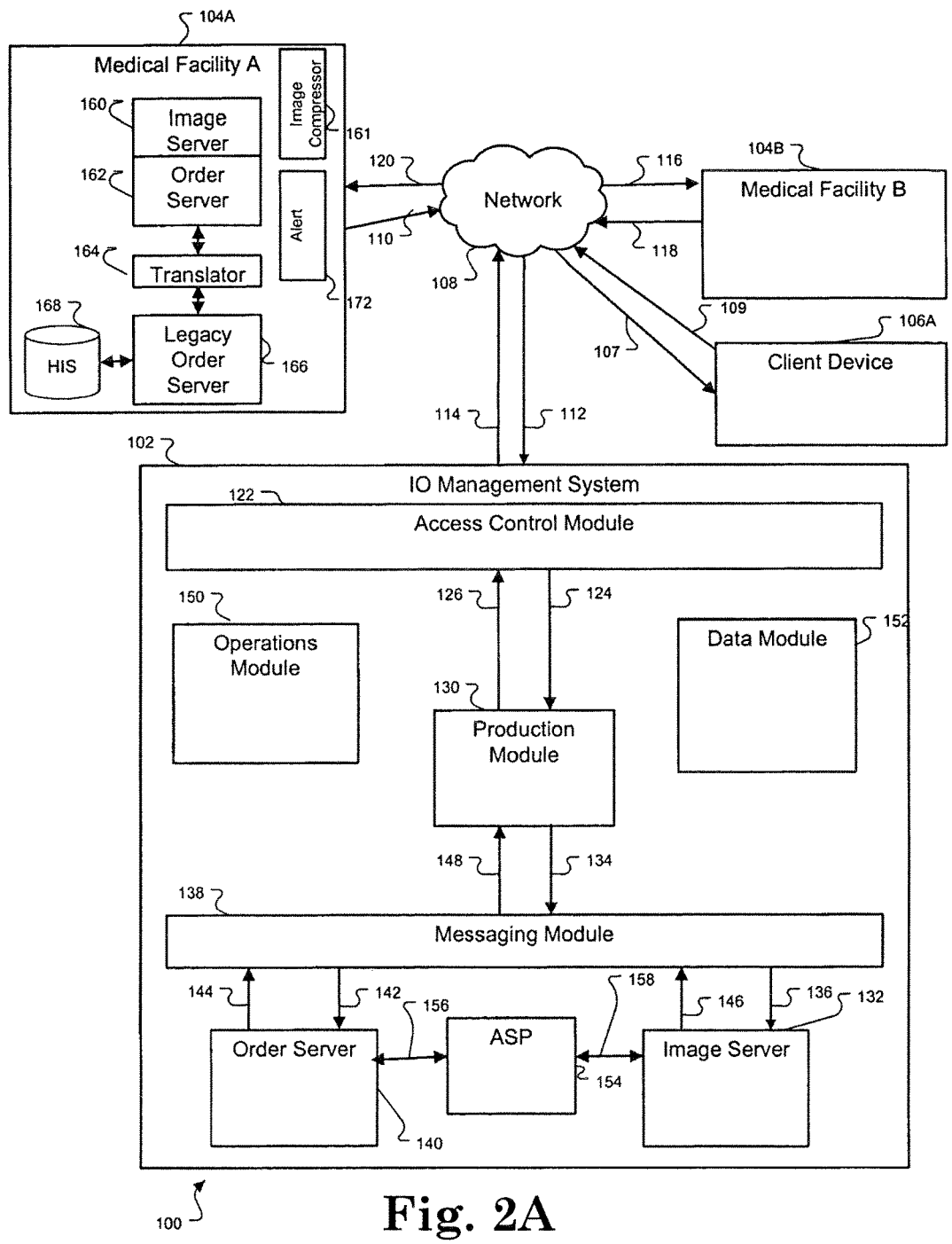
FIG. 2A illustrates a block diagram of a teleradiology system configured to communicate medical information among medical facilities and client devices according to an embodiment of the present invention.

FIG. 2A is a block diagram of a system that communicates medical information among medical facilities and client devices according to one embodiment of the present invention. More specifically, FIG. 2A shows the teleradiology system 100 including an image order (IO) Management System 102, medical facilities 104, and client devices 106 connected by a network 108, such as the Internet. The medical facilities 104 may send images and orders for studying the images to the IO Management System 102, as represented by arrows 110, 118, and 112. The images may include representations of body parts generated by imaging modalities such as x-rays, CAT scans, and MRIs.

The images may also contain information, such as the medical facility 104A that sent the image, the number of images in the transmission, the patient name, and other patient demographic information. The orders may contain information about a patient, such as name, medical history, and the reason the image was taken. The order may also include a description of an associated image, such as a pelvic abdominal scan, a number of images associated with the order, and an order type, such as preliminary or final read. The presence of the patient name and other patient information may enable a particular image to be linked with a particular order.

The IO Management System 102 may store the images and orders and assign the orders to appropriate users at the client devices 106. For example, the IO Management System 102 may assign an order from a medical facility 104A to a radiologist at a client device 106A. If the radiologist accepts the order, the IO Management System 102 makes the images associated with the order available to the radiologist for viewing, as indicated by arrows 114 and 107. The radiologist can interpret the images and send a report back to the IO Management System 102, as represented by arrows 109 and 112. The IO Management System 102 then forwards the report to the originating medical facility, as indicated by arrows 114 and 120, where the report is used in a diagnosis for the patient.

The IO Management System 102 may be implemented on a single computing device or on multiple computing devices, such as a server farm. In one implementation, the IO Management System 102 is disbursed over several servers that are connected through a network 108. This configuration may be advantageous by permitting easy expansion of the system and flexibility in managing the flow of received and output images and orders.

Medical facilities may send images and orders at the same time as one another or at different times. Images, orders, and reports may be sent over the same network or different networks. For example, the IO Management System 102 may receive images and orders through a single T1 connection to the Internet, or the images may be received from the Internet through a T1 connection and the orders may be received through a modem connection. In another example, the IO Management System 102 receives an image and an order from a medical facility over the Internet and return a corresponding report to the medical facility over a fax connection.

Additionally, the images and orders may be sent separately or combined in one transmission. For instance, a computing device at a medical facility may use software that sends the orders and the images with a single application and single set of actions, or the medical facility may send the images using one application that sends one transmission and send the orders using a different application that sends a separate transmission.

The network 108 over which the images and orders are sent from the medical facilities 104 to the IO Management System 102 may be a secure network, such as a virtual private network (VPN). The VPN may include a secure computing device, or terminal, at the medical facility, encrypted transmissions sent through the network 108, and a secure computing device at the remote technician system 104. The transmission of encrypted scanning information, requests, and commands may also include the use of the Secure Socket Layer (SSL) communications. In this implementation, the medical facility 102 may have a public key, which is issued by the remote technician system 104. The public key may be used to encrypt communications transmitted to the system 104, and the remote technician system 104 may then use a private key to decrypt the transmitted communication. In another implementation, a remote desktop application, such as the Citrix application produced by Citrix Systems, Inc., of Fort Lauderdale, Fla., may be used. For example, the medical facility 102 may have a Citrix server installed in a console server. A Citrix client installed at the remote technician system 104 can communicate with the Citrix server using encrypted messages, such as RSA encrypted messages.

In the IO Management System 102 there may be an Access Control Module 122 that controls users' access to the IO Management System 102. Users may include staff at a hospital, imaging center, medical research facility or other medical facility and radiologists at the client devices 106. For example, the Access Control Module 122 may include a remote desktop application, such as Terminal Services, that allows users to login to the IO Management System 102. In another example, the Access Control Module 122 may include an application portal accessible from the remote desktop or from the Internet with individual logins and passwords for each user. If the Access Control Module 122 grants access to a user at the medical facility 104A, the user sends images and orders or receives reports, as indicated by arrows 124 and 126, respectively. If an order is assigned to and accepted by a radiologist at the client device 106A, the radiologist retrieves the order and its images or sends a report.

The Access Control Module 122 may also monitor the connectivity status of the medical facilities 104 or the client devices 106. For example, control module 122 may monitor whether a secure network connection between the medical facilities or the client devices and the IO Management System 102 is operational.

Additionally, the Access Control Module 122 may monitor and log information, such as which users access the system, for how long, what applications are accessed, what type of data is transferred, and how much data is transferred to the user. This information is stored in the Data Module 152 and may be used for purposes of billing and compensation discussed below.

When an image is received by the IO Management System 102 and accepted by the Access Control Module 122 it may be sent to a Production Module 130. The Production Module 130 may handle real-time processing in the IO Management System 102, such as managing the workflow of orders and images. The Production Module 130 may forward the image to an Image Server 132, as indicated by arrows 134 and 136, for storage. The Image Server 132 may be part of a Picture Archive Communication System (PACS), which may digitally store, transmit, and facilitate the display of radiology images.

The Production Module 130 and the Image Server 132 may communicate in different formats, so the IO Management System may include a Messaging Module 138 to facilitate communication between the server and the Production Module. For example, if the Production Module 130 is able to read text files as input, the Messaging Module 138 may take output from another source, such as the Image Server 132, and convert it into a text file format that the Production Module 130 can interpret.

Alternatively, the Production or Messaging Modules 130, 138 may communicate directly with the Image Server 132 through an API (Application Programming Interface) implemented by the Image Server 132. The API may provide an interface independent of the internal data structures of the Image Server 132. This enables communication even if the server software is updated because the functions used by the interface remain available even if internal structures or functions within the server change. Additionally, this may eliminate the need to have the Image Server 132 authorize direct inputs of data into internal structures.

When an order is received by the IO Management System 102 and accepted by the Access Control Module 122, it may be sent to the Production Module 130. The Production Module 130 may forward the image to an Order Server 140, such as a Radiology Information System (RIS), as represented by arrows 134 and 142, for processing. The Messaging Module 138 may process communication between the Production Module 130 and the Order Server 140.

Once the IO Management System 102 receives an order, the Production Module 130 may assign the order to a user of a client device 106. The Production Module 130 may also assign the order to several users at several client devices 106. If the Access Control Module 122 grants a user of a client device access, the user may retrieve orders from the Order Server 140 and images from the Image Server 132, as indicated by arrows 144, 146, and 148.

In a further embodiment, the IO Management System 102 may have an Operations Module 150 that performs business related operations, such as billing and compensation. Additionally, the IO Management System 102 may have a Data Module 152 that stores data needed by the IO Management System 102. For example, radiologist compensation rules and medical facility billing rules may be included in the Data Module 152. Billing and compensation are further discussed in the description of FIG. 8.

The IO Management System 102 also may include an ASP (Application Service Provider) module 154. The ASP module 154 provides a user of the client device 106 access to orders and images from the Order and Image Servers 140, 132, respectively. Access to these servers is indicated by the arrows 156 and 158. The ASP module 154 is described in greater detail in association with FIG. 10.

The Medical Facilities 104 may include several components for maintaining medical information and transmitting orders and images. For example, the Medical Facility 104A may include a Facility Image Server 160, which uses an image compressor 161. The Facility 104A may also include a Facility Order Server 162, which transmits orders to the Order Server 140 implemented at the IO Management System 102. In one implementation, the Facility 104A may include a Legacy Facility Order Server 166. A translator 164 translates and communicates orders from the Legacy Facility Order Server 166 to the Facility Order Server 162. A HIS (hospital information system) 168 may be connected to the Legacy Facility Order Server 166, the Facility Image Server 160, and the Facility Order Server 162. The Medical Facility 104A may transmit an alert 172 to the IO Management System 102 when patient information is updated. This will be described in greater detail below.

The Facility Image Server 160 may store and transmit images to the IO Management System 102. The Facility Image Server may directly receive the images from an image source, such as an MRI machine, CT scanner, or X-Ray machine (not shown). When transmitting the images, the Facility Image Server 160 may use the Image Compressor 161 to encode the images in a compressed format before transmission to the IO Management System 102. The compressed format may be compatible with the native format of the Image Server 132 implemented at the IO Management System so that no translation is necessary for the Image Server 132 to receive and process the images. Use of the native format may decrease undesirable data loss in translation, decrease translation errors, and improve the speed at which images are transferred to the Image Server 132.

In another implementation, the Facility Image Server 160 does not use the Image Compressor 161, so images are transmitted in an uncompressed format, such as the DICOM format. The Image Server 132 at the IO Management System then translates the DICOM image data into its native format before it is stored or processed in the Image Server 132. In other implementations, the Image Compressor 161 compresses the images in a format that is not native to the Image Server 132 at the IO Management System 102. The compressed image is then decompressed and translated into the Server's 132 native format, or it is translated directly without being decompressed. The Server 132 may include different modules that are responsible for translation of different image server formats, such as a RadWorks translator, an E-Med translator, and an IDX translator.

The Facility Image Server 160 may work in cooperation with a Facility Order Server 162. In one implementation, the Facility Order Server 162 is interfaced in such a way as to easily exchange data. For instance, the Facility Image and Facility Order Servers 160, 162 may share a native formatting scheme. This enables data to be exchanged between the servers without the need for extensive translation or any translation at all. In another implementation, each of the servers implements APIs that facilitate the exchange of data and the control of functionality resident in each of servers.

The Facility Order Server 162 may store and transmit textual medical information to the Management System 102. In one implementation, the Facility Order Server 162 may transmit order information in a format that is native to the Order Server 140 implemented in the IO Management System 102. The Facility Order Server 162 may also send the order information in a compressed format through an order compressor (not shown). The Order Server 140 may decompress the order information and translate it if necessary before ingesting the information.

The Facility Legacy Order Server 166 may be a system that is used by the Medical Facility 104A to input orders. The system may be an older system or a system that is not tightly interfaced with the Facility Image Server 160. Also, the Facility Legacy Order Server 166 may not be able to transmit order information in the native format of the Order Server 140 implemented at the IO Management System 102. The orders may be entered into the Facility Legacy Order Server 166, and translated into a format compatible with the Facility Order Server 162, which may then take advantage of communication schemes between the Facility Image Server 160 and the Order Server 140 that decreases transmission error and increases transmission speed. Utilizing the Legacy Facility Order Server 166, the translator 164, and the Facility Order Server 162 may enable medical facility personnel to obtain the benefits of the Order Server 162 without switching user interfaces based on the Legacy Facility Order Server 166.

The HIS 168 may store medical information for the medical facility 104. The information may include demographic information, medical history, order information, images, and completed reports associated with specific patients. The HIS 168 may be networked to the Legacy Order Server 166, the Facility Order Server 162, the facility image server 160, and other medical databases used by the medical facility 104, such as accounting databases. In one implementation, the HIS 168 is the primary storage system for the medical facility that permits access to all or most of a patient's medical data. The HIS may communicate with the other system servers, such as the Order Servers 162, 166 in a standard protocol. For example, the HIS and the Legacy Facility Order Server may communicate using HL7-compliant communications.

Figure 2B:
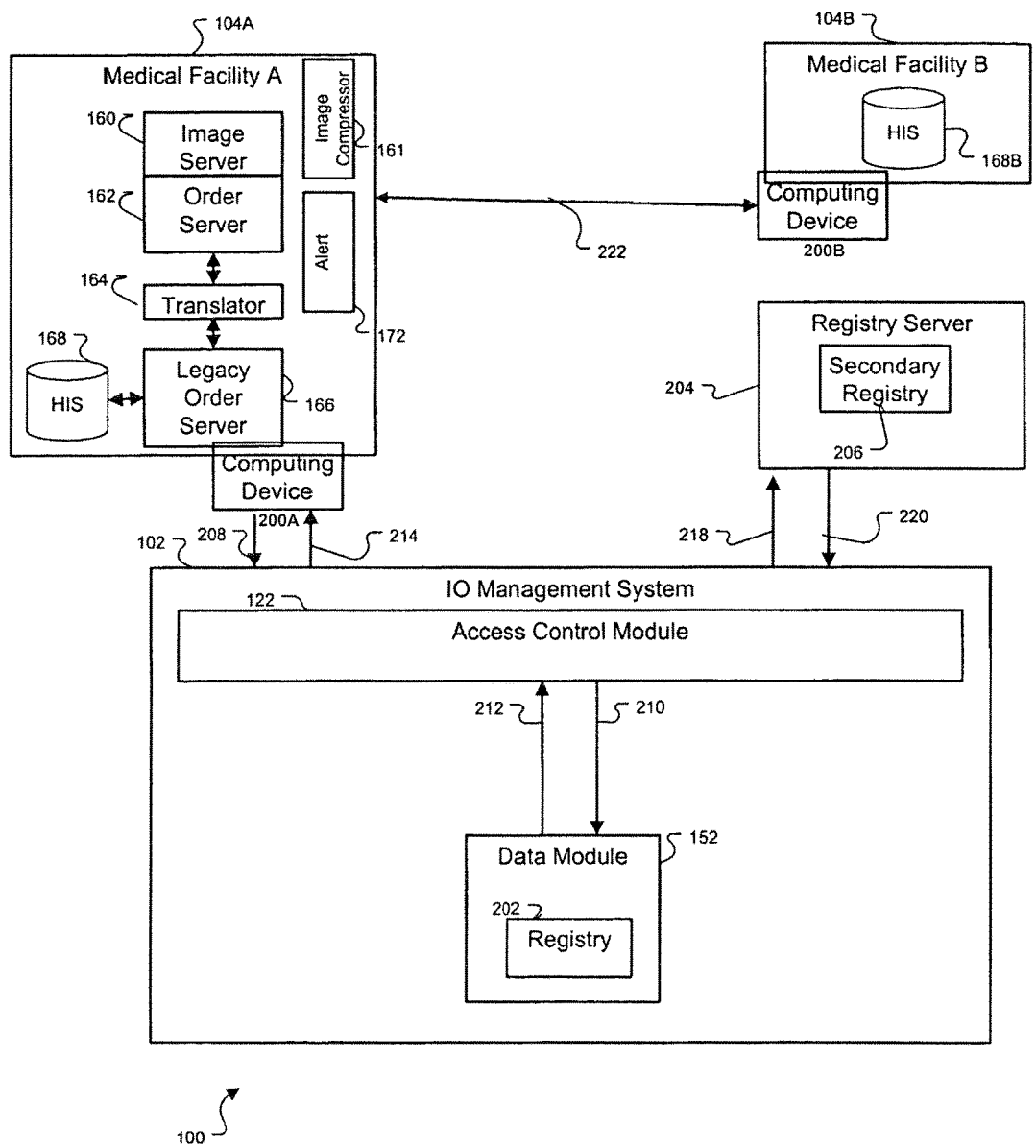
FIG. 2B illustrates a block diagram of a communication scheme using the teleradiology system illustrated in FIG. 2A for transmitting patient information among medical facilities according to an embodiment of the present invention.

FIG. 2B is a block diagram of a communication scheme using the system 100 shown in FIG. 2A for transmitting patient information among medical facilities 104 according to an embodiment of the present invention. In this implementation, the Medical Facility 104A may request patient information, which is stored at medical facility 104B. The IO Management System 102 may serve as a "matchmaker" to provide a computing device at the medical facility 104A with a network address of a computing device at the medical facility 104B. The Medical facility 104A may then establish a direct connection with the medical facility 104B and receive or exchange patient information.

More specifically, each medical facility 104 may contain or otherwise access a HIS 168, which is a system that stores patient information. The HIS may include several computing devices, such as Personal Computers (PCs), servers, terminals, and storage devices, such as individual hard drives and RAID (Redundant Array of Inexpensive Disks) systems. A computing device 200 is networked or interfaced with the HIS and may transmit requests for patient information and receive transmitted patient information.

The IO Management System 102 may include an Access Control Module 122, which is used to verify authorization of patient information requests. If a request for patient information is authorized, the Access Control Module may permit access to the Data Module 152, which may contain a registry 202.

The registry 202 may include information linking patient information with network addresses for medical facilities 104. The network addresses may be provided to a requesting medical facility 104A, and is used by the facility 104A to establish a direct connection with the medical facility 104B that contains the requested patient information. If the network address is not found in the registry 202, the request is forwarded to a separate registry server 204 that contains a secondary registry 206. The secondary registry 206 is accessed to determine if it contains the specified network address, and if it does the address is forwarded through the IO Management System 102, or it is forwarded directly to the medical facility 104A.

For example, a patient is admitted to the medical facility 104A. A doctor at the medical facility may wish to review the patient's previous medical history including images, corresponding reports, and medical files. The doctor, or a technician, may use the computing device 200A to make a request for the patient's information. The patient may have a patient ID (identifier), which uniquely identifies the patient. The patient ID may be a series of numbers, letters, words, symbols, or a combination thereof. The request for patient information may include the patient ID. The computing device 200A may transmit the request to the IO Management System 102, as shown by arrow 208.

The Access Control Module 122 may determine whether a particular user is authorized to request the patient information. A list of authorized persons may be stored in a Data Module 152 and checked by the Access Control Module 122 to determine whether the requester is an authorized person. The list may contain categories of people that are authorized by default to request patient information, such as all medical doctors or medical personnel, the patient which is associated with the information, and the parents of a minor patient. Other groups of people may be given access on an individual basis, such as the insurer for the patient and legal representatives for the patient.

In another implementation, the user transmits proof of authorization with the request for patient information. The proof may include information, such as a digital signature of the patient, an encrypted token or key associated with the patient, or a digital representation of an authorization form.

In one implementation, the patient grants the access after a request for the patient's information has been received by the Access Control Module 122. When the request is made, the Access Control Module 122 sends an alert, such as an email or an automated phone call, to the patient using contact information in the patient's information. The alert may include an identification of the person or facility requesting the information, what type of information is requested, why the information is being requested, and how to approve or disapprove the request. The patient, or a legal representative of the patient, may approve or deny the request by logging into the Access Control Module 122 and entering information verifying the patient's identity, such as a user name and password, and electronic signature, or an encrypted key or token. The patient may then authorize or deny the request. The request may be authorized on a one-time basis, on a time period basis (e.g., the patient may grant access to the records for three months), or on a permanent basis. Additionally, the authorization may be granted for entire medical facilities, or individuals, whether or not they have requested the patient's information, yet.

Alternatively, the patient may store some or all of the patient information on a computer readable medium, such as a CD-ROM, a subcutaneously implanted micro-device, a USB device, or other flash or portable memory device. For example, the CD-ROM may be inserted in a CD-ROM device and read by the computer at the client device 106 or at a medical facility and transmitted to the IO Management System 102. Similarly, a USB device may be inserted into a USB port at the client device 106 or at the medical facility 104. The information is read from the USB device and transferred to the IO Management System. Alternatively, the implanted micro-device is an encapsulated microchip, such as a radio frequency (RF) microchip. The microchip is read by a RF scanning device by placing the skin where it is implanted near the reader. The reader may then transmit information to the IO Management System 102.

In one implementation, a patient may edit his or her demographic information by inserting or positioning the computer readable medium so that the information it contains is accessed. Then the data on the computer readable medium is synchronized with the edited data stored by the IO Management System 102. The client device 106 initiates the synchronization process by transmitting a change alert to the IO Management System 102, where the change alert signifies that the patient information has been modified or supplemented. The change alert may include a patient identifier that specifies which patient records need to be updated. After receiving the change alert, the IO Management System 102 may request the updated patient information from the client device 106. The client device 106 may transmit all of the information stored on the computer readable medium. The IO Management System 102 replaces the existing patient information stored in the Data Module 152 information for the patient corresponding to the patient identifier with the updated patient information transmitted from the client device. Alternatively, client device 106 transmits only the supplemented or modified patient information. In this case, the IO Management System 102 may only replace the existing patient information that has been modified and may add the supplemental information to the existing patient information for the patient specified by the patient identifier.

Alternatively, the data is synchronized with the patient information stored on the IO Management System 102 anytime the medium is accessed by the client device 106. Additionally, when the medium is accessed, the client device 106 may transmit a request to the IO Management System 102 to update the medium with any new patient information.

In one implementation, an update module stored either on the medium or on the client device is executed by the client device 106. The update module establishes a TCP/IP session between the client device 106 and the IO Management System 102. The module then transmits an update request and a patient identifier. The IO Management System 102 locates the patient information associated with the patient identifier in Data Module 152 and transmits the information to the client device 106. Additionally, the IO Management System 102 may query the medical facilities as discussed above to receive the patient information. The patient information is then transmitted to the client device and written to the medium. At a later time when the patient is admitted to a medical facility, the medical facility may retrieve the medical information from the computer readable medium using a computing device instead of requesting it from the IO Management System 102.

Alternatively, the medium is part of an authorization scheme. A patient may receive an alert that prompts the patient to insert or position the medium for reading by a client device 106. For example, the alert may be an e-mail sent to a patient e-mail address by the IO Management System 102. The patient's e-mail address is stored in the Data Module 152 at the IO Management System 102 with the patient's medical data. The IO Management System 102 may access the patient's e-mail address and use a mail server program to transmit the e-mail message. The alert may also be a telephone message. The IO Management System 102 may retrieve the patient's telephone number from the patient information stored in Data Module 152. The system 102 then transmits the telephone number to an automatic dialing device, which calls the patient and gives an automated message instructing the patient to insert the medium into the client device 106.

Once the medium is accessed by the client device 106, the device 106 may search the medium for an identity tag associated with a patient's identification. The identity tag may be a private key or an encrypted token known only to the patient. The client device 106 may transmit a proof that the medium contains the identity tag or it may submit an encrypted version of the identity tag. The IO Management System 102 receives the proof or the encrypted version and verifies the proof or decrypts the version, respectively. The proof is verified by comparing it against patient identity information stored for the submitting patient in Data Module 152. Alternatively, the decrypted version is compared to the patient identity information stored in the Data Module 152. After the patient's identity is verified by the IO Management System 102, the system 102 may transmit a request for the patient to approve or deny an access request to the patient's information submitted by a third party.

The request may also be approved automatically based on information stored within the medium, such as a pre-approved list of medical facilities or individuals. For example, the client device may query the medium to determine if a pre-approval list exists. If the list is present, the client device 106 may determine if the third party requesting access is included on list. If the third party is included on the list, the client device may transmit a response indicating the access request is approved. Alternatively, the IO Management System 102 may store the pre-approval list with the patient information in the Data Module 152, and the system may determine if the third party submitting the access request is pre-approved without sending an alert to the patient.

In another implementation, the medium may store all or part of the registry, which is described more fully below. For example, the medium may store a registry entry for the patient who uses the medium. The registry 202 is read from the medium by a medical facility when a patient is admitted. The registry 202 may contain network addresses that identifies where the patient information is stored, such as servers in other medical facilities, or database files on the Management System 102. In one implementation, the medical facility may have an information retrieval module, which uses the network address to retrieve the patient information. The information retrieval module may use secure file transfer protocol (SFTP) to establish a TCP/IP socket connection to the device specified by the network address. The retrieval module may then request and receive the patient information.

After authorization, the registry 202 may be accessed as shown by arrow 210. The patient ID may be compared with the patient IDs stored within the registry. If a patient ID in the registry matches the patient ID associated with the request for patient information, the registry may determine if a network address is associated with the patient ID. The network address may be an address, such as an IP (Internet protocol) address, or a URL (uniform resource locator), which identifies the location of a computing device on a network. If the registry has one or more network addresses associated with the patient ID, it may return the network addresses to the computing device 200A as shown by arrows 212 and 214. The network addresses may identify a computing device 200B at a medical facility 104B that includes a HIS 168B that contains information for the patient associated with patient ID.

If the registry does not contain a network address for a medical facility 104B, it may contain a network address for a registry server 204, which may contain a secondary registry 206. The secondary registry 206 may also contain patient IDs and network addresses for medical facilities that contain patient information associated with the patient IDs. This permits decentralization of the registry information. For example, the secondary registry 206 may be responsible for maintaining patient IDs and associated network addresses for a region, such as city, county, state, or country. If a request for patient information is made to the registry 202, the registry may forward it, as shown in by the arrow 218, to the secondary registry responsible for maintaining that information.

If the secondary registry 206 contains a network address associated with the patient ID, this information may be transmitted back to the IO Management System 102, which may transmit it to the medical facility 104A, as shown by arrow 220. Alternatively, the registry server 204 may transmit the network address to the medical facility 104A directly (not shown) without transmitting information to the IO Management System 102.

Secondary registries 206 may hold information which is duplicative of information stored in the registry 202. This duplicative information may be used to insure the registry information is correct by checking it against information stored in other registries. Additionally, storing the information in more than one location and on more than one machine may provide benefits, such as a backup in case of data failure and a security measure to prevent all data from being compromised if the system is accessed by unauthorized users.

In another implementation, the registry server 204 is queried instead of the IO Management System 102. Distributing the registries among several computing devices may increase the response time to the queries for patient information and decrease message traffic, required bandwidth, and computational load on the IO Management System 102.

If neither the registry 202 implemented at the IO Management System 102 nor the secondary registry 206 contains a network address associated with the patient ID, the IO Management System may return a negative response to the requesting medical facility 104A indicating that no network addresses are available. In another implementation, the IO Management System may initiate queries to medical data storage systems at medical facilities for information associated with that patient ID if no network addresses are found. The queries may be transmitted to the computing devices 200 at each facility 104. If a facility is found that contains information associated with the patient ID, the network address for the computing device 200 may be added to registry 202 and transmitted to the requesting medical facility.

If a network address is returned to a requesting medical facility 104A, the facility 104A may use it to establish a direct link (as shown by arrow 222) with the medical facility 104B, which contains patient information associated with the patient ID. In one implementation, the Facility 104A may then request and receive patient information from the facility 104B. In another implementation, and the facilities 104 may exchange patient information that is related to the patient ID.

This scheme may also be employed by the users of client devices 106 to obtain patient information. For example, a patient, a remote doctor, or an insurance company employee may request patient information associated with a patient ID. Client software installed on the client device 106 may permit the request to be transmitted and the network address to be received. Client software may then establish a connection with the medical facility 104B and download the patient information for display. The software may include applications, such as a Web browser and plug-ins for the Web browser that enable a browser to perform operations such as displaying the medical information and images. In another implementation, software may include specific applications for viewing images, reports, and other medical history or data.

Figure 3:
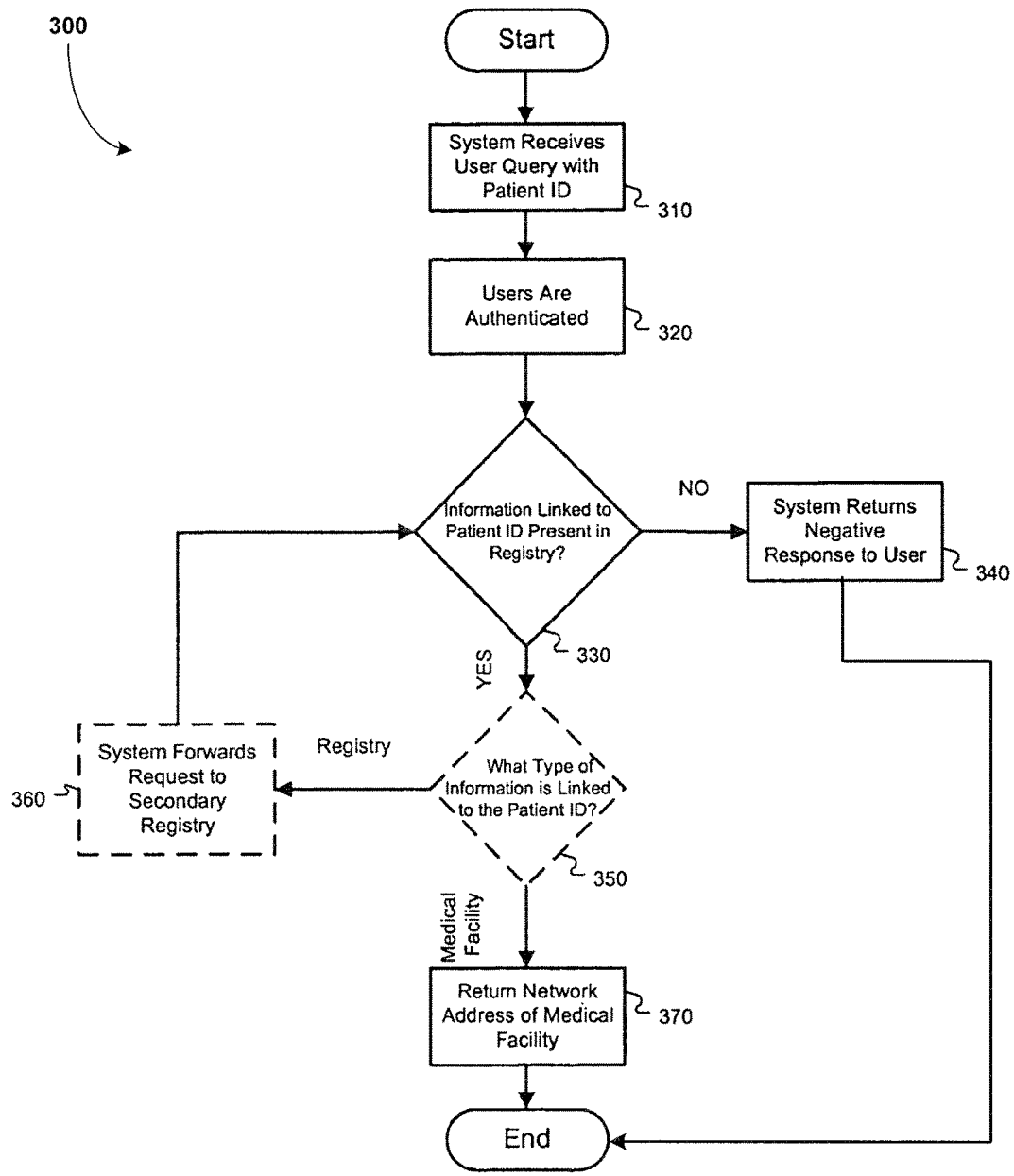
FIG. 3 illustrates a flowchart of exemplary operations illustrating how the teleradiology system illustrated in FIG. 2B may communicate patient medical data according to an embodiment of the present invention.

FIG. 3 is a flowchart of example operations 300 illustrating how the system shown in FIG. 2B may communicate patient medical data according to one implementation. For example, a computer program product may include instructions that cause a processor to perform operations comprising the steps of method 300.

In step 310, the operation "System Receives User Query with Patient ID" is performed. The system 102 may receive a query from a user for patient information associated with a patient ID. For example a medical facility 104A may request patient information for a patient that has been admitted to the hospital. This request is transmitted by the computing device 200A, shown in FIG. 2B. The request may be for a network address of the computing device 200B, which may communicate with the HIS 168B that contains historical information for the patient.

In step 320, the operation "Users are Authenticated" is performed. The system 102 may include an Access Control Module that restricts access to patient information. For example, the Access Control Module 122 may only allow authorized persons access to the registry 202, which contains information linking a patient ID to a source of patient information. The authorization may have default authorized persons, such as doctors and medical personnel, and specifically authorized persons, such as insurance company employees. Additionally, the user query may also contain proof that a user is authorized, such as a digital representation of an authorization form. This proof is used to verify that a user is authorized.

In step 330, the operation "Information Linked to Patient ID Present in Registry?" is performed. The registry is accessed to determine whether information linked to the patient ID is present. If it is not, step 340 is performed. If it is, step 350 is performed. For example, the patient ID transmitted with the request for patient information is compared to patient IDS stored within the registry. If a match is found, step 350 is performed. If no match is found, step 340 is performed.

In step 340, the operation "System Returns Negative Response to User" is performed. A negative response is transmitted to the user requesting patient information there is no match for the patient ID in the registry. For example, the system 102 may not find a match in the registry for the patient ID transmitted with a request for patient information. The system 102 may send a response indicating there is no information in the registry associated with the provided patient ID.

In step 350, the operation "What Type of Information Is Linked to the Patient ID?" is performed. The type of information linked to the patient ID is determined. The type may include a network address for a medical facility or a network address for a secondary registry. For example, if a patient ID provided with the request matches the patient ID present in the registry 202, it is determined what type of information associated is linked with the patient ID. If the registry is stored in a database, the field name storing a particular network address is used to determine whether the address identifies a medical facility or secondary registry. If the network address is associated with a secondary registry, optional step 360 may be performed. If the network addresses associated with a medical facility, step 370 may be performed.

In optional step 360, the operation "System Forwards Requests to Secondary Registry" is performed. If the information associated with the patient ID is a network address for secondary registry, the system 102 may forward the requests to the secondary registry identified by the network address. For example, if the network address identifies the registry server 204, the IO Management System 102 may transmit the request to the registry server. The step 330 may then be repeated to determine whether information linked to the patient ID is present in the Secondary Registry 206.

In step 370, the operation "Return Network Address of Medical Facility" is performed. The network address associated with the patient identifier provided with the request for patient information may be transmitted to the requesting user. For example, after determining that the patient ID matches a patient ID in either the registry 202 or the secondary registry 206, the system 102 may transmit the network address identifying the medical facility 104B that contains the requested patient information. The user, such as the medical facility 104A, may then establish a direct connection with the medical facility 104B, request, and receive the patient information using a peer-to-peer connection.

Users may be charged a fee for the "matchmaker" service provided by the system 102. For example, a user may be charged for every request for patient information. A user ID may also be presented with the request for patient information. The user ID is sent to a billing module implemented in the Operations Module 150. The billing module may calculate the cost of the request based on billing rules that is stored in the Data Module 152.

The user's credit card information may also be included in the request for information or a stored in the Data Module. After the request is received the user's credit card is billed. Alternatively, an invoice is generated and sent to the user. In another implementation the user may pay a subscription fee for a certain number of requests made during a defined period of time, such as 100 requests per week. In another implementation, the user may only be charged if the request for patient information is successful and a network address for the medical facility 104B containing the patient information is returned to the requesting medical facility 104A.

Figure 4:
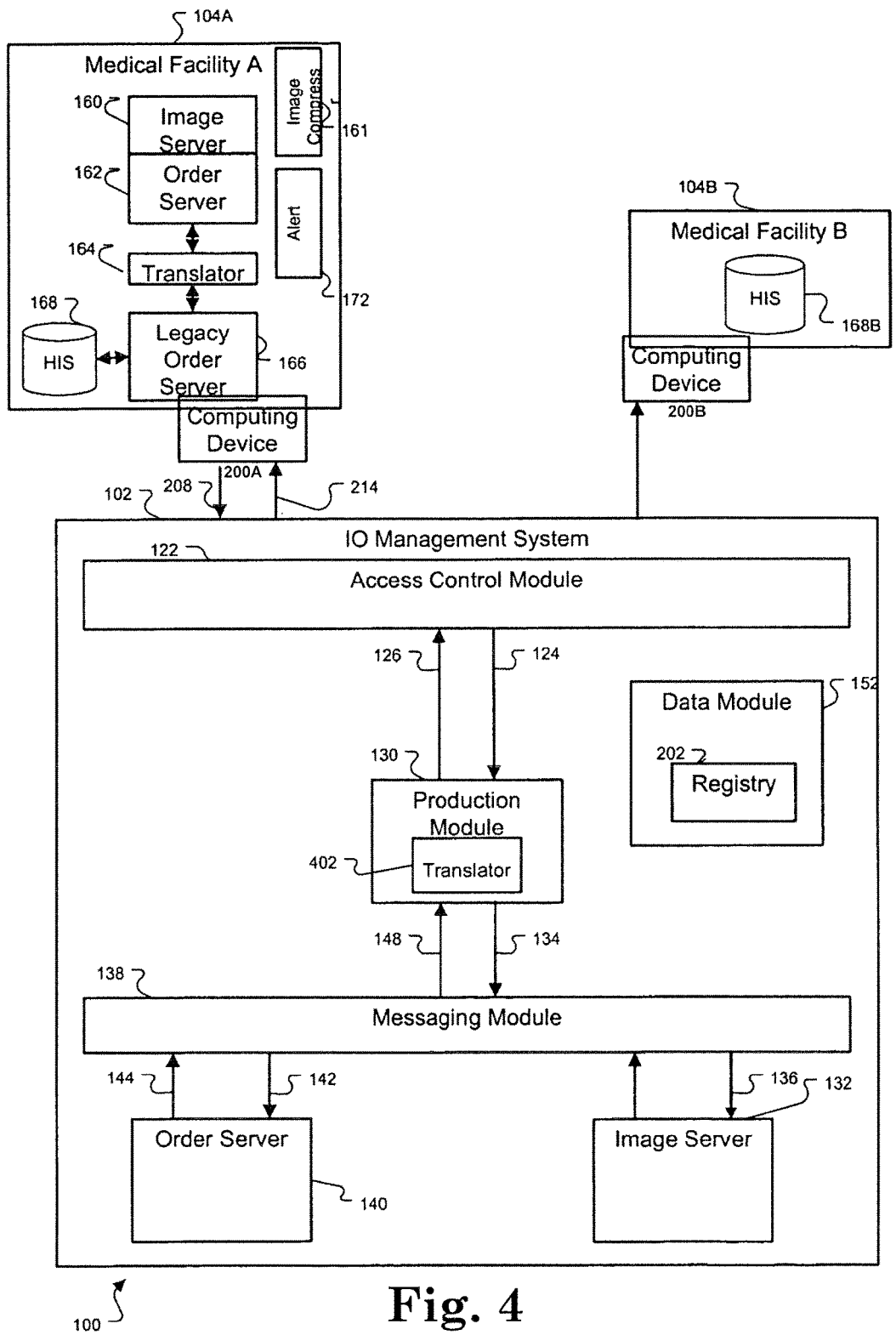
FIG. 4 illustrates a block diagram of a communication scheme using the system shown in FIG. 2A for transmitting patient information among medical facilities according to an embodiment of the present invention.

FIG. 4 is a block diagram of a communication scheme using the system 100 shown in FIG. 2B for transmitting patient information among medical facilities 104 according to another implementation. In this implementation, the Medical Facility 104A may request patient information, which is stored at medical facility 104B. The IO Management System 102 may act as a "middleman" to request the medical information from the medical facility 104B and then transmit it to the medical facility 104A. The system 102 may use a registry, such as the registry 202, to locate the network address for the medical facility 104B, but may not provide this network address to the requesting medical facility 104A. Instead, the system 102 may retrieve the requested medical information from the medical facility 104B and transmit it to the requesting medical facility 104A.

The Medical Facilities 104 and the IO Management System 102 may include many of the same components as shown in the FIGS. 2A and 2B, but the System 102 may also include a translator 402, which will be described in greater detail below.

In the implementation shown in FIG. 4, the Medical Facility 104A may transmit a request for patient information to the IO Management System 102. The request may include a patient ID. The IO Management System 102 may receive the request and the Access Control Module 122 may determine whether the requester is authorized to view the patient information. If the requester is not authorized, the request is refused. If the requester is authorized, the IO Management System 102 may access the registry 202 within the Data Module 152. The patient ID included in request is used to determine if there is a matching patient ID with the registry. The functionality described above may be similar to the functionality described in association with FIGS. 2A and 2B.

If a matching patient ID is not located within the registry, the IO Management System may return a negative response to the requesting medical facility 104A indicating that no information associated with the patient ID was found.

In another implementation, the IO Management System 102 may initiate queries to medical data storage systems at medical facilities for information associated with that patient ID if no network addresses are found. The queries are transmitted to the computing devices 200 at each facility 104. If a facility is found that contains information associated with the patient ID, the network address for the computing device 200 is added to the registry 202, and the system 102 may retrieve the information.

The medical facilities queried may be facilities that are located within the same region as the requesting medical facility. For example, the system 102 may query medical facilities in the same city, county, or state. This query may have a higher probability of success than querying a medical facility in another region because a patient admitted to the requesting medical facility may be more likely to have been treated at a facility in the surrounding region than at a facility in a different city, county, or state. In another implementation, all medical facilities with network addresses in the registry are queried for the patient information.

If a matching patient ID is located within the registry, there may be network addresses identifying computing devices 200 for medical facilities 104, which may contain patient information associated with the patient identifier. For example, the system 102 may use the network address to establish a connection with the medical facility 104B. After a connection is established, the system 102 may request and receive the patient information associated with the patient ID.

Images received from the medical facility 104B may be transmitted to the Image Server 132 before they are transmitted to the requesting medical facility 104A. The images may be in a different format than the native image format of the Image Server 132 and may require remapping, or reformatting, before the Image Server 132 may accept the images. This may be accomplished using modules that are responsible for translating different image server formats as described above. Alternatively, a Translator 402 implemented in the Production Module 130 may be used to translate images from the received image format to the native format of the Image Server 132.

Reports received from the medical facility 104B may be transmitted to the Order Server 140 before they are transmitted to the requesting medical facility 104A. The orders may be in a different format than the native report format of the Order Server 140. The translator 402 may also be used to translate the reports from the received report format to the native report order format of the Order Server 140. Alternatively, the Order Server 140 may have modules responsible for translating the reports into the native format similar to the modules described for the Image Server 132.

In one implementation, translation may occur in the following way. The device requirements of each system may be determined dynamically each time a transaction is performed. For example, a command may be transmitted to the computing devices 200A to identify what types of HIS system, order server, and image server are operating at the medical facility 104A. Alternatively, the system parameters may be stored in a database or the registry 202 that is queried to determine what formats, such as image format, report format, and medical file format, are required.

For example, to format a report, the following steps may be performed. After the report is received by the IO Management System 102, it may convert the report from a format compatible with the client device to a format compatible for the medical facility. There may be a pointer that associates the images with an order or report. Given this pointer, the identity of the ordering facility, and knowledge of the facility's data format requirements, the finished report may be formatted into appropriate structure and delivered to the ordering facility.

Reformatting may require parsing the report, storing the data in a structure that identifies each piece of information, creating a new report using the stored data and remapping rules specific to the report format required by the medical facility. For instance, the remapping rules may be stored in the translator 402 or in the Data Module 152. They may specify where in the new report structure information from the old report structure must be placed. For instance, if the last name of the patient is in a first field of the old report, it may be remapped to a third field of the new report based on the remapping rules used by the translator 402. Similar remapping rules may be used to reformat images and other medical information.

The knowledge of the facilities data format requirements may be recorded in a database implemented at system 102. The requirements may be entered when the facility registers with the system 102, or they may be automatically determined by the system 102 and entered into the database.

If conversion is necessary, the report may be validated by comparing the order information with the converted report information to ensure the information has been mapped correctly during the report conversion process. For example, the patient name fields may be compared. The order corresponding to the report may be accessed using the unique identifier discussed earlier.

In another implementation, received patient medical information may be stored in the Data Module 152 before it is transmitted to the requesting medical facility 104A. This patient medical data may include a variety of information, such as medical charts, patient demographic information, prescription drug records, hospitals to which the patient has been at admitted, information on medical procedures performed on the patient, medical personnel notations, and the received reports and images.

The Data Module 152 may serve as a cache that stores the patient information for future queries. For example, a query is received from a medical facility for medical information for Patient A. The IO Management System 102 may retrieve the information as described above, store it in the Data Module 152, and relay it to the requesting medical facility using a caching module. If the same or a different medical facility requests the information, the IO Management System 102 may retrieve the medical information from the Data Module 152 instead of from an external medical facility. This may decrease the time needed for the requesting medical facility to receive the data.

In one implementation, the caching module may create and store persistence values with the patient's medical information. The persistence values may indicate how long the data has been cached in the Data Module 152. When the persistence values indicate the medical data has not been accessed for a predetermined period of time, the caching module may delete or overwrite medical information associated with the persistence values.

The persistence values may be based on several measures. For example, the IO Management System 102 may store patient information based on time (e.g., the system stores all the requested patient information for two months), the requesting facility (e.g., the system stores all the requests from a particular medical facility or client device user), and the frequency of requests (e.g., the system stores all patient information that is requested more than once).

The registry may indicate whether information is stored locally in the Data Module 152 or remotely at the medical facility 104. For example, the registry may include a pointer to the information in the Data Module. The caching module may update the registry with the pointer when patient information is stored in the Data Module 154. When a request is made for patient information, the IO Management System 102 may access the pointer in the registry to determine if the data is stored locally. If the pointer is present, the IO Management System 102 may use the pointer to locate and access the patient information in the Data Module. If the pointer is not present, the IO Management System may retrieve the data from the medical facility 104 using a network address for that medical facility stored in the registry. Alternatively, the pointer may always be present. When the patient information is cached, the pointer specifies a location in the Data Module 152, and when the information is not cached, the pointer specifies a location at the remote facility 104.

In another implementation, the medical data requested by the medical facility is not transmitted to the facility. Instead, personnel at the requesting medical facility may view the requested data using the ASP module described in more detail below. The information may remain on the IO Management System and is not transmitted to or stored at the requesting medical facility.

The translator may determine what format the requesting medical facility 104A requires to receive the patient information. For instance, the facility 104A may require the information in a format compatible with the HL7 or IHE standard. Also, the facility may require the images in a specific format, such as raw DICOM (Digital Imaging and Communications in Medicine) format, RadWorks format, and E-Med format. The translator 402 may translate the patient information, including the images to the proper format before transmitting the data to the facility 104A.

The patient information may be transmitted to different servers or computing devices at the facility 104A. For example, the images may be transmitted to the Facility Image Server 160, the reports to the Facility Order Server 162, and the additional patient information to the computing device 200A. In another implementation, all the patient information may be transmitted to the computing device 200A for transmission to the HIS 168.

The proper transmission format required for the medical facility 104A may be stored in the Registry 202 of the Data Module 152. The translator may access the Registry 202 to determine what translation algorithm to use for the requesting medical facility 104A. After translation, the system 102 may transmit the data. Alternatively, the system 102 may determine the translation requirements of the requesting medical facility on-the-fly. For example, the registry may not contain the translation requirements for the requesting medical facility 104A, so the system 102 may query the facility 104A to determine what format or formats the system requires for the patient information.

After determining the requirements, the Translator 402 may translate the patient information and transmit it in the required format. Additionally, the translation requirements may then be entered in the registry and associated with the medical facility 104A for future reference. In another implementation, similar transmission requirements may be entered in the registry for the sending medical facility 104B. The requirements may be used for any necessary translation if the sending medical facility later requests patient information.

A user, such as a patient, a remote doctor, and an insurance employee may also request patient information. Similar steps and structure to those described for the requesting medical may be employed by these users. However, these users may not have some of the elements described in FIG. 4, such as the Facility Image and Order Servers 160, 162 or a HIS 168. The users may simply have a computing device 200A which has a browser or other software configured to receive the patient information for display or storage.

There may be more than one network address associated with the patient ID. The IO Management System 102 may request information from each of the facilities 104B associated with the network address and transmit it to the requesting medical facility 104A or the user. The patient information may be passed as it is received by each of the medical facilities 104B, or it may be accumulated and passed in one transmission.

In another implementation, the system shown in FIG. 4 may also have a secondary registry as shown in FIGS. 2A and 2B and described above.

A user requesting the patient information may be billed in a manner similar to that described above for FIG. 2B. However, instead of being billed for providing a network address of another medical facility that contains the patient information, the charge may be for directly providing the patient information to the requesting facility. Additional fees may be charged for any translation operations performed by the translator 402.

Figure 5:
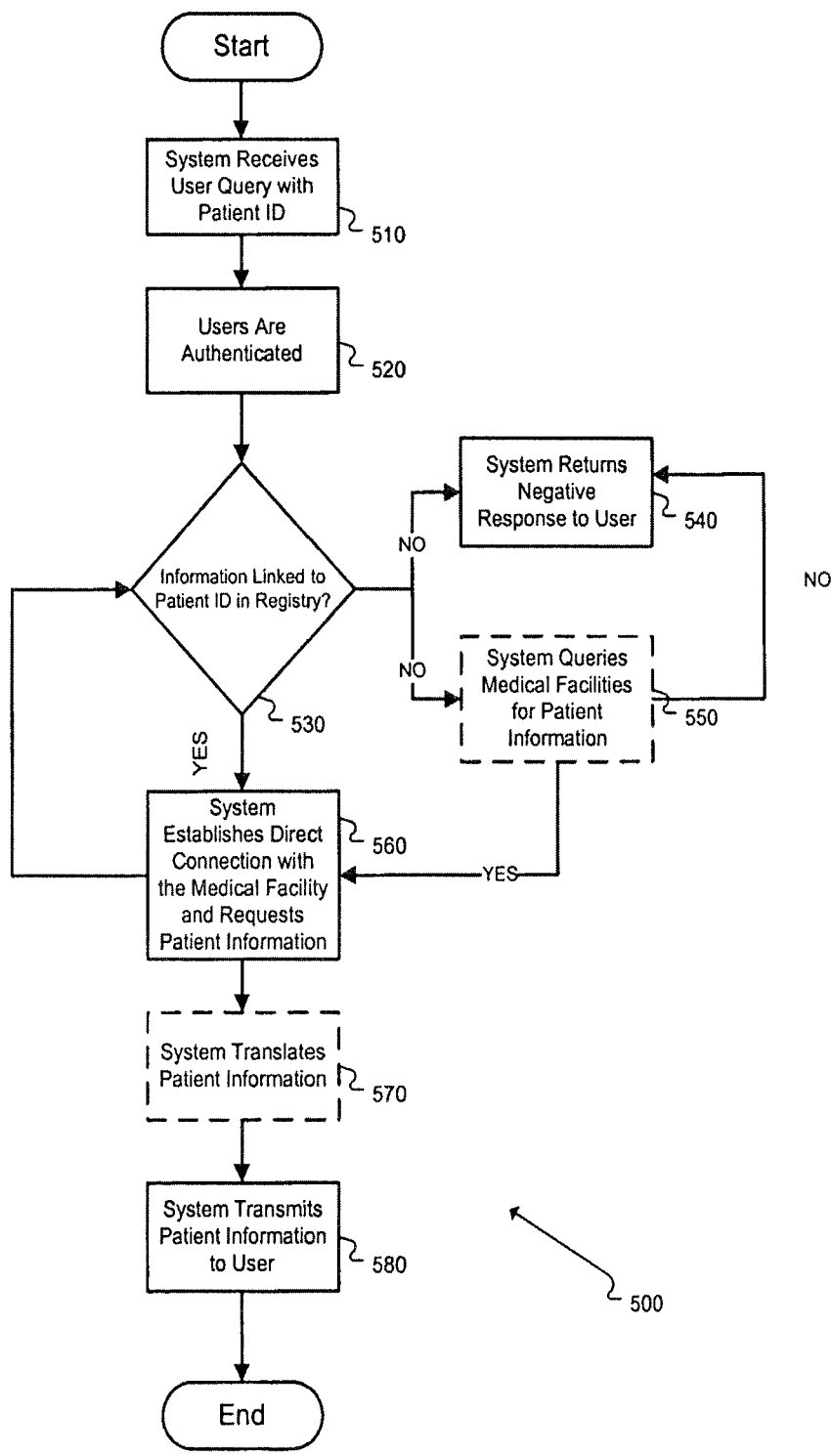
FIG. 5 illustrates a flowchart of exemplary operations that the teleradiology system illustrated in FIG. 4 may perform to communicate patient medical data according to an embodiment of the present invention.

FIG. 5 is a flowchart of exemplary operations 500 that the system shown in FIG. 4 may perform to communicate patient medical data according to one implementation. For example, a computer program product may include instructions that cause a processor to perform operations comprising the steps of method 500.

The steps 510, 520, 530, and 540 are similar to steps 310, 320, 330, and 340 in FIG. 3. However, if the results of the operation "Information Linked to Patient ID Present in Registry?" performed in step 530 are "NO," the step 540 or the optional step 550 may be performed.

In optional step 550, the operation "System Queries Medical Facilities for Patient Information" is performed. If no information is linked to the patient ID, the system may query the medical facilities to determine if the facilities have patient information linked to the patient ID. For example, the IO Management System 102 may query medical facilities 104B within the same city as the requesting medical facility 104A. The system 102 may transmit the patient ID with the query to the facilities 104B to determine if the patient ID matches any patient IDs within the facilities' systems. If there is no matching patient ID for any of the systems queried, step 540 may be performed. If one of the medical facilities 104B does have a matching patient ID, step 560 may be performed.

In step 560, the operation "System Establishes a Direct Connection with the Medical Facility and Requests Patient Information" is performed. If the queried medical facility has information related to the patient ID, the system may establish a direct connection with the medical facility and may request the patient information. For example, the medical facility 104B may return a response that indicates it has patient information associated with the patient ID. The system 102 may establish a connection with the medical facility 104B, request, and receive the patient information. If more than one medical facility returns a positive response, the patient information may be received from each of the medical facilities. Additionally, if more than one network address is linked to the patient ID as described in steps 330 and 530, connections with each of the medical facilities specified by the network addresses may be initiated to obtain the patient information from each facility.

In optional step 570, the operation "System Translates Patient Information" is performed. The system 102 may translate patient information received from the sending medical facility. For example, the translator 402 may determine what format the requesting medical facility requires to process the patient medical information. The translator may then translate the received patient information into the required format.

In step 580, the operation "System Transmits Patient Information to the User" is performed. The system transmits the received patient information to the requesting user. For example, the system 102 may transmit patient information to the requesting medical facility 104A.

FIG. 6 is a diagram of the registry 202 according to one implementation. The registry may contain separate entries for patient IDs 600. Linked with the patient ID may be a medical facility network address 602, a medical facility ID 604, medical facility system requirements 606, modification dates 608, and a secondary registry network address 610. Each one of the information types linked with the patient ID may include multiple entries. For example, there may be multiple medical facility network addresses 602 linked with each patient ID. Each of the network addresses may identify a different medical facility that contains patient information for the patient identified by the patient ID. Additionally, one medical facility may have several network addresses, such as one for the facility image server 160, one for the Facility Order Server 162, and one for the computing device 200A.

The medical facility ID 604 may include an identifier for the medical facility. This facility ID 604 may be provided to the requesting medical facility 104A when the network address is provided in the "matchmaker" method shown in FIGS. 2B and 3, or when the patient information is transmitted in the "middleman" method shown in FIGS. 4 and 5. The facility ID 604 may be used by the requesting medical facility to record the source of the patient's information or to facilitate contacting the medical facility if clarification or additional patient information is required. In one implementation, the medical facility ID may be a unique number identifying the facility (such as 123456789) a name (such as James River Hospital), or a combination thereof (JamesRiver123456789).

In one implementation, the network address 602 may identify systems other than medical facilities. For example, the network address may identify universities and remote doctor systems, which may store patient information. Likewise the medical facility ID may identify these other systems instead of medical facilities.

The medical facility system requirements 606 may describe the format that is required by the medical facility identified by the network address. For example, one network address may identify a facility image server which only accepts raw DICOM data. The system requirements 606 may be used by the translator 402 to determine the appropriate format for the patient information before transmitting the information to the requesting medical facility 104A.

The modification dates 608 may identify the dates that new information associated with the patient ID was generated. For example, if the medical facility with the medical facility ID 123456789 admitted the patient on Oct. 10, 2004 and later on Nov. 2, 2005, both these dates may be entered in the registry. The dates may be used to determine whether a requesting medical facility has already received patient information from a medical facility for that patient. For example, a requesting medical facility 104A may request patient information for patient 987654321 and may receive it on Nov. 11, 2004. Later, on Dec. 2, 2005, the facility 104A may request information for the patient again. The modification dates 608 may be used to prevent information associated with the date Oct. 10, 2004 from being transmitted again along with the information that was generated on Nov. 2, 2005. The modification dates 608 may be transmitted to the registry as described in greater detail below.

The secondary registry network address 610 may identify the address of the registry server 204 that contains the secondary registry 206. This may be used in the manner described in association with FIGS. 2B and 3.

In other implementations, the registry 202 may also contain information, such as a summary of the patient information (e.g., X-ray Images of the Head, Current Prescriptions, and Family Medical History), medical facility admission, and check-out dates for patients, and authorization information (e.g., BlueCross BlueShield employees are authorized to view patient information).

Figure 7:
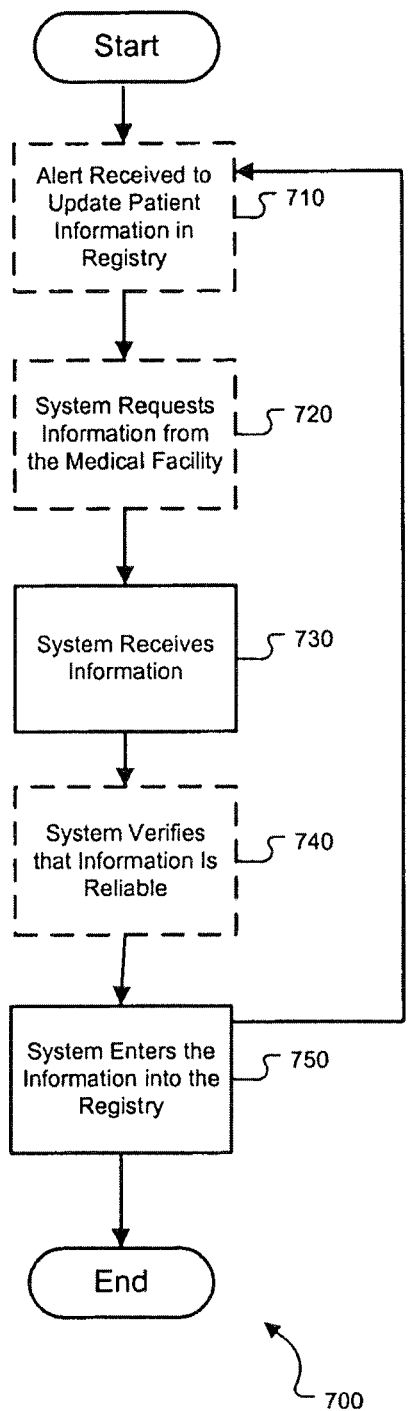
FIG. 7 illustrates a flowchart of a method for entering information into the patient information registry according to an embodiment of the present invention.

FIG. 7 is a flowchart of a method for entering information into the registry 202 according to one implementation. For example, a computer program product may include instructions that cause a processor to perform operations comprising the steps of method 700.

In optional step 710, the operation "Alert Received to Update Information in Registry" is performed. The system may receive an alert from a medical facility 104 that new patient information has been generated and that the information is available for updating the registry. For example, a patient may be admitted to a hospital. The patient may already have a unique patient identifier, or a unique identifier may be generated for him or her at the hospital. Hospital personnel may enter information about the patient's pending and past medical procedures into the hospital's HIS. The computing device 200A networked with the HIS may send an alert 172 to the system 102 that new information associated with the patient's ID has been created.

In another implementation, upon entry of patient information associated with a patient ID, an alert may be sent to the IO Management System 102 to obtain or be ready to obtain patient information from other medical facilities. This may occur, for example, when the patient associated with the patient ID 12345679 is admitted to a hospital. The computing device 200A may send out an automatic query to the system 102 to cache information associated with the patient ID. The "cached" information may be stored in the system's Data Module 152. If a doctor later requests additional patient information from the IO Management System 102, the information may be transmitted to the computing device 200A and made available to the requesting doctor. Alternatively, the system 102 may receive the alert and locate medical facilities that contain information associated with a patient ID, but the system may not initiate a download of the information until the information is requested by a doctor or other medical personnel.

In some implementations, the medical facility may receive a notification that additional patient information is available for download. The notification may be inserted in the patient's medical information stored at the medical facility. It may also be stored separately. Regardless of its location, users of the HIS or computing device 200A may receive the notification when accessing the patient information. In another implementation, the notification may be received independent of whether the associated patient information is viewed. For example, it may be displayed in an email or a worklist assigned to a doctor or medical personnel.

In other implementations, the alert may initiate an automatic download of patient information. For example, the patient with the patient ID 123456789 may be admitted to a hospital. When the patient ID is entered into the hospital's system, it may automatically be sent with a request to the IO Management System 102 to download additional information associated with patient ID. This may happen without any user intervention.

In optional step 720, the operation "System Requests Information from the Medical Facility" is performed. The IO Management System may request from the medical facility the information associated with the patient ID. For example, the system 102 may request information such as the medical facility's network address 602, the medical facility's ID 604, the system requirements 606, and the modification dates 608.

In one implementation, steps 710 and 720 may be combined, where the information associated with the patient ID is sent with the alert or serves the function of the alert, namely to inform the system 102 that new information is available. In another implementation, only step 720 may be performed. For example, instead of a computing device at a medical facility initiating the data transfer, the system 102 may periodically query the medical facility to determine if any new patient information has been generated. The system 102 may use an application similar to a web crawler, or web spider that communicates with the medical facilities' systems in a methodical, automated manner to determine whether new patient information is present. On finding new information, the system may request the information to update the registry.

In step 730, the operation "System Receives Information" is performed. The system may receive the information associated with the patient ID. For example, the system 102 may receive patient information, such as information shown in FIG. 6.

In optional step 740, the operation "System Verifies that Information is Reliable" is performed. The Access Control Module may determine whether the medical facility sending the patient information is an authorized sender. For example, the Access Control Module 122 may compare the sending medical facility's network address and medical facility ID with the medical facility network address and the medical facility ID stored in the registry. The patient modification date may also be compared with previous modification dates to determine if the information is already recorded in the registry. If the information has been previously stored, the newly received information may be compared with the previously stored information to determine if the information is identical, which may indicate the transmissions were reliable.

In step 750, the operation "System Enters the Information into the Registry" is performed. The IO Management System 102 may enter the received information into the registry. For example, the system may enter the received information associated with patient ID into the registry 202. The method 700 may be repeated for separate medical facilities 104. The method 700 may also be repeated for each facility every time new patient information is generated, and it may be repeated for a single medical facility after a predetermined time period or the occurrence of an event, such as the alert in step 710.

Figure 8:
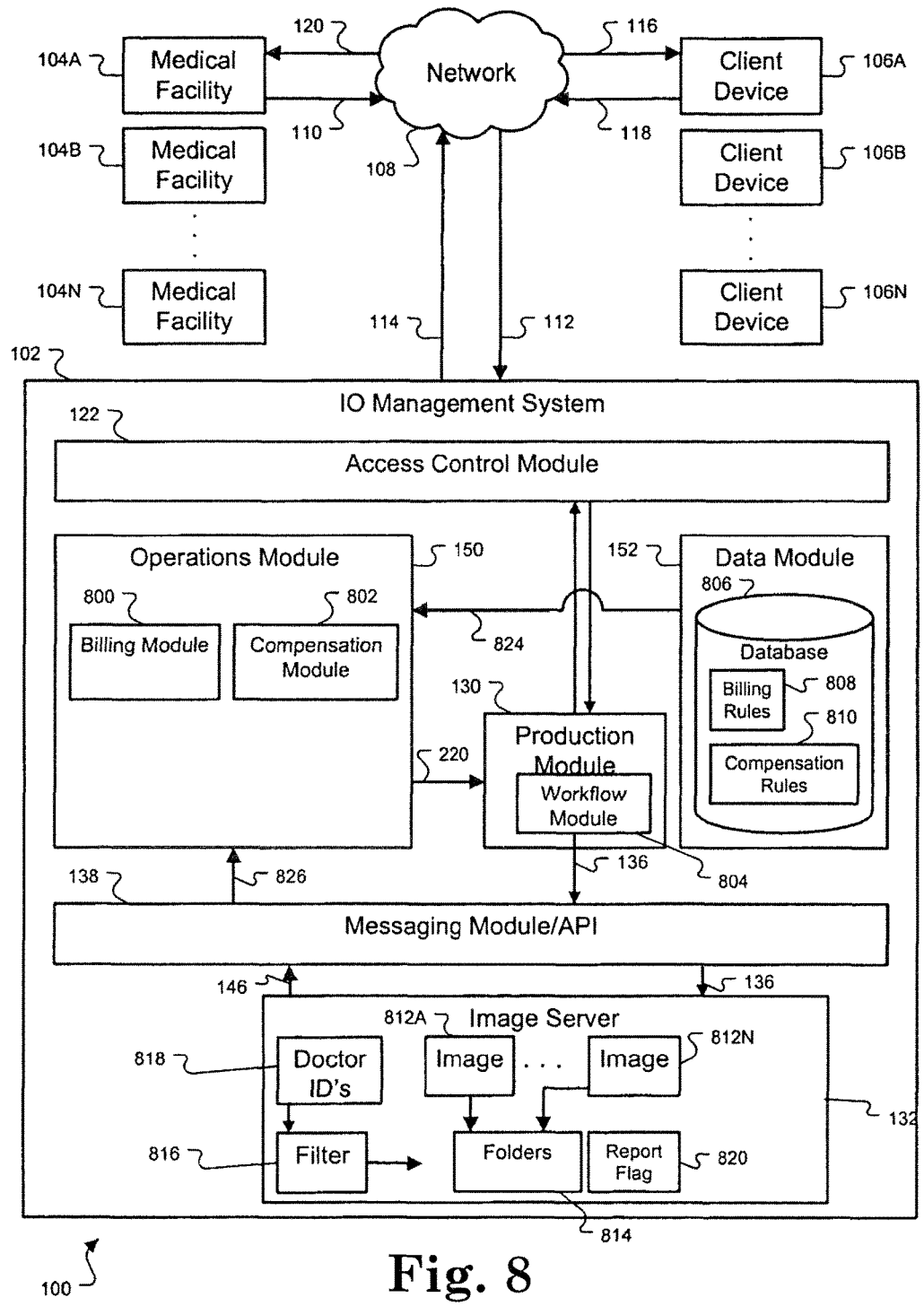
FIG. 8 illustrates a block diagram of the system shown in FIG. 2A with an additional implementation of image server functionality according to an embodiment of the present invention.

FIG. 8 is a block diagram of the processing system 100 illustrating more details relating to the image server. As discussed above, the IO Management System 102 may transmit images from the medical facilities 104 to the client devices 106. The operation module 150 may include a billing module 800 and a compensation module 802. The Production Module may include a workflow module 804, and the Data Module 152 may include a database 806 with billing rules 808 and compensation rules 810.

The Image Server 132 may include stored images 812, which may be placed in directories, or logical file folders 814 associated with particular doctors. The placement of the images in certain folders 814 may be determined by a filter 816, which may use filtering criteria, such as Doctor IDs 818 that may identify which images should be placed in which doctor's folders. The image server may also include a report flag 820, which indicates that a doctor has analyzed an image and submitted a report to the Order Server 140 (not shown) based on that image.

When an image is received from a medical facility by the IO Management System 102, it may be passed to the workflow module 804, which can determine which doctor may receive the image for study. The radiologist may be chosen from an available pool. Several criteria may be applied to determine radiologist's availability. For example, an examination of the radiologist's status with the facility may include determining whether a contract exists between the radiologist and the medical facility to provide services, whether the radiologist is licensed in the facility's state, whether the doctor is credentialed at the facility, the doctor's registered sub-specialties, and facility preferences with respect to specific radiologists. All of this data may be stored and accessed in the database 806.

The workflow module 804 may apply filtering to the order if multiple radiologists meet the first round selection criteria. Additional criteria used for filtering may include radiologist contractual information, such as compensation variations for orders. For example, Dr. A may receive a standard fee for an order sent Tuesday at 8 pm because Dr. A is contractually obligated to be on call and accept studies at this time. Dr. B however, is not on call at this time and is contractually entitled to receive the standard fee plus additional compensation for completing an order at this time. In this example, the study may be sent to Dr. A to minimize costs. Other contractual information that may affect the compensation may include the type of study, such as MRI, X-ray, or CAT, the body part depicted, and the number of orders already completed by a radiologist. This information may be retrieved from the database 806 in the system 102 for use in filtering. In another implementation, additional criteria for filtering may include the bidding price of a radiologist for completing an order or the compensation bid offered by a medical facility.

After the selected doctor or doctors have been determined by the workflow module, a list of Doctor IDs 818 corresponding to the selected doctors may be provided to the Image Server. The Doctor IDs 818 may be used by the filter 816 to determine which doctors should receive the images. For example, in one specific embodiment a set of folders or file locations 814 are each associated with a specific doctor to receive and hold the images. When the images are placed in the folders 814, they may then be transmitted to the doctors who are subscribed to those folders. For example, Dr. Cliff Huxtable may be subscribed to a folder associated with the Doctor ID CH. When an image is placed in the CH folder, it may be transmitted to the client device 106 that Dr. Huxtable uses. The images are the same images that were used by the workflow module 804 to determine the doctors available for analyzing the images.

In an alternate embodiment, instead of using folders, the Production Module 130 maintains a list of which studies are assigned to which radiologists—that is, a list of which radiologists have been approved to read each pending study. A caching module may then transmit the images to client devices such as client device 106 based on the assignments managed by the Production Module 130. As is apparent, a folder, list, or any other number of similar mechanisms may be used to maintain a list of valid reading radiologists for a given study and transmit the images and study data to the correct doctor location.

The doctor may be alerted of the image arrival, or the doctor may view it when an order associated with the images is selected. For instance, an order may appear on a radiologist's worklist, which may be displayed on the client device 106. The doctor may select the order and an image viewer that displays the image may open. In either case, the system may monitor the status of the order associated with the image and provide feedback to the ordering medical facility regarding the status of the order. If the order is not acted upon in a timely manner by the radiologist, additional radiologists may be assigned and provided the images and order information.

After the radiologist analyzes the images, the radiologist may submit a report to the system 102. The report may enter the system 102 through various means including direct typing, an audio file, such as a .wav file, voice recognition dictation, email text, or through use of a transcriptionist. Regardless of the source and format of the report from the radiologist, it may be converted, or reformatted, into a default format into the system while maintaining the electronic signature of the radiologist.

When the report is received by the system 102, the report flag 820 may be sent to the Image Server 132. The report flag may be transmitted with the report from the client device 106 or may be generated by the IO Management System 102 and transmitted to the Image Server 132 when the report is received. The report flag may be associated with the images to which it relates using DICOM information embedded in the image and information in the transmitted report, such as the facility that sent the image, and the patient name, or patient ID. The IO Management System 102 may associate the report flag with the images. The report flag may associated with the images in a way that indicates the images have been analyzed by a doctor. For example, the report flag may be stored with the images in the folder. This may prevent the images from being sent to another doctor or the same doctor for analysis.

In another implementation, the flag 820 may indicate that the images are old images related to a previous report. The images may be sent along with new images to a radiologist; however, the old images may be identified as older images using the report flag. The flag may be used to cause the image server to transmit the old images in way that indicates they are old. For example, the old images may be transmitted with information that indicates they have been read and provides the report corresponding to the images or a link to the report. The image viewer on the client device may separate the old and new images, so that the new images to be read are displayed with the order. If the doctor desires to see previous medical data, he or she may click on a link for the older images or the older report.

The report flag 820 may also be used to indicate that a transaction has been completed so that the billing module 800 and the compensation module 802 may calculate billing and compensation, respectively, for the transaction. The report flag may be received at the Image Server 132 and transmitted to the Operations Module 150. The report flag may contain information about the transaction, such as the time the report was completed, the doctor that completed it, the facility that requested it, the type of image read, the number of images, and the time the image was submitted to the doctor. Some or all of this information may be present in the report flag when it is transmitted from the client device, or it may be added at the Image Server 132. The billing rules 808 and the compensation rules 810 may be applied to the information extracted from the report flag to calculate the billing and compensation.

The billing module 800 may use billing rules 808 when calculating bills for the medical facilities 104. The billing rules 808 may be stored in a database 806 or within the billing module 800. If the rules 808 are stored within the database 806, the billing module 800 may retrieve the billing rules 808 from the database 806, as indicated by arrow 824. The billing module 800 may use the billing rules 808 together with the report flags 820 for a particular medical facility 104A in order to process the billing for that medical facility 104A. In one implementation, the report flags may be stored in the Image Server 132. The billing module 800 may retrieve the report flags, as represented by arrows 146 and 826.

For example, the bill for the medical facility 104A may depend on several rules applied to report flag extracted data. The data may include the order type, which may be an identifier signifying whether the order associated with the report was a preliminary study or a final study, the doctor identifier for the doctor completing the study, the time of day the order and the report were transmitted and received, the number of images associated with the report, the medical facility sending the images, and the region of the patient's body depicted in the image.

The rules may calculate different fees or charges based on this data. For example, one doctor identifier may be associated with a higher fee rule because the doctor may bill more for a read than other doctors. Additionally, the rules may include different fees based on whether an order was processed during the day or the night, or whether it was processed during a weekday or the weekend. Additionally, rules may be implemented where fees are modified based on the number of images associated with the report. For example, a base fee may be associated for the first 50 images, afterwards an excess image fee may be charged for each additional image. Some rules may change the image reading fee based on the medical facility sending the images. For instance, one medical facility may receive a lower fee for each order requested, if it contracts to send at least 50 orders every day. Some fees may align with CPT (Current Procedure Terminology) codes, or with other study procedure definitions. Fees may be aligned with requirements issued by state or federal government programs such as Medicaid and Medicare. Rules may also determine from the order type whether to charge a fee for a preliminary read or a final read. Additionally different rules may be created to generate a range of fees based on what type of body region is depicted in the image. For example, an order for a head scan may be charged a different fee than an order for a pelvic-abdomen scan.

There may also be flat fees or surcharges added to a bill that may be unrelated to the fulfilled order, such as a network maintenance fee for particular hospitals, on-call fees, or other one-time fees for special events. In another implementation, the report flags may be stored in the Data Module 152 and retrieved with the billing rules 808 to calculate the appropriate amount to bill the medical facility 104A.

In connection with use of the radiology processing system 100, some medical facilities 104 may work with an associated group of radiologists. The associated group may be referred to as a practice, or in other cases as a hospital or corporate organization of multiple hospitals. The billing module 800 may store billing rules 808 for a practice, individual radiologists, or combination thereof. Medical facilities 104 may be associated with practices in data structures located in the database 806. The association may be a hierarchal association, where one or more medical facilities 104 are linked to each practice. The medical facilities 104 may be considered delivery entities because they may deliver services to patients based upon the reports returned by radiologists.

The practices may be considered billing entities. The billing module 800 may generate bills or invoices on behalf of the practices. Invoices may be sent to the practices, which may bill the medical facilities 104. Alternatively, the invoices may be sent to the medical facilities 104 directly on behalf of another entity, such as the practices, the individual radiologists, or an entity that manages or controls the IO Management System 102.

Billing may occur on a periodic basis, such as daily or monthly, or billing may occur on an event basis, such as when a report flag is received by the IO Management System 102. Additionally, there may be a minimum number of orders or images charged per period regardless of whether a report flag is received. For example, if nine orders are requested and nine reports are received for the medical facility 104A in one daily period and the faculty has a minimum of ten orders in a daily period, the billing module 800 may charge the medical facility 104A for ten orders.

The billing module 800 may electronically debit the medical facilities 104, such as by an electronic fund transfer from a bank account or an electronic debit to a credit card. Additionally, the billing module 800 may output an invoice report that can be mailed, faxed, or electronically mailed to the medical facilities 104. In another example, the billing module 800 may output the billing information to an accounting services application that may create invoices for the medical facilities 104.

The compensation module 802 may use the report flag 820, compensation data, and compensation rules 810 when calculating the radiologists' compensation. The compensation data may be similar to the billing data described above. The compensation rules 810 may be stored in the database 806 or within the compensation module 802. If the rules 810 are stored within the database 806, the compensation module 802 may retrieve the rules 810 from the database 806, as indicated by arrow 824. The compensation module 802 may use the compensation rules 810 together with the compensation data and the data extracted from the report flag 820 to calculate the compensation for the radiologist associated with a report as indicated by the report flag.

For example, the data extracted from the report flag 820 may indicate whether a report was a preliminary or final study, what time the order was requested or processed, whether the report was submitted during a weekday or the weekend, whether the doctor was a subspecialist, whether the report as a result of a request for a second opinion or a consultation, and a doctor identifier for determining the appropriate compensation for that doctor. Additionally, compensation may be based on the number of images associated with the report, the type of image, or the part of the patient's body depicted in the image.

The compensation module 802 may implement compensation rules that use compensation data, such as a base rate per report, to compensate radiologists on a per report basis. There may be a base study count, or quota, of reports corresponding to a base salary for the radiologists, such that the compensation module 802 utilizes the compensation rules to calculate an additional compensation on a per report basis when the radiologist exceeds the quota.

Compensation may take multiple forms, for example, stock options in the entity managing the IO Management System 102, vacation days, or preferred scheduling requests may be compensation.

The compensation data may be recorded in a predetermined layout on a medium. For example, the compensation data may be recorded on a paper form. The form may be a contract with the compensation data recorded in predetermined parts, such as the base salary is listed in the first paragraph of the contract approximately three inches from the left side of the document and four inches from the top of the document. A user may enter the compensation data into a database, such as the database 806 by employing a GUI (graphical user interface) that has approximately the same layout as the digital or paper form. For example, the GUI may have a text entry box for base salary that is approximately three inches from the left side of the GUI and four inches from the top of the GUI. Alternatively, the form may be digitally represented on the GUI. For example, it may include all the text of the contract, with a text entry box located in approximately the same position in the first paragraph as the base salary in the paper contract. The user may quickly locate and enter all the necessary information using the similar representations of the GUI and the paper form.

In one implementation, the radiologists may bid on the compensation for the order, where the radiologist with the lowest bid may process the order. The medical facility may post the number of orders it needs fulfilled, and the radiologists may offer bids to fulfill the orders. For example, the workflow module 804 would attempt to assign orders to as many radiologists as possible while still honoring licensing and credentialing limitations, and facility preferences. There may also be limits, such as a limit on the number of orders currently accepted by a single radiologist. The limit may be based on the radiologist's productivity and the desired turnaround time for order completion. The radiologists may view and bid on orders assigned and not yet accepted by them at their client devices 106. The radiologist with the lowest bid may accept the order.

In another implementation, the medical facilities may provide compensation bids for a radiologist's services. Many facilities may bid to obtain the services offered by a radiologist. For example, a radiologist may submit an offer to provide 50 reports for requested orders over given time.

Medical facilities may submit compensation bids to have 50 of their orders completed by the radiologist. The medical facility with the highest compensation bid may be selected, and the radiologists may then receive 50 orders from that facility.

For monetary compensation, the compensation module 802 may electronically credit the radiologists, such as by an electronic fund transfer to a bank account. In another implementation, the compensation module 802 may output a check and a report that can be mailed, faxed, or electronically transmitted to the radiologists. In another example, the compensation module 802 may output the compensation information to an accounting services application that performs the electronic fund transfer or creates a report that can be sent to the radiologists. The compensation module 802 may also have a user interface, such as a portal application, where a radiologist can view reports of orders assigned to the radiologist and the compensation for those orders. The Access Control Module 122 may restrict access to the user interface for radiologist compensation, assigned orders, and submitted reports.

Figure 9:
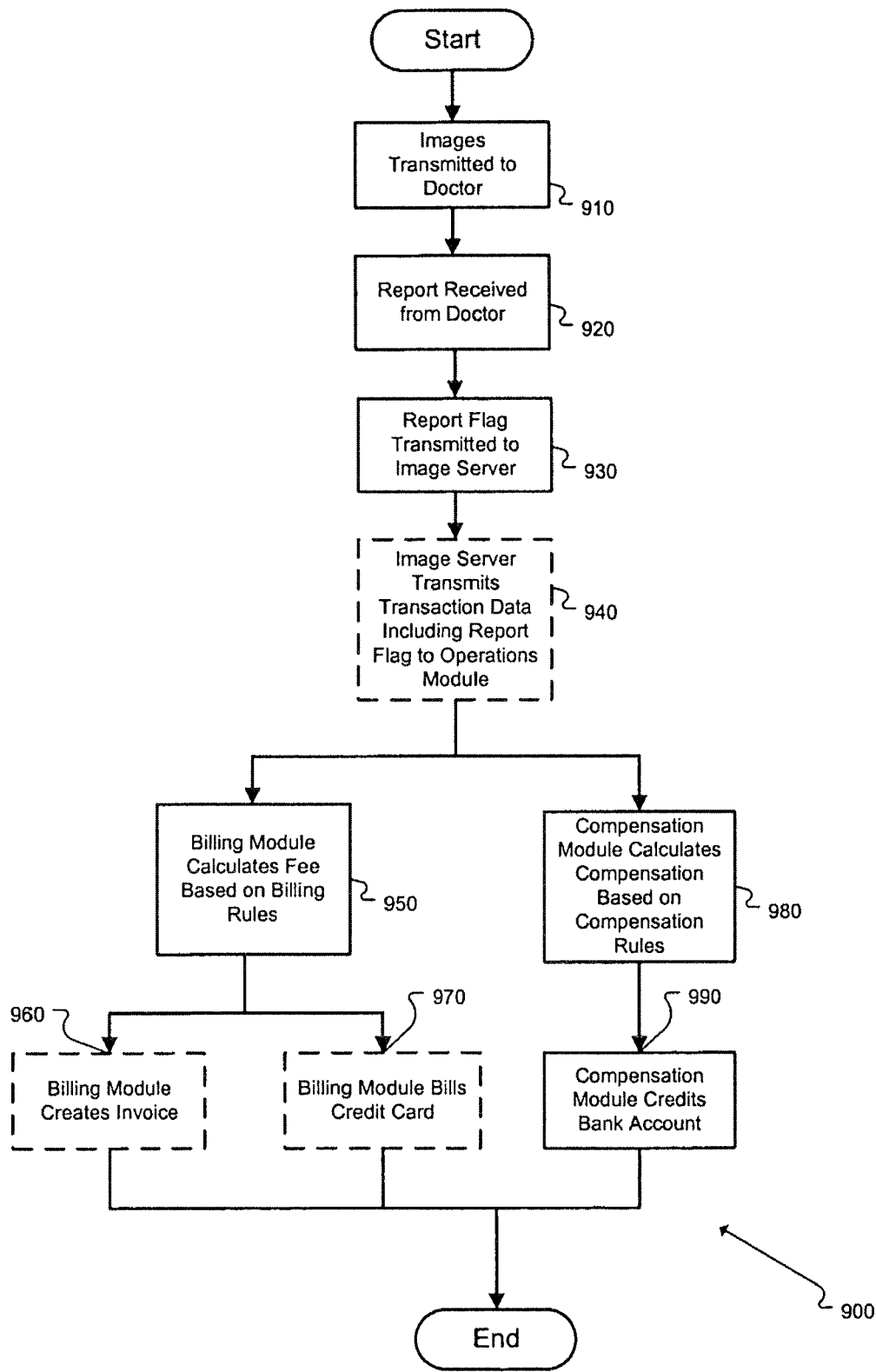
FIG. 9 illustrates a flowchart of example operations that the system may perform to calculate billing and compensation according to an embodiment of the present invention.

FIG. 9 is a flowchart of exemplary operations that the radiology processing system may use to calculate billing and compensation based on a report flag according to one implementation. For example, a computer program product may include instructions that cause a processor to perform operations comprising the steps of method 900.

In step 910, the operation "Images Transmitted to Doctor" is performed. The IO Management System transmits the images to the client device. For example, the IO Management System 102 may transmit the images for analysis to the client device 106 operated by a remote radiologist. The radiologists may be selected from a pool of available radiologists based on criteria, such as licensing, credentialing, schedule information, facility preferences, and the like.

In step 920, the operation "Receive Report from Doctor" is performed. The report may be received at the IO Management System 102 from the client device. For example, the doctor may generate a report based on the images received and transmit the report from the client device 106 to the system 102. In one implementation, a report flag 820 may be transmitted with a report from the client device 106.

In step 930, the operation "Report Flag Transmitted to Image Server" is performed. The report flag may be transmitted to the image server by the IO Management System 102. For example, the system 102 may generate a report flag when a report is received and forward the flag to the image server 132. In another implementation, the flag may be received with the report and transmitted to the image server 132 by the system 102.

In step 940, the operation "Image Server Transmits Transaction Data Including Report Flag to Operations Module" is performed. For example, the Image Server 132 may transmit the report flag to the Operations Module 150.

Steps 950 and 980 may occur independent of each other after step 940. In step 950, the operation "Billing Module Calculates Fee Based on Billing Rules" is performed. The billing module may apply the billing rules to information extracted from the report flag and generate a calculated fee. For example, data extracted from the report flag 820 may indicate that James River Hospital in Virginia submitted 150 images associated with the report. The billing rules 808 may be used by the billing module 800 to calculate the appropriate fees for 150 images and generate a fee total for James River Hospital. After the fee is calculated, either steps 960 or 970 may be optionally performed.

In optional step 960, the operation "Billing Module Creates Invoice" is performed. For example, the fee generated by the billing module 800 may be used to generate an invoice that is mailed to James River Hospital.

In optional step 970, the operation "Billing Module Bills Credit Card" is performed. For example, the billing module may debit the credit card account of James River Hospital. The credit card information may have been stored in the Data Module 152.

In step 980, the operation "Compensation Module Calculates Compensation Based on Compensation Rules" is performed. The compensation module may apply the compensation rules to information extracted from the report flag and generate a compensation amount for a doctor. For example, the data extracted from the report flag 820 may indicate that Dr. Huxtable generated the report and that the report exceeded the doctor's quota of reports. The compensation rules 810 may be used by the compensation module 802 to calculate Dr. Huxtable's compensation, including any bonuses for completing extra reports over his required limit.

In step 990, the operation "Compensation Module Credits Bank Account" is performed. The compensation module may electronically credit the bank account of a doctor that completes a report. For example, the compensation module 802 may access Dr. Huxtable's bank account information, which may be stored in the Data Module 152, and make an electronic deposit in the account for the calculated compensation using that information.

Figure 10:
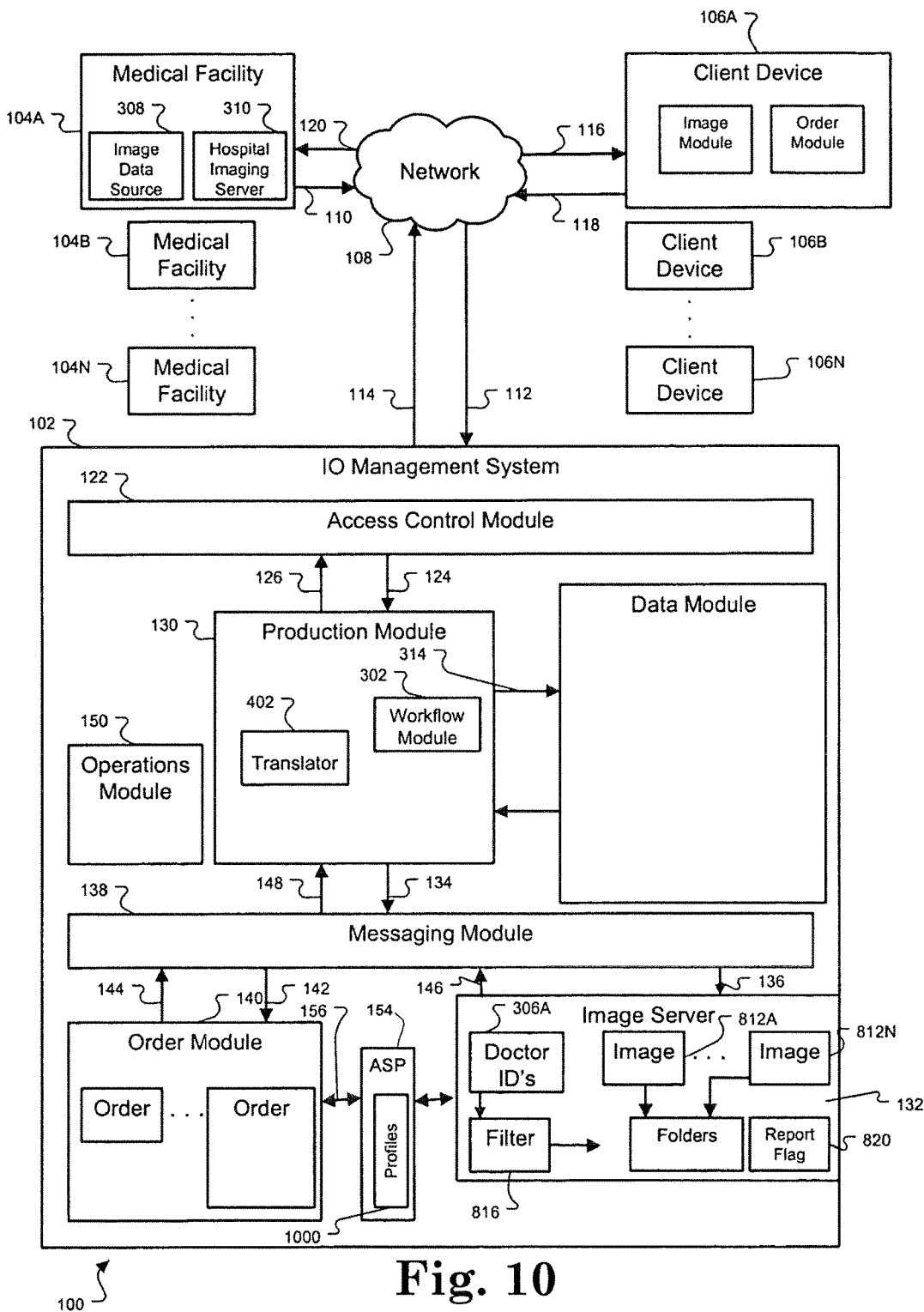
FIG. 10 illustrates a block diagram of the system shown in FIG. 2B with an additional implementation of ASP (Application Service Provider) functionality according to an embodiment of the present invention.

FIG. 10 is a block diagram of the radiology processing system 100 illustrating more features relating to the ASP (Application Service Provider). As briefly discussed previously, the ASP module 154 may provide a user of the client devices 106 access to orders and images from the order and image servers 140, 132, respectively. For example, a radiologist may access the IO Management System 102 through the Access Control Module 122 in a manner similar to the methods described above. A request to use the ASP module 154 may be passed to the module 154 directly, or it may pass through other modules, such as the Production Module 130 or the Messaging Module 138 for additional translation or work flow processing. The radiologist may then use the applications included in the ASP module to view the orders and images transmitted by the Medical Facilities 104, accept the orders, and return reports.

The radiologist does not need the full image and order applications installed on the client device 106 to access the images and orders, but instead may use the applications included in the ASP module. The ASP functionality may enable users of clients 106 to fulfill orders without locally installed order, report, and image software. In one implementation, the ASP module may be used to enable independent radiologists to fulfill orders without a full install of software compatible with the order and image servers 140, 132.

For example, after an image and order has been transmitted from a hospital to the IO Management System 102, a user of the client device 106 may be alerted that the order is available. This alert may be a request for bids from radiologists to complete the order or an assignment of the order to a particular radiologist. The alert may be sent out by electronic means, such as email, an order which shows up on the radiologist's worklist, or a request posted on a web server. The computing device transmitting or posting the alerts may be part of the IO Management System 102 or may be operated by an independent party, such as the hospital requesting the order or a representative for the hospital. The radiologist that is selected to complete the order may or may not have the software necessary to access the order and images or return the report. If the radiologist does not, he or she may employ the ASP module 154 to complete the order. In one implementation, the radiologist may access the module 154 using a browser and download plug-ins that permit the browser to utilize the ASP applications.

Using the ASP module 154 in combination with the image server and order server in the system 102 may permit the remote users to view the images and orders without downloading the all the data associated with the images and orders. For example, a doctor may view a scan with multiple images without having to download all of the data associated with each of the images. The doctor may view a "screenshot" of the image as manipulated by the image viewer used by the ASP. The data needed to manipulate the images does not need to be stored on the doctor's computer, instead it may be stored in the system 102, manipulated by the ASP applications, and the displayed manipulations may be transmitted to the remote user. The displayed manipulations may require less bandwidth to transmit than transmitting the full image data required to perform the manipulations, if the remote user had the appropriate image viewing software.

Additionally, the remote user may not need every image or every part of the image data for analysis. The doctor may not review the unneeded images or image data. Unneeded image data and even the "screenshot" of the unneeded images may not be transmitted to the remote doctor.

Not transmitting the full image may mitigate the need to compress (as well as decompress and translate) image data before transmitting it to or from a remote user. This may also be true for other medical data, such as reports and orders. Also, the image server may not have to push full images to client devices. Instead, client devices may log into the ASP module 154 to access the images without the need to receive the images, which may require large amounts of bandwidth to transmit.

In another implementation, the ASP module may have its own translator (not shown) or may utilize the translator 402 to translate the images, orders, or other medical information into a format compatible with software installed on the doctor's client device 106. In this implementation, the doctor may have a full image and order viewer on his or her system, but may require access to the images, orders, or other medical information in a format incompatible with the software installed on the client device 106. For example, the doctor may use an image viewer that only accepts image data in RadWorks format, while the images stored at the image server 132 are in raw DICOM format. The translator 402 may convert the images from DICOM format to RadWorks format before transmission to the client device 106.

The images, reports, and medical data may be stored or pre-loaded on the client device 106 for future reference or to decrease the time required by a doctor to manipulate or view the images or data. Translating, transmitting, and storing the data on the client device 106 may allow the client device's software to access the information in less time than accessing the same information resident on the IO Management System 102 because the size of the information may necessitate a significant transmission time from the IO Management System 102 to the client device 106.

The client device 106 may request that the IO Management System 102 transmit the images, reports, and medical data to the client device 106 for storage using a local caching module (not shown) implemented at the device 106. The local caching module may transmit the request to have the information stored locally if the information meets a size threshold. For example, an image may be 20 MB in size, and the size threshold is 8 MB. The local caching module transmits the requests to have the images stored at the client device 106 because remote viewing of the images causes undesirable delays in manipulating the images.

Alternatively, the local caching module may transmit the request if the client device 106 has adequate storage to contain the images, reports, and medical data. For instance, the client device issues two queries: the first is a query to a local hard drive to determine the amount of space available, and the second is a query to the IO Management System requesting the size of the information to be sent. Comparing the results from the two queries, the caching module may determine if the local hard drive has enough capacity to store the information. If enough capacity is available, the local caching module may transmit the request to have the information stored locally.

In another implementation, the local caching module may transmit the request if the connection established between the client device and the IO Management System 102 meets a threshold bandwidth. For example, if the client device determines that the connection averages 150 kbps, the client device may transmit a request that the information be stored locally. In some implementations, the functions performed by the local caching module at the client device 106 may be integrated into the caching module at the IO Management System 102. In these implementations, the caching module would transmit queries to the client device 106 to determine information, such as hard drive space, bandwidth threshold, and size threshold.

The reports and other medical data may be generated at the client device and transmitted to the ASP module. The ASP module may translate the received data into a default format and store the data in the IO Management System. The ASP module may also translate the received medical information into a format compatible with another client device or medical facility, and then may transmit it to the corresponding device or facility. For instance, a radiologist may log into the ASP module and receive images and an order issued by Hospital A. The doctor may create a report based on the images and order, and transmit this to the ASP module. The module may translate this report to a default format and then translate it to a format compatible with the report software used at Hospital A. The module may transmit the report to Hospital A.

Additionally, the ASP module may translate the report received from the radiologist directly into a format compatible with Hospital A, instead of first translating it into a default format.

In another example, a patient may log into or otherwise interface with the ASP module and receive his or her patient medical information, including images, reports, and demographic information. The patient may also edit demographic information, such as his or her home address. The patient may then transmit the edited information back to the ASP module. The patient's medical information may be stored in a default format on the IO Management System, or may be transmitted to one or medical facilities for storage.

Users logged into the ASP module may be limited from viewing, modifying, or deleting medical data. For example, the patient viewing his or her medical records may edit the demographic information, but may not edit the reports or images. In this example, the Access Control Module informs the ASP module as to which permissions a user is entitled using permission sets stored in the access control module.

The permission sets may indicate individual user IDs and restrictions or authorizations associated with those IDs. For example, a user ID may have doctor flag set to '1', which indicates the user is a doctor. Directories or files in the IO Management System may have an associated flag that indicates whether a doctor is permitted to modify the directory or file. The IO Management System 102 may access the permission sets associated with the user ID before allowing the corresponding user to access files stored on the system 102.

In another implementation, the reports and medical data are stored in a neutral, or default, format on the IO Management System 102. The information is translated to a format compatible with software installed on the client device 102, such as a browser. In one implementation, the translator 402 may remap or reformat the reports and medical data in various formats, such as HTML, XML, Java, or JavaScript, so that it may be displayed with an Internet browser. For example, the translator 402 may contain a set of translation rules, such as a RIS-to-HTML rule. The translator may use the RIS-to-HTML rule to take fields in a RIS order and generate an HTML document. The translator 402 may map the name "John Smith" in a patient name RIS field into an HTML document under a <heading> tag containing text "Patient Name."

The HTML document may be a template stored at the IO Management System. In this implementation, the field names in the RIS order may be matched to existing heading names in the HTML template. The data stored in the RIS data field is inserted under the corresponding heading name. Alternatively, the HTML document is dynamically generated based on the contents of the RIS order. For example, the translator 402 may generate an HTML heading tag for every field in the RIS order and include the information associated with each field in the header. The order of the RIS fields may used to determine the text of the heading tag. For instance, the first field may be the patient's name, so the translator 402 generates a HTML heading "Patient Name" for the first field.

When the doctors log into the ASP module 154, separate profiles 1000 may be available for different types of doctors. The profiles may control the type of image and order applications the ASP module presents the doctor, or may influence the way the images and orders are displayed within an application. For example, a cardiologist that logs into the ASP module 154 may be presented with images in 3-D to facilitate viewing blood flow around the heart in a cinematic fashion. This view may be desirable for cardiologists to accurately diagnose defects in the heart's function. In contrast, a radiologist may be presented with image data in a raw cross-sectional axial view progressing to a multiplanar reconstruction with the potential to move to 3-D and screen out certain image elements, such as bones, muscle, and tissue. These views may require the ASP module 154 to initiate different applications or initiate one application with specific options enabled for each type of specialist.

When the doctor submits a report using the ASP, the report flag 820 may be transmitted as discussed above. The billing module may use information extracted from the report flag to bill the doctor for access to the ASP module 154. The billing factors may include how much compensation the doctor is entitled to for completing the study. For example, the billing module may bill the doctor for an amount equivalent to 10% of the compensation he receives for analyzing the images. Alternatively, the doctor may be billed on the amount of information transferred to him or her during the ASP session, the length of the ASP session, or for every report completed by the doctor. The report flag may also be used to compensate the doctor and bill the medical facility as discussed above.

A number of implementations have been described. Nevertheless, it will be understood that various modifications may be made without departing from the spirit and scope of the described implementations. For example, in FIG. 3 steps 350 and 360 may be optional, and they may also be performed in the method 500 of FIG. 5. Additionally, the transfer of medical data in FIGS. 2A and 4 may occur among clients 106 and medical facilities 104 as well as between two medical facilities.

Figure 11:
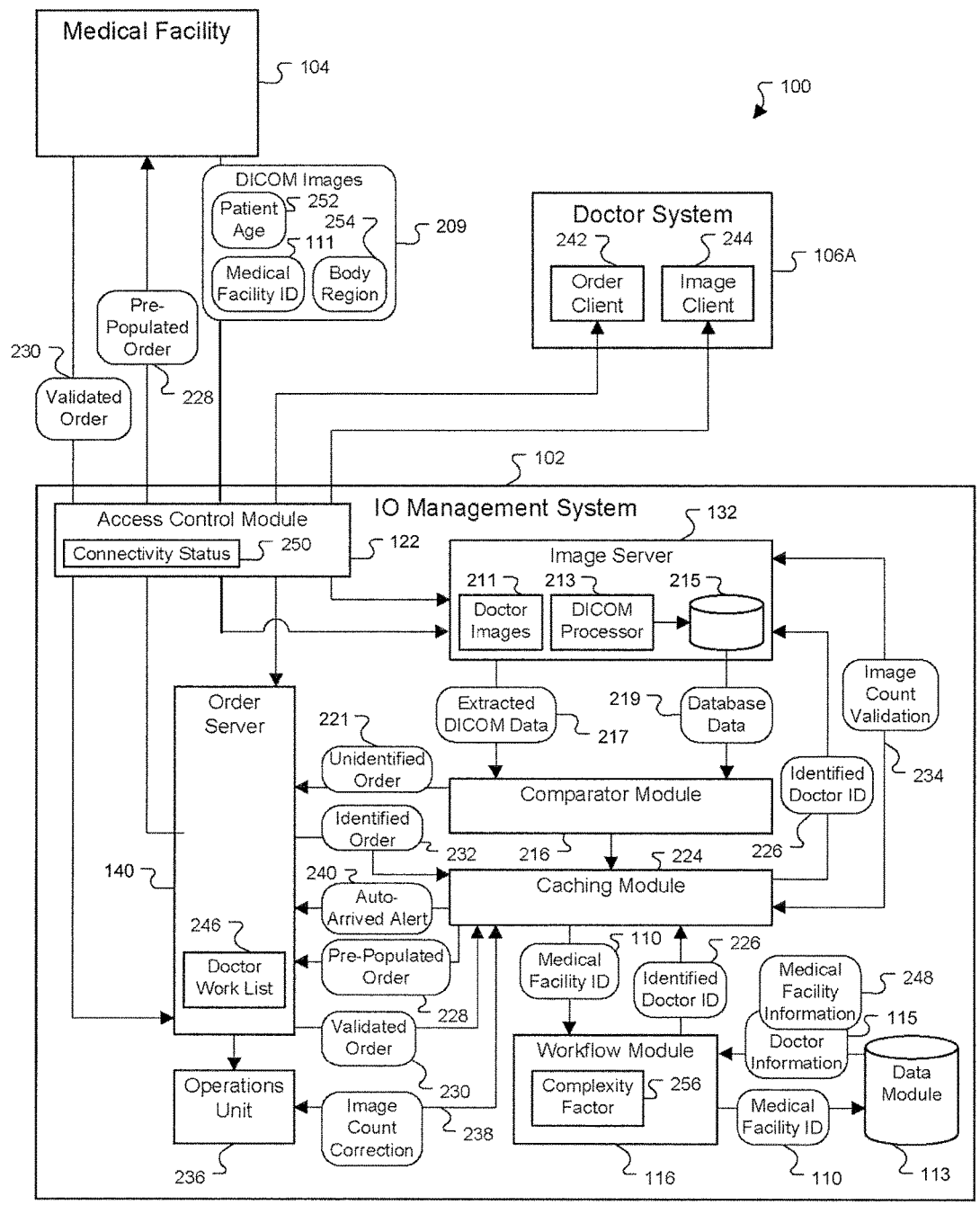
FIG. 11 illustrates a block diagram of an image order management system used for receiving and processing orders and images and initiating a teleradiology workflow according to an embodiment of the present invention.

FIG. 11 provides a further illustration of the components within an IO management system 102 and interaction between an IO management system and image data received from radiology devices of a medical facility 104 according to specific embodiment of the present invention configured for use in teleradiology processing. In summary, the IO management system 102 may contain or be interfaced with various components of a RIS and a PACS. These and other systems within the IO management system may be physically located or operated at disparate locations, at a single processing center, or in whole or in part by a third party service provider.

Within the IO management system 102, an image server 132 and an order server 140 receive images and orders, respectively, from the medical facility 104. The image server 132 and the order server 140 send the images and the orders to the doctor systems 106A-C for review by the doctors. An access control module 122 provides secure access to the IO management system 102 from the medical facility 104 and the doctor systems 106A-C.

As shown in FIG. 11, the medical facility 104 may send a medical request (e.g., a request for a radiologist review of electronic medical images) comprising DICOM images 209 to the IO management system 102. The image server 132 receives the DICOM images 209. The image server 132 may be part of a PACS, which digitally stores, transmits, and displays medical images. The image server 132 may store the image files as images 211. A DICOM processor 213 extracts DICOM data from the images and stores the DICOM data associated with the images in a database 215. The images are assigned an identifier that is stored in the database 215 and is used to access the images when needed for transmission or other purposes. When received, a compressor (not shown) may compress the images using a variety of compression algorithms to compress the images, such as JPEG, JPEGLS, JPEG2000, PNG, GIF, XBM, BMP, and TIFF.

The compressor may be implemented on the same computing device as the image server 132. In one implementation, the image compressor may be accessible by the software that executes the functions of the image server 132. For example, the image compressor may be a dynamic load library (DLL) code segment stored on the same computing device and accessed by the image server 132. Alternatively, the compressor may be implemented on a separate computing device from the image server 132. For example, the compressor may be accessible to software that executes the functionality of an Internet server, which is resident on a separate machine from the image server 132. The Internet server may access the compressor whenever it receives images from the image server 132 for transmission to the network.

Additionally, the database 215 and the images 211 may be stored at the image server 132. For example, the images and database may be stored on same machine that executes the image server software. This may simplify the operation and maintenance of the software. Alternatively, the images and database may be stored on a different machine from the image server. For example, the database may be installed on its own machine that has increased security protections and is isolated from the network in order to protect the medical data stored in the database. Similarly, the images may be installed on a separate machine that provides more storage capacity and specialized hardware that facilitates quick and efficient retrieval and storage of the images. After the workflow module assigns the orders and corresponding images to the selected doctors, the image server 132 may transmit the compressed images over the network to the doctor systems 106A-C.

In one embodiment configured to process DICOM-formatted images, a comparator module 216 receives extracted DICOM data 217 and database data 219 from the image server 132. The image server extracts the original DICOM data from the images 211 again and transmits it to the comparator module 216 for comparison with the database data 219. The comparison may be used to determine if the DICOM processor 213 stored the extracted data correctly and under the correct patient name. For example, if the medical facility ID 111 provided by the medical facility 104 is not unique within the database 215 the workflow module 116 may be unable to provide the correct ID to the data module 113 to filter the medical request. In addition, if a patient name included in the database data 219 and associated with the medical request does not match a patient name specified in the DICOM data 217, then the request may be incorrectly associated with the patient. If the request is incorrectly associated, then the comparator module 216 sends an unidentified order 221 to the order server 140 for correction. Otherwise, the comparator module 216 provides the medical facility ID 111 derived from the DICOM data included in the medical request to a caching module 224.

The caching module 224 caches information related to the medical request. The caching module 224 transmits the medical facility ID 111 to the workflow module 116. The workflow module transmits the medical facility ID 111 to the data module, which may use the facility ID 111 to access doctor information for doctors credentialed at a medical facility specified by the facility ID. The data module 113 then returns the doctor information 115 to the workflow module 116. Additionally, the data module may return medical facility information 248, such as how many requests per day the facility is contracted to request. The workflow module then performs filtering algorithms to determine a doctor to receive the request and returns an associated doctor ID 226 to the caching module.

The caching module 224 sends the identified doctor ID 226 to the image server 132. The image server 132 may place the images included in the medical request in file folders or directories associated with the identified doctor ID 226, or the images may be transmitted directly to a remote location or server such as the doctor system 106. The caching module 224 generates a pre-populated order 228 using the extracted DICOM data 217 and sends the pre-populated order 228 to the order server 140. In one specific embodiment, the pre-populated order serves as a formal order to read radiology images and is pre-populated with patient and hospital information, such as the hospital and patient name.

The order server 140 sends the pre-populated order 228 to the medical facility 104. The medical facility 104 validates the information contained in the pre-populated order 228 and sends the validated order 230 to the order server 140. For example, staff at the medical facility 104 may check the pre-populated information for correctness and specify or validate a number of images included in the request, a reason for the request, and a medical history of the patient. After receipt of the validated order, the order server 140 sends the validated order 230 to the caching module 224.

Unidentified orders 221 may also be corrected and then transmitted to the caching module 224. For example, personnel at the medical facility 104 may contact an operator with access to the order server. The medical facility personnel may provide the correct patient identification and other necessary information to correct the unidentified order 221. The operator may then correct the order 221, allowing the corrected order to be transmitted to the caching module 224 as an identified order 232.

In another implementation, unidentified orders 221 are corrected by transmitting a pre-populated order 228 to a "best guess" or "most likely" medical facility for confirmation. For example, the DICOM information associated with the unidentified order 221 may be used to generate a pre-populated order that includes the patient's name and other extracted information. If the originating facility is uncertain, the order server 140 may use probabilistic or statistical methods to determine the medical facility with the highest likelihood of being the originating facility. The order server may then transmit the pre-populated form with the patient information for confirmation. If the order server determines that more than one medical facility matches information from the DICOM header, the order server may send a pre-populated form to all the matching medical facilities. The confirmed order is ultimately then transmitted to the caching module 224.

As images included in a medical request are received, the caching module 224 queries the image server 132 to determine if the correct number of images have been received, as indicated by arrow 234. If there are either too few or too many images received, then the caching module 224 refers the medical request to an operations unit 236 where the image count is corrected, as indicated by arrow 238. In one implementation, the image count is manually corrected by an operator that may contact personnel at the medical facility to inquire about the image count. When the image count is correct, the caching module 224 sends to the order server 140 an auto-arrived alert 240, and the order associated with the received medical images is placed in the doctor work list 246 associated with the doctor assigned to review the medical request.

The order server 140 sends the validated order 230, which is in the doctor's work list 246, to the order client 242 at the doctor system 106A. The image server 132 transmits the images to an image client 244 at the doctor system 106A. The doctor system 106A is associated with the identified doctor ID 226 and it is accessible by the identified doctor. The doctor may then review the images 209 and the order 230 associated with the request. Ultimately, the doctor generates a report based on the review and the report is sent to the medical facility 104, either directly or through the IO management system 102.

In a further embodiment, a forecasting component may also be integrated within the IO Management System 102 to predict an amount and origin of future radiology read requests, estimate adequate radiologist staffing for future radiology reads, and reserve or forecast processing requirements of the teleradiology image processing system. This information, in turn, may also be used to ensure enough doctors are available to handle the predicted number and type of radiology read requests. Additionally, the information may be used to identify if more radiology read requests are needed to fully utilize the predicted amount of doctors available to review the requests.

The forecasting component may further operate to estimate future usage of the teleradiology image processing system based in part on data derived from the data transmission and the radiology read order. Thus, the forecasting component may use historical medical request data to generate a prediction for the amount and origin of medical requests occurring during the future time period. The prediction may indicate the average number of medical requests received per hour from a particular medical facility on a particular day of the week or similar time period. In another implementation, the forecasting component may use contractual information associated with each of the medical facilities to assist with generation of the prediction. For example, the prediction generator may use an indicator specifying a future timer period to determine what facilities are contractually obligated to submit requests during the period. Moreover, the predictive information may be used in workflows or other implemented processing in connection with the use and operation of the teleradiology image processing system.

Those skilled in the art would recognize that the various processing modules and components described herein, in addition to the overall structure and operation of a radiology processing system, may be adapted for use in a variety of healthcare and information processing settings. Thus, some of the components described herein may be removed or substituted without departing from the overall scope of the present invention. Additionally, portions of various components and modules described herein may be implemented or interfaced with existing healthcare and radiology processing systems (such as existing RIS and PACS systems).

The features of the present invention described herein may be implemented in digital electronic circuitry, or in computer hardware, firmware, software, or in combinations thereof. For example, a computer program product designed to perform functions of the described implementations may be embodied in one or more computer readable medium(s) having computer readable program code embodied thereon; an apparatus such as a computing system with a processor and memory may embody components structured to perform functions of the described implementations; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A program is generally a set of instructions that can be used, directly or indirectly, in a computer or other electronic programmable device to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

Although various representative embodiments of this invention have been described above with a certain degree of particularity, those skilled in the art could make numerous alterations to the disclosed embodiments without departing from the spirit or scope of the inventive subject matter set forth in the specification and claims.

What is claimed is:

1. An image processing system, comprising:
at least one hardware processor;
an image processing component comprising a plurality of instructions executed with the at least one hardware processor, the image processing component configured to, under computerized control:
extract data values from a set of electronic imaging data that includes a plurality of digital medical images, the plurality of digital medical images originating from a medical imaging procedure performed by a medical imaging modality at a medical facility;
a data processing component comprising a plurality of instructions executed with the at least one hardware processor, the data processing component configured to, under computerized control:
generate data values that identify characteristics of a diagnostic evaluation task for the plurality of digital medical images, based on the data values extracted from the set of electronic imaging data; and
determine at least one requirement for the diagnostic evaluation task, based on medical information included in the data values from the set of electronic imaging data;
a workflow component comprising a plurality of instructions executed with the at least one hardware processor, the workflow component configured to, under computerized control:
generate data values for electronic worklists associated with respective evaluators, the electronic worklists to list pending diagnostic evaluation tasks designated for performance by the respective evaluators, wherein the data values are communicated to computing systems of the respective evaluators;

initiate a command to designate a particular evaluator of the respective evaluators to perform the diagnostic evaluation task, wherein the particular evaluator is designated based on a match of at least one qualification of the particular evaluator with the at least one requirement of the diagnostic evaluation task; and update the electronic worklist for the particular evaluator in response to the command to designate the particular evaluator, wherein the electronic worklist for the particular evaluator is updated to include a pending state for the diagnostic evaluation task; and a data transmission component comprising a plurality of instructions executed with the at least one hardware processor, the data transmission component configured to, under computerized control:

transmit the plurality of digital medical images, via a network, to a computing device associated with the particular evaluator, in response to a command received from the particular evaluator via the electronic worklist to accept the diagnostic evaluation task from the pending state;

wherein the plurality of digital medical images are transmitted and made accessible to the computing device associated with the particular evaluator for performance of the diagnostic evaluation task, based on the acceptance of the diagnostic evaluation task and management of the electronic worklist for the respective evaluators, such that the plurality of digital medical images are not transmitted to the computing systems of the respective evaluators before acceptance of the diagnostic evaluation task.

2. The image processing system of claim 1, further comprising:

a request processing component comprising a plurality of instructions executed with the at least one hardware processor, the request processing component configured to, under computerized control, associate the electronic imaging data with request data from a request for the performance of the diagnostic evaluation task, the request data including data that specifies characteristics of an analysis of the plurality of digital medical images to be performed in the diagnostic evaluation task, wherein the data processing component is further configured to determine the at least one requirement for the diagnostic evaluation task based on the request data.

3. The image processing system of claim 1, wherein the data processing component is further configured to determine the at least one requirement for the diagnostic evaluation task on a basis of at least one requirement applicable to the plurality of evaluators that includes: licensing, credentialing, or specialization.

4. The image processing system of claim 1, wherein the diagnostic evaluation task of the plurality of digital medical images involves a radiological image interpretation, wherein the particular evaluator is a qualified radiologist and wherein the plurality of evaluators includes a plurality of remotely located radiologists, and wherein the workflow component is further configured to designate the particular evaluator based on a match with at least one assignment criterion, and wherein the at least one assignment criterion is used to assist the designation of the qualified radiologist from the plurality of remotely located radiologists.

5. The image processing system of claim 4, wherein the workflow component is further configured to designate the particular evaluator based on a match with information for the at least one assignment criterion, wherein the information relates to at least one of connection information for connectivity of computing devices associated with the remotely located radiologists, scheduling information for scheduled availability of the remotely located radiologists, forecasting information for projected availability of the remotely located radiologists, preference information of the remotely located radiologists, or preference information of a medical facility providing the electronic imaging data.

6. The image processing system of claim 1, wherein the diagnostic evaluation task of the plurality of digital medical images involves a pathological image examination, wherein the plurality of digital medical images are pathology images, wherein the particular evaluator is a pathologist and wherein the plurality of evaluators includes a plurality of remotely located pathologists, and wherein the diagnostic evaluation task includes a pathological examination of the digital medical images by the pathologist.

7. The image processing system of claim 1, wherein the workflow component is further configured to evaluate preferences of a medical facility for performing the diagnostic evaluation task, in connection with designation of the particular evaluator for performance of the diagnostic evaluation task.

8. The image processing system of claim 1, further comprising a patient information component comprising a plurality of instructions executed with the at least one hardware processor, the patient information component configured to, under computerized control, extract, correlate, and store patient information from the electronic imaging data, wherein the electronic imaging data is received in response to a performance of the medical imaging procedure at a remote location.

9. The image processing system of claim 1, wherein the image processing component is further configured to transform or convert at least one of the plurality of digital medical images prior to transmission of the plurality of digital medical images to the computing device associated with the particular evaluator.

10. The image processing system of claim 1, wherein the electronic worklists associated with the respective evaluators include an electronic worklist for another evaluator from the plurality of evaluators, and wherein the workflow component is further configured to:

initiate a command to designate the another evaluator to perform the diagnostic evaluation task, wherein the another evaluator is designated based on a match of at least one qualification of the particular evaluator with the at least one requirement of the diagnostic evaluation task;

update the electronic worklist for the another evaluator in response to the command to designate the another evaluator, wherein the electronic worklist for the another evaluator is updated to include a pending state for the performance of the diagnostic evaluation task; and update the electronic worklist for the another evaluator in response to acceptance of the diagnostic evaluation task by the particular evaluator, wherein the electronic worklist for the another evaluator is updated to remove the pending state for the performance of the diagnostic evaluation task.

11. A non-transitory machine-readable medium including instructions to process medical imaging data, the instructions which when executed by a computing machine cause the computing machine to perform operations that:

extract data values from a set of electronic imaging data that includes a plurality of digital medical images, the plurality of digital medical images originating from a medical imaging procedure performed by a medical imaging modality at a medical facility;

generate data values that identify characteristics of a diagnostic evaluation task for the plurality of digital medical images, based on the data values extracted from the set of electronic imaging data;

determine at least one requirement for the diagnostic evaluation task, based on medical information included in the data values from the set of electronic imaging data;

generate data values for electronic worklists associated with respective evaluators, the electronic worklists to list pending diagnostic evaluation tasks designated for performance by the respective evaluators, wherein the data values are communicated to computing systems of the respective evaluators;

initiate a command to designate a particular evaluator of the respective evaluators to perform the diagnostic evaluation task, wherein the particular evaluator is designated based on a match of at least one qualification of the particular evaluator with the at least one requirement of the diagnostic evaluation task;

update the electronic worklist for the particular evaluator in response to the command to designate the particular evaluator, wherein the electronic worklist for the particular evaluator is updated to include a pending state for the diagnostic evaluation task; and transmit the plurality of digital medical images, via a network, to a computing device associated with the particular evaluator, in response to a command received from the particular evaluator via the electronic worklist to accept the diagnostic evaluation task from the pending state;

wherein the plurality of digital medical images are transmitted and made accessible to the computing device associated with the particular evaluator for performance of the diagnostic evaluation task, based on the acceptance of the diagnostic evaluation task and management of the electronic worklist for the respective evaluators, such that the plurality of digital medical images are not transmitted to the computing systems of the respective evaluators before acceptance of the diagnostic evaluation task.

12. The machine-readable medium of claim 11, wherein the instructions cause the computing machine to further perform operations that:

associate the electronic imaging data with request data from a request for the performance of the diagnostic evaluation task, the request data including data that specifies characteristics of an analysis of the plurality of digital medical images to be performed in the diagnostic evaluation task;

wherein the at least one requirement for the diagnostic evaluation task is further determined based on the request data from the request for the performance of the diagnostic evaluation task.

13. The machine-readable medium of claim 11, wherein the instructions cause the computing machine to further perform operations that:

determine the at least one requirement for the diagnostic evaluation task on a basis of at least one requirement applicable to the plurality of evaluators that includes: licensing, credentialing, or specialization.

14. The machine-readable medium of claim 11, wherein the diagnostic evaluation task of the plurality of digital medical images involves a radiological image interpretation, wherein the particular evaluator is a qualified radiologist and wherein the plurality of evaluators includes a plurality of remotely located radiologists, and wherein the at least one assignment criterion assists the designation of the qualified radiologist from the plurality of remotely located radiologists.

15. The machine-readable medium of claim 14, wherein the instructions cause the computing machine to further perform operations that:

designate the particular evaluator for performance of the diagnostic evaluation task based on a match with information for the at least one assignment criterion, wherein the information relates to at least one of connection information for connectivity of computing devices associated with the remotely located radiologists, scheduling information for scheduled availability of the remotely located radiologists, forecasting information for projected availability of the remotely located radiologists, preference information of the remotely located radiologists, or preference information of a medical facility providing the electronic imaging data.

16. The machine-readable medium of claim 11, wherein the electronic worklists associated with the respective evaluators include an electronic worklist for another evaluator from the plurality of evaluators, and wherein the instructions cause the computing machine to further perform operations that:

initiate a command to designate the another evaluator to perform the diagnostic evaluation task, wherein the another evaluator is designated based on a match of at least one qualification of the particular evaluator with the at least one requirement of the diagnostic evaluation task;

update the electronic worklist for the another evaluator in response to the command to designate the another evaluator, wherein the electronic worklist for the another evaluator is updated to include a pending state for the performance of the diagnostic evaluation task; and update the electronic worklist for the another evaluator in response to acceptance of the diagnostic evaluation task by the particular evaluator, wherein the electronic worklist for the another evaluator is updated to remove the pending state for the performance of the diagnostic evaluation task.

17. A method for processing medical images in a workflow through use of an image processing system, the image processing system comprising at least one hardware processor configured to perform operations, the operations including:

extracting data values from a set of electronic imaging data that includes a plurality of digital medical images, the plurality of digital medical images originating from a medical imaging procedure performed by a medical imaging modality at a medical facility;

generating data values that identify characteristics of a diagnostic evaluation task for the plurality of digital medical images, based on the data values extracted from the set of electronic imaging data;

determining at least one requirement for the diagnostic evaluation task, based on medical information included in the data values from the set of electronic imaging data;

generating data values for electronic worklists associated with respective evaluators, the electronic worklists to list pending diagnostic evaluation tasks designated for performance by the respective evaluators, wherein the data values are communicated to computing systems of the respective evaluators;

initiating a command to designate a particular evaluator of the respective evaluators to perform the diagnostic evaluation task, wherein the particular evaluator is designated based on a match of at least one qualification of the particular evaluator with the at least one requirement of the diagnostic evaluation task;

updating the electronic worklist for the particular evaluator in response to the command to designate the particular evaluator; wherein the electronic worklist for the particular evaluator is updated to include a pending state for the diagnostic evaluation task; and transmitting the plurality of digital medical images, via a network, to a computing device associated with the particular evaluator, in response to a command received from the particular evaluator via the electronic worklist to accept the diagnostic evaluation task from the pending state;

wherein the plurality of digital medical images are transmitted and made accessible to the computing device associated with the particular evaluator for performance of the diagnostic evaluation task, based on the acceptance of the diagnostic evaluation task and management of the electronic worklist for the respective evaluators, such that the plurality of digital medical images are not transmitted to the computing systems of the respective evaluators before acceptance of the diagnostic evaluation task.

18. The method of claim 17, further comprising:

associating the electronic imaging data with request data from a request for the performance of the diagnostic evaluation task, the request data including data that specifies characteristics of an analysis of the plurality of digital medical images to be performed in the diagnostic evaluation task;

wherein the at least one requirement for the diagnostic evaluation task is further determined based on the request data.

19. The method of claim 17, further comprising:

determining the at least one requirement for the diagnostic evaluation task on a basis of at least one requirement of the plurality of evaluators that includes: licensing, credentialing, or specialization.

20. The method of claim 17, further comprising:

further designating the particular evaluator for performance of the diagnostic evaluation task based on a match with at least one assignment criterion, wherein the diagnostic evaluation task of the plurality of digital medical images involves a radiological image interpretation, wherein the particular evaluator is a qualified radiologist and wherein the plurality of evaluators includes a plurality of remotely located radiologists, and wherein the at least one assignment criterion assists the designation of the qualified radiologist from the plurality of remotely located radiologists.

21. The method of claim 17, further comprising:

further designating the particular evaluator for performance of the diagnostic evaluation task based on a match with information for the at least one assignment criterion, the particular evaluator being one of a plurality of remotely located radiologists, the information relating to at least one of: connection information for connectivity of computing devices associated with the remotely located radiologists, scheduling information for scheduled availability of the remotely located radiologists, forecasting information for projected availability of the remotely located radiologists, preference information of the remotely located radiologists, or preference information of a medical facility providing the electronic imaging data.

22. The method of claim 17, wherein the electronic worklists associated with the respective evaluators include an electronic worklist for another evaluator from the plurality of evaluators, and wherein the operations further include:

initiating a command to designate the another evaluator to perform the diagnostic evaluation task, wherein the another evaluator is designated based on a match of at least one qualification of the particular evaluator with the at least one requirement of the diagnostic evaluation task;

updating the electronic worklist for the another evaluator in response to the command to designate the another evaluator, wherein the electronic worklist for the another evaluator is updated to include a pending state for the performance of the diagnostic evaluation task; and updating the electronic worklist for the another evaluator in response to acceptance of the diagnostic evaluation task by the particular evaluator, wherein the electronic worklist for the another evaluator is updated to remove the pending state for the performance of the diagnostic evaluation task.

\* \* \* \* \*